US006617114B1

(12) United States Patent
Fowlkes et al.

(10) Patent No.: US 6,617,114 B1
(45) Date of Patent: Sep. 9, 2003

(54) IDENTIFICATION OF DRUG COMPLEMENTARY COMBINATORIAL LIBRARIES

(75) Inventors: Dana M. Fowlkes, Chapel Hill, NC (US); Brian K. Kay, Madison, WI (US); Jeffrey A. Frelinger, Chapel Hill, NC (US); Robin Parish Hyde-Deruyscher, Chapel Hill, NC (US)

(73) Assignee: Karo Bio AB, Huddinge (SE)

( * ) Notice: Subject to any disclaimer, the term of this patent is extended or adjusted under 35 U.S.C. 154(b) by 0 days.

(21) Appl. No.: 09/069,827

(22) Filed: Apr. 30, 1998

Related U.S. Application Data

(63) Continuation-in-part of application No. 09/050,359, filed on Mar. 31, 1998, which is a continuation-in-part of application No. PCT/US97/19638, filed on Oct. 31, 1997, which is a continuation-in-part of application No. 08/740,671, filed on Oct. 31, 1996, now abandoned.

(51) Int. Cl.$^7$ .............................................. G01N 33/53
(52) U.S. Cl. ................................. 435/7.1; 435/6; 435/5; 435/4; 435/DIG. 2; 435/DIG. 9; 435/DIG. 14; 435/DIG. 27; 530/350; 530/324; 530/325; 530/330
(58) Field of Search ............................... 405/7.1, 5, 6, 4, 405/DIG. 2, DIG. 9, DIG. 14, DIG. 22; 530/324, 325, 350, 330

(56) References Cited

U.S. PATENT DOCUMENTS

| | | | |
|---|---|---|---|
| 4,461,619 A | | 7/1984 | Hendry et al. |
| 4,664,989 A | | 5/1987 | Johnson |
| 5,133,866 A | * | 7/1992 | Kauvar ....................... 210/635 |
| 5,223,409 A | | 6/1993 | Ladner et al. |
| 5,288,514 A | | 2/1994 | Ellman |
| 5,449,754 A | | 9/1995 | Nishioka |
| 5,506,337 A | | 4/1996 | Summerton et al. |
| 5,539,083 A | | 7/1996 | Cook et al. |
| 5,545,568 A | | 8/1996 | Ellman |
| 5,549,974 A | | 8/1996 | Holmes |
| 5,556,762 A | | 9/1996 | Pinilla et al. |
| 5,892,014 A | * | 4/1999 | Coughlin et al. ........... 536/23.5 |
| 6,255,059 B1 | * | 7/2001 | Klein et al. ................. 435/7.31 |

FOREIGN PATENT DOCUMENTS

| | | |
|---|---|---|
| WO | 9401102 | 1/1994 |
| WO | 9519359 | 7/1995 |
| WO | 9604557 | 2/1996 |
| WO | WO 9609411 | 3/1996 |
| WO | WO 9729372 | 8/1997 |
| WO | WO 9740065 | 10/1997 |

OTHER PUBLICATIONS

Bottger, et al., *Identification of novel mdm2 binding peptides by phage display*, Oncogene, vol. 13, pp. 2141–2147, 1996.
Lu, et al., *Expression of Thioredoxin Random Peptide Libraries on the Escherichia coli Cell Surface as Functional Fusions to Flagellin: A System Designed for Exploring Protein–Protein Interactions*, Biotechnology, vol. 13, pp. 366–372, Apr. 1995.
Valadon, et al., *Peptide Libraries Define the Fine Specificity of Anti–polysaccharide Antibodies to Cryptococcus neoformans*, J. Mol. Biol., vol. 261, pp. 11–22, 1996.
Giebel, L. et al., "Screening of Cyclic Peptide Phage Libraries Identifies Ligands that Bind Streptavidin with High Affinities", Biochemistry 34:15430–15435 (1995).
Kay, Brian K., et al., "An M13 phage library displaying random 38–amino–acid peptides as a source of novel sequences with affinity to seleted targets", Gene 128:59–65 (1993).
Lam, Kit S. et al., "A new type of synthetic peptide library for identifying ligand–binding activity" Nature 354:82–84 (1991).
Smith, George P. et al., "A ribonuclease S–peptide antagonist discovered with a bacteriophage display library", Gene 128:37–42 (1993).
Healy, Judith M. et al., "Peptide ligands for Integrin avB3 selected from random phage display libraries", Biochemistry 34:3948–3955 (1995).
Koivunen, Erkki et al., "Isolation of a highly specific ligand for the $\alpha5\beta1$ integrin from a phage display library", J. Cell Biology 124:373–380 (1994).
Houghten, Richard A. et al., "Generation and use of synthetic peptide combinatorial libraries for basic research and drug discovery", Nature 354:84–86 (1991).

(List continued on next page.)

Primary Examiner—T. D. Wessendorf
(74) Attorney, Agent, or Firm—Iver P. Cooper

(57) ABSTRACT

The present invention is directed to the identification of compounds in a compound library which can mediate the biological activity of a target receptor protein, even when the ligands which mediate that activity through binding to that receptor are not already known.

The method of the invention includes the following three steps:
 (1) Screen a first combinatorial library for members binding to the target protein (TP) and hence capable of use as surrogates for the unknown ligand in steps (2) and (3).
 (2) Screen a second library, for compounds which inhibit the binding of one or more surrogates from step (1) to TP, and, optionally.
 (3) Determine whether the inhibitory compound mediates the biological activity of the said TP.

The first library is composed of peptides, peptoids and/or nucleic acids, and the second is not.

10 Claims, 19 Drawing Sheets

OTHER PUBLICATIONS

Marks, James D. et al., "By-passing Immunization Human Antibodies from V-gene Libraries Displayed on Phage", J. Mol. Biol. 222:581–597 (1991).

Colas, Pierre et al., "Genetic selection of peptide aptamers that recognize and inhibit cyclin-dependent kinase 2", Nature 380:548–550 (1996).

Smith, "Filamentous fusion phage: Novel expression vectors that display cloned antigens on the virion surfaces", Science 128:1315–1317 (1985).

Schmitz, Rita et al, "Catalytic Specificity of Phosphotryosine Kinases Blk, Lyn, c-Src and Syk as Assessed by Phage Display", J. Mol. Biol. 260:664–677 (1996).

Hong and Boulanger, "Protein ligands of the human adenovirus type 2 outer capsid idnetified by biopanning of a phage-displayed peptide library on separate domains of wild-type and mutant penton capsomers", EMBO J. 14 No. 19:4714–4727 (1995).

Simon et al., "Peptoids:A moldular approach to drug discovery", Proc. Natl. Acad. Sci. USA 89:9367–9371 (1992).

Bunin et al., "The combinatorial synthesis and chemical and biological evaluation of a 1,4-benzodiazepine library", Proc. Natl. Acad. Sci. USA 91:4708–4712 (1994).

DeWitt et al., "Diversomers': An approach to nonpeptide, nonoligomeric chemical diversity", Proc. Natl. Acad. Sci. USA 90:6909–6913 (1993).

Chen et al., "Analogous' Organic Synthesis of Small-Compound Libraries: Validation of Combinatorial Chemistry in Small-Molecule Synthesis", J. Am. Chem. Soc. 116:2661–2662 (1994).

Bunin et al., "A General and Expedient Method for the Solid-Phase Synthesis of 1,4-Benzodiazepine Derivatives", J. Am. Chem. Society 114:10997–10998 (1992).

Eichler, et al., *Peptide, Peptidomimetic, and Organic Synthetic Combinatorial Libraries*, Medical Research Reviews, vol. 15, No. 6, pp. 481–496, 1995.

Ellington, et al., *In vitro selection of RNA molecules that bind specific ligands*, Nature, vol. 346, pp. 818–822, Aug. 30, 1990.

Jacobsson, et al., *Cloning of Ligand–Binding Domains of Bacterial Receptors by Phage Display*, Biotechniques, vol. 18, No. 5, pp. 878–885, 1995.

Saggio, et al., *Biotin binders selected from a random peptide library expressed on phage*, Biochem J., vol. 293 (Pt 3), pp. 613–616, 1993, (Abstract).

Sepetov, et al., *Library of libraries: Approach to synthetic combinatorial library design and screening of "pharmacophore" motifs*, Proc. Natl. Acad. Sci. USA, vol. 92, pp. 5426–5430, Jun. 1995.

Siani, et al., *Chuckles: A Method for Representing and Searching Peptide and Peptoid Sequences on Both Monomer and Atomic Levels*, J. Chem. Inf. Comput. Sci., vol. 34, pp. 588–593, 1994.

Sparks, et al., *Cloning of ligand targets: Systematic isolation of SH3 domain–containing proteins*, Nature Biotechnology, vol. 14, pp. 741–744, Jun. 1996.

Bunin BA, et al, (1994) The combinatorial synthesis and chemical and biological evaluation of a 1,4-benzodiazepine library. Proc.Natl.Acad.Sci.U.S.A. 91: 4708–4712, 1994.*

Oliphant et al, Methods in Enzymology, 155, 1987, 568–582.*

* cited by examiner

- ▦ ER only
- ◩ estradiol
- ▥ estriol
- ▨ tamoxifen
- ■ nafoxidine
- ☐ clomiphene

SEQUENCE LISTING (1) GENERAL INFORMATION:

(iii) NUMBER OF SEQUENCES: 178

(2) INFORMATION FOR SEQ ID NO: 1:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 1:

GANNNKNNKN NKNNKTGGNN KNNKNNKNNK NNK                          33

(2) INFORMATION FOR SEQ ID NO: 2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

NNKGANNNKN NKNNKTGGNN KNNKNNKNNK NNK                          33

(2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

NNKNNKGANN NKNNKTGGNN KNNKNNKNNK NNK                          33

(2) INFORMATION FOR SEQ ID NO: 4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

NNKNNKNNKG ANNNKTGGNN KNNKNNKNNK NNK                          33

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

NNKNNKNNKN NKGANTGGNN KNNKNNKNNK NNK                          33

(2) INFORMATION FOR SEQ ID NO: 6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

NNKNNKNNKN NKNNKTGGGA NNNKNNKNNK NNK                          33

(2) INFORMATION FOR SEQ ID NO: 7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

NNKNNKNNKN NKNNKTGGNN KGANNNKNNK NNK                          33

(2) INFORMATION FOR SEQ ID NO: 8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

NNKNNKNNKN NKNNKTGGNN KNNKGANNNK NNK                          33

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

NNKNNKNNKN NKNNKTGGNN KNNKNNKGAN NNK                          33

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

NNKNNKNNKN NKNNKTGGNN KNNKNNKNNK GAN                          33

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Xaa Xaa Xaa Xaa Tyr Xaa Xaa Xaa Xaa Xaa
 1               5                  10

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Xaa Xaa Xaa Xaa Tyr Leu Xaa Xaa Xaa Xaa
1               5                   10
```

(2) INFORMATION FOR SEQ ID NO: 13:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Xaa Xaa Xaa Pro Pro Xaa Xaa Pro Xaa Xaa
1               5                   10
```

(2) INFORMATION FOR SEQ ID NO: 14:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Xaa Xaa Xaa Xaa Xaa Xaa Pro Xaa Pro Pro Xaa Pro Xaa Xaa
1               5                   10
```

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

```
CTGTGCGGAT CCATGGATCG CAAGACG                                27
```

(2) INFORMATION FOR SEQ ID NO: 16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

```
CTGTGCGAAT TCCTAGCCGC ACTTTTG                                27
```

(2) INFORMATION FOR SEQ ID NO: 17:

(i) SEQUENCE CHARACTERISTICS:
    (A) LENGTH: 63 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 17:

GACTGTGCCT CGAGKNNKNN KNNKNNKNNK YYYNNKNNKN NKNNKNNKTC TAGACGTGTC    60

AGT                                                                 63

(2) INFORMATION FOR SEQ ID NO: 18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

ACTGACACGT CTAGA                                                    15

(2) INFORMATION FOR SEQ ID NO: 19:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Xaa Xaa Xaa Xaa Xaa Xaa Xaa Xaa Xaa Xaa Cys Glu His Val Cys Ser
 1               5                  10                  15

Trp Gly Trp Gly Arg Cys
            20

(2) INFORMATION FOR SEQ ID NO: 20:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Pro Thr Ser Asp Leu Trp Arg Asn Leu Gly Gly
 1               5                  10

(2) INFORMATION FOR SEQ ID NO: 21:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Trp Gly Glu Thr Met Trp Asp Asn Arg Lys Val (2) INFORMATION FOR SEQ ID NO: 22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

```
Ala Gly Leu Thr Pro Trp Ser Leu Leu Val Asp
1               5                   10
```

(2) INFORMATION FOR SEQ ID NO: 23:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

```
Asp Thr Gly Thr Trp Trp His Ser Tyr Val Leu
1               5                   10
```

(2) INFORMATION FOR SEQ ID NO: 24:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

```
Arg Ala Pro Leu Ala Asp Arg Leu Leu Glu Gly
1               5                   10
```

(2) INFORMATION FOR SEQ ID NO: 25:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

```
Lys Leu Trp Ser Ala Asp Met Ser Ser Ile Val
1               5                   10
```

(2) INFORMATION FOR SEQ ID NO: 26:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

```
Phe Ile Val Gly Asn Asp Tyr Arg Leu Gly Lys
1               5                   10
```

(2) INFORMATION FOR SEQ ID NO: 27:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

```
Glu Gly Tyr Pro Ser Trp Val Tyr Met Gly Met
1               5                   10
```

(2) INFORMATION FOR SEQ ID NO: 28:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

```
Ala Arg Asp Phe Glu Asp Val Gln Gln Cys Cys
1               5                   10
```

(2) INFORMATION FOR SEQ ID NO: 29:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

```
Ser Gly Ser Gly Glu His Val Cys Ser Trp Gly Trp Gly Arg Cys
1               5                   10                  15
```

(2) INFORMATION FOR SEQ ID NO: 30:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

```
Ser Gly Ser Gly Glu His Val Cys Ser Trp Gly Trp Arg Cys
1               5                   10
```

(2) INFORMATION FOR SEQ ID NO: 31:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

GTTTTCCCAG TCACGAC                    17

(2) INFORMATION FOR SEQ ID NO: 32:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Gly Lys Gly Trp Lys Cys Phe Gly Ala Leu Cys
1               5                   10

(2) INFORMATION FOR SEQ ID NO: 33:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Ser Thr Thr Phe Gln Cys Val Gly Leu Leu Cys
1               5                   10

(2) INFORMATION FOR SEQ ID NO: 34:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Ala Asn Gly Trp Glu Cys Ile Gly Gln Phe Cys
1               5                   10

(2) INFORMATION FOR SEQ ID NO: 35:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

Lys Pro Val Trp Lys Cys Thr Gly Leu Phe Cys
1               5                   10

(2) INFORMATION FOR SEQ ID NO: 36:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

```
Ser Ala Gln Trp Gln Cys Val Gly Glu Phe Cys
1               5                   10
```

(2) INFORMATION FOR SEQ ID NO: 37:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
Leu Pro Met Ala Arg Trp Thr Cys Val Asn Cys
1               5                   10
```

(2) INFORMATION FOR SEQ ID NO: 38:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

```
Ala Val Asp Arg Gly Trp Thr Cys Val Asn Cys
1               5                   10
```

(2) INFORMATION FOR SEQ ID NO: 39:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

```
Gln Ile Thr Pro Gln Trp Thr Cys Ile Asn Cys
1               5                   10
```

(2) INFORMATION FOR SEQ ID NO: 40:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

```
Gly Val Cys Gln Ser Ser Asp His Arg Glu Cys
1               5                   10
```

(2) INFORMATION FOR SEQ ID NO: 41:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide

```
        (xi) SEQUENCE DESCRIPTION: SEQ ID NO: 41:

Gly Trp Gln Glu Arg Phe Gln Gln Glu Asp Arg
1               5                   10

(2) INFORMATION FOR SEQ ID NO: 42:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 42:

Glu Val Pro Thr Thr Lys Val Leu Trp Pro Ser
1               5                   10

(2) INFORMATION FOR SEQ ID NO: 43:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 43:

Pro Phe Gln Asp Tyr Trp Glu Glu Leu Leu Asn
1               5                   10

(2) INFORMATION FOR SEQ ID NO: 44:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 44:

Pro Phe His Ser Trp Trp Gln Asp Leu Thr Asp
1               5                   10

(2) INFORMATION FOR SEQ ID NO: 45:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 45:

Asn Phe Trp Asp Glu Trp Gln Thr Phe Met Asp
1               5                   10

(2) INFORMATION FOR SEQ ID NO: 46:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide
```

(xi) SEQUENCE DESCRIPTION: SEQ ID NO: 46:

Ser Phe Thr Asp Tyr Trp Arg Asp Leu Glu Gln
1               5                   10

(2) INFORMATION FOR SEQ ID NO: 47:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

Xaa Phe Xaa Asp Tyr Trp Gln Asp Leu Xaa Xaa
1               5                   10

(2) INFORMATION FOR SEQ ID NO: 48:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 48:

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

(2) INFORMATION FOR SEQ ID NO: 49:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
                20                  25                  30

Asn Asp Ile Leu
        35

(2) INFORMATION FOR SEQ ID NO: 50:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Gly Ala Pro Trp Asn Trp Glu Lys Lys Glu Leu
1               5                   10

(2) INFORMATION FOR SEQ ID NO: 51:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

```
Ala Asp Pro Arg Leu Pro Val Glu Arg Glu Leu
1               5                   10
```

(2) INFORMATION FOR SEQ ID NO: 52:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

```
Met Asp Gly Ser Gly Gly Glu Arg Asn Ser Met Trp
1               5                   10
```

(2) INFORMATION FOR SEQ ID NO: 53:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 53:

```
Pro Met Arg Thr Glu Trp Ala Val Gly Ser Glu Ser
1               5                   10
```

(2) INFORMATION FOR SEQ ID NO: 54:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 54:

```
Ser Arg Val Cys Ala Ile Trp Pro Asp Leu Asp Gly Cys Ser Arg
1               5                   10                  15
```

(2) INFORMATION FOR SEQ ID NO: 55:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 55:

```
Ser Arg Trp Cys Ser Leu Arg Pro Gln Asp Glu Gly Cys Ser Arg
1               5                   10                  15
```

(2) INFORMATION FOR SEQ ID NO: 56:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 56:

```
Ser Arg Trp Cys Glu Leu Trp Pro Glu Gly Ser Gly Cys Ser Arg
1               5                   10                  15
```

(2) INFORMATION FOR SEQ ID NO: 57:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

```
Ser Arg Trp Cys Glu Leu Trp Pro Glu Gly Ser Gly Cys Ser Arg
1               5                   10                  15
```

(2) INFORMATION FOR SEQ ID NO: 58:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 58:

```
Ser Arg Leu Cys Glu Val Trp Pro Gln Thr Ala Gly Cys Ser Arg
1               5                   10                  15
```

(2) INFORMATION FOR SEQ ID NO: 59:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 59:

```
Ser Arg Trp Cys Asp Ile Trp Pro Asp Thr Gly Ser Cys Ser Arg
1               5                   10                  15
```

(2) INFORMATION FOR SEQ ID NO: 60:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 60:

```
Ser Arg Leu Cys Asp Ile Met Pro Gln Thr Val Gly Cys Ser Arg
```

(2) INFORMATION FOR SEQ ID NO: 61:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 61:

```
Ser Arg Trp Cys Glu Val Trp Pro Asp Lys Arg Trp Cys Ser Arg
1               5                   10                  15
```

(2) INFORMATION FOR SEQ ID NO: 62:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 62:

```
Ser Arg Trp Cys Trp Pro Xaa Xaa Gly Cys Ser Arg
1               5                   10
```

(2) INFORMATION FOR SEQ ID NO: 63:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..45

(xi) SEQUENCE DESCRIPTION: SEQ ID NO: 63:

```
TCG AGG GTG TGT GCT ATT TGG CCG GAT CTG GAT GGT TGC TCT AGA    45
Ser Arg Val Cys Ala Ile Trp Pro Asp Leu Asp Gly Cys Ser Arg
1               5                   10                  15
```

(2) INFORMATION FOR SEQ ID NO: 64:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 64:

```
Ser Arg Val Cys Ala Ile Trp Pro Asp Leu Asp Gly Cys Ser Arg
1               5                   10                  15
```

(2) INFORMATION FOR SEQ ID NO: 65:

(i) SEQUENCE CHARACTERISTICS:
        (A) LENGTH: 45 base pairs
        (B) TYPE: nucleic acid
        (C) STRANDEDNESS: single
        (D) TOPOLOGY: linear

```
        (ii) MOLECULE TYPE: cDNA (ix) FEATURE:
              (A) NAME/KEY: CDS
              (B) LOCATION:1..45

(xi) SEQUENCE DESCRIPTION: SEQ ID NO: 65:

TCG AGG TGG TGT GAG TTG TGG CCG GAG GGT TCT GGT TGT TCT AGA         45
Ser Arg Trp Cys Glu Leu Trp Pro Glu Gly Ser Gly Cys Ser Arg
 1               5                  10                  15

(2) INFORMATION FOR SEQ ID NO: 66:

(i) SEQUENCE CHARACTERISTICS:
              (A) LENGTH: 15 amino acids
              (B) TYPE: amino acid
              (D) TOPOLOGY: linear (ii) MOLECULE TYPE: protein (xi) SEQUENCE DESCRIPTION: SEQ ID NO: 66:

Ser Arg Trp Cys Glu Leu Trp Pro Glu Gly Ser Gly Cys Ser Arg
 1               5                  10                  15

(2) INFORMATION FOR SEQ ID NO: 67:

(i) SEQUENCE CHARACTERISTICS:
              (A) LENGTH: 12 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 67:

Leu Tyr Ser Trp Pro Asp Glu Gln Tyr Glu Arg Pro
 1               5                  10

(2) INFORMATION FOR SEQ ID NO: 68:

(i) SEQUENCE CHARACTERISTICS:
              (A) LENGTH: 11 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 68:

Phe Gly Phe Tyr Gly Trp Pro Asp Asp Gln Tyr
 1               5                  10

(2) INFORMATION FOR SEQ ID NO: 69:

(i) SEQUENCE CHARACTERISTICS:
              (A) LENGTH: 12 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 69:

Met Tyr Thr Trp Pro Gly Ser Pro Tyr Leu Gln Met
 1               5                  10

(2) INFORMATION FOR SEQ ID NO: 70:

(i) SEQUENCE CHARACTERISTICS:
```

(A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 70:

Met Tyr Ser Trp Pro Gly Glu His Tyr Thr Val His
1               5                   10

(2) INFORMATION FOR SEQ ID NO: 71:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 71:

Met Tyr Ala Trp Pro Asp Ser Ser Glu Leu Glu Lys
1               5                   10

(2) INFORMATION FOR SEQ ID NO: 72:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 72:

Met Tyr Ser Trp Pro Gly Val
1               5

(2) INFORMATION FOR SEQ ID NO: 73:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 73:

Tyr Tyr Gly Trp Pro Ser Glu
1               5

(2) INFORMATION FOR SEQ ID NO: 74:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

Asp Arg Val Tyr Gly Trp Pro Pro Phe Glu Glu
1               5                   10

(2) INFORMATION FOR SEQ ID NO: 75:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 75:

Ala Tyr His Trp Pro Trp Val Glu Ser Glu Trp
1               5                   10

(2) INFORMATION FOR SEQ ID NO: 76:

(i) SEQUENCE CHARACTERISTICS:
    (A) LENGTH: 13 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 76:

Gly Tyr Ser Trp Pro Trp Pro Asp Asp Asn Ala Ser Arg
1               5                   10

(2) INFORMATION FOR SEQ ID NO: 77:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 77:

Ile Tyr Ser Trp Pro Trp Pro Ser Asn Glu Asn
1               5                   10

(2) INFORMATION FOR SEQ ID NO: 78:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 78:

Gln Tyr Thr Trp Pro Trp Pro
1               5

(2) INFORMATION FOR SEQ ID NO: 79:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 79:

Tyr Ser Trp Pro Trp Asp Phe Asn Glu Thr
1               5                   10

(2) INFORMATION FOR SEQ ID NO: 80:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 80:

```
Ala Tyr Ser Trp Pro Trp His Asp Thr Val Asp
1               5                   10
```

(2) INFORMATION FOR SEQ ID NO: 81:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 81:

```
Trp Asp Gly Phe Ala Trp Pro Met His Gln Thr
1               5                   10
```

(2) INFORMATION FOR SEQ ID NO: 82:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 82:

```
Trp Pro Trp Gly Gly Phe Glu Trp Pro Lys Leu
1               5                   10
```

(2) INFORMATION FOR SEQ ID NO: 83:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 83:

```
Arg Tyr Trp Trp Pro Asp Trp Gly Ser Arg Glu
1               5                   10
```

(2) INFORMATION FOR SEQ ID NO: 84:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 84:

```
Leu Trp Trp Pro Glu Trp Gly Val Tyr Thr Gly
1               5                   10
```

```
(2) INFORMATION FOR SEQ ID NO: 85:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 85:

Tyr Phe Trp Trp Pro Asp Trp Gly Ser Ala
1               5                   10

(2) INFORMATION FOR SEQ ID NO: 86:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 86:

Asp Arg Gly Trp Trp Pro Ser Trp Gly Val Ser Arg
1               5                   10

(2) INFORMATION FOR SEQ ID NO: 87:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 87:

Gly Tyr Trp Trp Pro Asp Trp Gly Ser Gly Gln
1               5                   10

(2) INFORMATION FOR SEQ ID NO: 88:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 88:

Ala Glu Tyr Trp Trp Pro Asp Trp Gly Phe Phe
1               5                   10

(2) INFORMATION FOR SEQ ID NO: 89:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 89:

Arg Leu Gln Tyr Trp Trp Pro Asp Trp Gly Pro
1               5                   10
```

(2) INFORMATION FOR SEQ ID NO: 90:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 90:

```
Met Tyr Trp Trp Pro Asn Trp Gly Ser Gln Glu
1               5                   10
```

(2) INFORMATION FOR SEQ ID NO: 91:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 91:

```
Trp Leu Asp Gly Leu Pro Leu Tyr His Glu Val
1               5                   10
```

(2) INFORMATION FOR SEQ ID NO: 92:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 92:

```
Asp Thr Val Arg Lys Asp Leu Leu Glu Arg Glu
1               5                   10
```

(2) INFORMATION FOR SEQ ID NO: 93:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 93:

```
Tyr Xaa Trp Pro
1
```

(2) INFORMATION FOR SEQ ID NO: 94:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 94:

```
Tyr Trp Trp Pro Asp Trp Gly
1               5
```

(2) INFORMATION FOR SEQ ID NO: 95:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 95:

```
Ser Ser Gln Thr Asp Trp Arg Lys Ile Phe Gln Ser Leu Ser Arg
1               5                   10                  15
```

(2) INFORMATION FOR SEQ ID NO: 96:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 96:

```
Ser Ser Ser Thr Asp Trp Leu Asn Val Trp Arg Gln Leu Ser Arg
1               5                   10                  15
```

(2) INFORMATION FOR SEQ ID NO: 97:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 97:

```
Ser Ser Ala Thr Asp Trp Gly Arg Val Tyr Ser Ile Leu Ser Arg
1               5                   10                  15
```

(2) INFORMATION FOR SEQ ID NO: 98:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 98:

```
Ser Ser Ala Ser Tyr Ala Pro Trp Pro Ile Tyr Phe Ala Ser Arg
1               5                   10                  15
```

(2) INFORMATION FOR SEQ ID NO: 99:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 99:

```
Ser Ser Gly Ala Phe Lys Pro Trp Pro Val Tyr Ser Phe Ser Arg
```

```
1               5                   10                  15
```

(2) INFORMATION FOR SEQ ID NO: 100:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 100:

```
Ser Arg Gln Val Glu Val Phe Lys Pro Trp Pro Val Tyr Ser Arg
1               5                   10                  15
```

(2) INFORMATION FOR SEQ ID NO: 101:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 101:

```
Ser Ser Ser Phe Lys Pro Trp Pro Ile Tyr Leu Gly Ser Ser Arg
1               5                   10                  15
```

(2) INFORMATION FOR SEQ ID NO: 102:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 102:

```
Ser Ser Glu Pro Phe Ser Val Trp Pro Ile Tyr Lys His Ser Arg
1               5                   10                  15
```

(2) INFORMATION FOR SEQ ID NO: 103:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 103:

```
Ser Ser Ser Val Pro Phe Ala Pro Trp Pro Val Tyr Ala Ser Arg
1               5                   10                  15
```

(2) INFORMATION FOR SEQ ID NO: 104:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 104:

```
Ser Ser Thr Ser Leu Pro Phe Asn Arg Trp Pro Ile Tyr Ser Arg
1               5                   10                  15
```

(2) INFORMATION FOR SEQ ID NO: 105:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 105:

```
Ser Arg Leu Leu Glu Val Ser Pro Gly Trp Trp Gln Met Ser Arg
1               5                   10                  15
```

(2) INFORMATION FOR SEQ ID NO: 106:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 106:

```
Ser Ser Phe Arg Glu Leu Lys Pro Gly Trp Trp Ser Tyr Ser Arg
1               5                   10                  15
```

(2) INFORMATION FOR SEQ ID NO: 107:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 107:

```
Ser Ser Trp Gly Asp Tyr Phe Asn Trp Arg Asp Gly Leu Ser Arg
1               5                   10                  15
```

(2) INFORMATION FOR SEQ ID NO: 108:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 108:

```
Ser Arg Gln Val Glu Val Phe Lys Pro Trp Pro Val Tyr Ser Arg
1               5                   10                  15
```

(2) INFORMATION FOR SEQ ID NO: 109:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 109:

```
Ser Ser Ser Phe Lys Pro Trp Pro Ile Tyr Leu Gly Ser Ser Arg
1               5                  10                  15
```

(2) INFORMATION FOR SEQ ID NO: 110:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 110:

```
Ser Val Ser Val Gly Met Lys Pro Ser Pro Arg Pro
1               5                  10
```

(2) INFORMATION FOR SEQ ID NO: 111:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 111:

```
Ser Ser Asn Tyr Trp Trp Gln Ser Pro Val Leu Ser Arg His Ser Arg
1               5                  10                  15
```

(2) INFORMATION FOR SEQ ID NO: 112:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 112:

```
Ser Ser Trp Gln Gly Asn Val Leu Leu Gly Asn Trp Ile Ser Arg
1               5                  10                  15
```

(2) INFORMATION FOR SEQ ID NO: 113:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 113:

```
Ser Ser Leu Leu Asn Glu Ser Arg Leu Gln Trp Ser Thr Ser Arg
1               5                  10                  15
```

(2) INFORMATION FOR SEQ ID NO: 114:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide

```
      (xi) SEQUENCE DESCRIPTION: SEQ ID NO: 114:

Ser Arg Asp Trp Gly Phe Trp Asp Trp Gly Val Asp Arg Ser Arg
1               5                  10                  15

(2) INFORMATION FOR SEQ ID NO: 115:

(i) SEQUENCE CHARACTERISTICS:
          (A) LENGTH: 16 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 115:

Ser Arg Asp Trp Gly Phe Trp Arg Leu Pro Glu Ser Met Ala Ser Arg
1               5                  10                  15

(2) INFORMATION FOR SEQ ID NO: 116:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 116:

Ser Arg Glu Trp His Phe Trp Arg Asp Tyr Asn Pro Thr Ser Arg
1               5                  10                  15

(2) INFORMATION FOR SEQ ID NO: 117:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 117:

Ser Ser Glu Arg Gly Ser Gly Asp Arg Gly Glu Lys Gly Ser Arg
1               5                  10                  15

(2) INFORMATION FOR SEQ ID NO: 118:

(i) SEQUENCE CHARACTERISTICS:
          (A) LENGTH: 77 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 118:

Leu Asn Gly Ser Ala Gly Asp Thr Trp Arg His Leu Ala Gly Glu Leu
1               5                  10                  15

Gly Tyr Gln Pro Glu His Ile Asp Ser Phe Thr His Glu Ala Cys Pro
            20                  25                  30

Val Arg Ala Leu Leu Ala Ser Trp Ala Thr Gln Asp Ser Ala Thr Leu
        35                  40                  45

Asp Ala Leu Leu Ala Ala Leu Arg Arg Ile Gln Arg Ala Asp Leu Val
    50                  55                  60

Glu Ser Leu Cys Ser Glu Ser Thr Ala Thr Ser Pro Val
```

```
               65                   70                  75

(2) INFORMATION FOR SEQ ID NO: 119:

(i) SEQUENCE CHARACTERISTICS:
        (A) LENGTH: 84 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 119:

Ala Gly Val Met Thr Leu Ser Gln Val Lys Gly Phe Val Arg Lys Asn
 1               5                  10                  15

Gly Val Asn Glu Ala Lys Ile Asp Glu Ile Lys Asn Asp Asn Val Gln
                20                  25                  30

Asp Thr Ala Glu Gln Lys Val Gln Leu Leu Arg Asn Trp His Gln Leu
            35                  40                  45

His Gly Lys Lys Glu Ala Tyr Asp Thr Leu Ile Lys Asp Leu Lys Lys
        50                  55                  60

Ala Asn Leu Cys Thr Leu Ala Glu Lys Ile Gln Thr Ile Ile Leu Lys
65                  70                  75                  80

Asp Ile Thr Ser (2) INFORMATION FOR SEQ ID NO: 120:

(i) SEQUENCE CHARACTERISTICS:
        (A) LENGTH: 84 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 120:

Thr Asp Asp Pro Ala Thr Leu Tyr Trp Lys Glu Phe Val Arg Arg Leu
 1               5                  10                  15

Gly Leu Ser Asp His Glu Ile Asp Arg Leu Glu Leu Gln Asn Gly Arg
                20                  25                  30

Cys Leu Arg Glu Ala Gln Tyr Ser Met Leu Ala Thr Trp Arg Arg Arg
            35                  40                  45

Thr Arg Arg Glu Ala Thr Leu Glu Leu Leu Gly Arg Val Leu Arg Asp
        50                  55                  60

Met Asp Leu Leu Gly Cys Leu Glu Asp Ile Glu Glu Ala Leu Cys Ala
65                  70                  75                  80

Pro Pro Leu Pro (2) INFORMATION FOR SEQ ID NO: 121:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 121:

Leu Xaa Xaa Leu Leu
 1               5
```

```
(2) INFORMATION FOR SEQ ID NO: 122:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 122:

Ser Arg Thr Trp Glu Ser Pro Leu Gly Thr Trp Glu Trp Ser Arg
1               5                   10                  15

(2) INFORMATION FOR SEQ ID NO: 123:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 123:

Ser Ser Lys Tyr Ser Tyr Ser Arg Ser Ser Glu Gly His Ser Arg
1               5                   10                  15

(2) INFORMATION FOR SEQ ID NO: 124:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 124:

Ser Ser Trp Val Arg Leu Ser Asp Phe Pro Trp Gly Val Ser Arg
1               5                   10                  15

(2) INFORMATION FOR SEQ ID NO: 125:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 125:

Ser Ser Trp Asp Arg Leu Ser Asp Phe Pro Trp Gly Val Ser Arg
1               5                   10                  15

(2) INFORMATION FOR SEQ ID NO: 126:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 126:

Ser Ser Trp Ile Arg Leu Arg Asp Leu Pro Trp Gly Glu Ser Arg
1               5                   10                  15
```

(2) INFORMATION FOR SEQ ID NO: 127:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 127:

Ser Ser Trp Val Leu Leu Arg Asp Leu Pro Trp Gly Ser Arg
1               5                   10

(2) INFORMATION FOR SEQ ID NO: 128:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 128:

Ser Ser Cys Lys Trp Tyr Glu Lys Cys Ser Gly Leu Trp Ser Arg
1               5                   10                  15

(2) INFORMATION FOR SEQ ID NO: 129:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 129:

Ser Ser Gly Ile Cys Phe Phe Trp Asp Gly Cys Phe Glu Ser Arg
1               5                   10                  15

(2) INFORMATION FOR SEQ ID NO: 130:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 130:

Ser Arg Asn Leu Cys Phe Phe Trp Asp Asp Glu Tyr Cys Ser Arg
1               5                   10                  15

(2) INFORMATION FOR SEQ ID NO: 131:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 131:

His His His Arg His Pro Ala His Pro His Thr Tyr Gly Gly
1               5                   10

(2) INFORMATION FOR SEQ ID NO: 132:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 132:

Ser Arg Ala Gly Leu Leu Ser Asp Leu Leu Glu Gly Lys Ser Arg
1               5                  10                  15

(2) INFORMATION FOR SEQ ID NO: 133:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 133:

Ser Ser Arg Ser Leu Leu Arg Asp Leu Leu Met Val Asp Ser Arg
1               5                  10                  15

(2) INFORMATION FOR SEQ ID NO: 134:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 134:

Ser Ser Asn Lys Leu Leu Tyr Asn Leu Leu Lys Met Glu Ser Arg
1               5                  10                  15

(2) INFORMATION FOR SEQ ID NO: 135:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 135:

Ser Ser Lys Ser Leu Leu Leu Asn Leu Leu Ser Thr Pro Ser Arg
1               5                  10                  15

(2) INFORMATION FOR SEQ ID NO: 136:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 136:

His Ser Phe Pro Pro Glu Ser Leu Leu Val Arg Leu Leu Gln Gly Gly (2) INFORMATION FOR SEQ ID NO: 137:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 137:

Ser Arg Leu Glu Met Leu Leu Arg Ser Glu Thr Asp Phe Ser Arg
1               5                   10                  15

(2) INFORMATION FOR SEQ ID NO: 138:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 138:

Ser Arg Leu Glu Glu Leu Leu Lys Trp Gly Ser Val Thr Ser Arg
1               5                   10                  15

(2) INFORMATION FOR SEQ ID NO: 139:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 139:

Ser Arg Leu Glu Gln Leu Leu Lys Glu Glu Phe Ser Tyr Ser Arg
1               5                   10                  15

(2) INFORMATION FOR SEQ ID NO: 140:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 140:

Ser Arg Leu Glu Gln Leu Leu Arg Ser Glu Pro Asp Phe Ser Arg
1               5                   10                  15

(2) INFORMATION FOR SEQ ID NO: 141:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 141:

```
Ser Arg Leu Glu Asp Leu Leu Arg Ala Pro Phe Thr Thr Ser Arg
1               5                   10                  15
```

(2) INFORMATION FOR SEQ ID NO: 142:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 142:

```
Ser Arg Leu Glu Ser Leu Leu Arg Phe Gly Gln Leu Asp Ser Arg
1               5                   10                  15
```

(2) INFORMATION FOR SEQ ID NO: 143:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 143:

```
Ser Ser Arg Leu Leu Ser Leu Leu Val Gly Asp Phe Asn Ser Arg
1               5                   10                  15
```

(2) INFORMATION FOR SEQ ID NO: 144:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 144:

```
Ser Arg Leu Glu Glu Leu Leu Leu Gly Thr Asn Arg Asp Ser Arg
1               5                   10                  15
```

(2) INFORMATION FOR SEQ ID NO: 145:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 145:

```
Ser Arg Leu Lys Glu Leu Leu Leu Leu Pro Thr Asp Leu Ser Arg
1               5                   10                  15
```

(2) INFORMATION FOR SEQ ID NO: 146:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 146:

```
Ser Arg Leu Glu Cys Leu Leu Glu Gly Arg Leu Asn Glu Cys Ser Arg
1               5                   10                  15
```

(2) INFORMATION FOR SEQ ID NO: 147:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 147:

```
Ser Ser Lys Leu Tyr Cys Leu Leu Asp Glu Ser Tyr Cys Ser Arg
1               5                   10                  15
```

(2) INFORMATION FOR SEQ ID NO: 148:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 148:

```
Ser Arg Leu Ser Cys Leu Leu Met Gly Phe Glu Asp Cys Ser Arg
1               5                   10                  15
```

(2) INFORMATION FOR SEQ ID NO: 149:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 149:

```
Ser Ser Lys Leu Ile Arg Leu Leu Thr Ser Asp Glu Glu Leu Ser Arg
1               5                   10                  15
```

(2) INFORMATION FOR SEQ ID NO: 150:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 150:

```
Ser Ser Arg Leu Met Glu Leu Leu Gln Glu Gly Gln Gly Trp Ser Arg
1               5                   10                  15
```

(2) INFORMATION FOR SEQ ID NO: 151:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 151:

Ser Ser Asn His Gln Ser Ser Arg Leu Ile Glu Leu Leu Ser Arg
1               5                   10                  15

(2) INFORMATION FOR SEQ ID NO: 152:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 152:

Ser Ser Arg Leu Trp Gln Leu Leu Ala Ser Thr Asp Thr Ser Arg
1               5                   10                  15

(2) INFORMATION FOR SEQ ID NO: 153:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 153:

Ser Ser Asn Ser Met Leu Trp Lys Leu Leu Ala Ala Pro Ser Arg
1               5                   10                  15

(2) INFORMATION FOR SEQ ID NO: 154:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 154:

Ser Ser Lys Thr Leu Trp Arg Leu Leu Glu Gly Glu Arg Ser Arg
1               5                   10                  15

(2) INFORMATION FOR SEQ ID NO: 155:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 155:

Ser Arg Ala Gly Pro Val Leu Trp Gly Leu Leu Ser Glu Ser Arg
1               5                   10                  15

(2) INFORMATION FOR SEQ ID NO: 156:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 156:

Ser Ser Leu Thr Ser Arg Asp Phe Gly Ser Trp Tyr Ala Ser Arg
1               5                   10                  15

(2) INFORMATION FOR SEQ ID NO: 157:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 157:

Ser Ser Trp Val Arg Leu Ser Asp Phe Pro Trp Gly Val Ser Arg
1               5                   10                  15

(2) INFORMATION FOR SEQ ID NO: 158:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 158:

Ser Ser Glu Tyr Cys Phe Tyr Trp Asp Ser Ala His Cys Ser Arg
1               5                   10                  15

(2) INFORMATION FOR SEQ ID NO: 159:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 159:

Ser Arg Ser Leu Leu Glu Cys His Leu Met Gly Asn Cys Ser Arg
1               5                   10                  15

(2) INFORMATION FOR SEQ ID NO: 160:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 160:

Ser Ser Glu Leu Leu Arg Trp His Leu Thr Arg Asp Thr Ser Arg
1               5                   10                  15

(2) INFORMATION FOR SEQ ID NO: 161:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 161:

Ser Arg Leu Glu Tyr Trp Leu Lys Trp Glu Pro Gly Pro Ser Arg
1               5                   10                  15

(2) INFORMATION FOR SEQ ID NO: 162:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 162:

Ser Arg Ser Asp Ser Ile Leu Trp Arg Met Leu Ser Glu Ser Arg
1               5                   10                  15

(2) INFORMATION FOR SEQ ID NO: 163:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 163:

Ser Ser Lys Gly Val Leu Trp Arg Met Leu Ala Glu Pro Val Ser Arg
1               5                   10                  15

(2) INFORMATION FOR SEQ ID NO: 164:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 164:

His Ser His Gly Pro Leu Thr Leu Asn Leu Leu Arg Ser Ser Gly Gly
1               5                   10                  15

(2) INFORMATION FOR SEQ ID NO: 165:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 165:

Ser Ser Ala Gly Gly Gly Ala Pro Ala Gly Ser Thr Pro Ser Arg
1               5                   10                  15

(2) INFORMATION FOR SEQ ID NO: 166:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 166:

Ser Ser Tyr Gln Trp Glu Thr His Ser Asp Lys Trp Arg Ser Arg
1               5                   10                  15

(2) INFORMATION FOR SEQ ID NO: 167:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 167:

Ser Ser Val Thr Lys Lys Ala Leu Thr Ile Ala Lys Asp Ser Arg
1               5                   10                  15

(2) INFORMATION FOR SEQ ID NO: 168:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 168:

Glu His Val Cys Ser Trp Gly Trp Gly Arg Cys
1               5                   10

(2) INFORMATION FOR SEQ ID NO: 169:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 169:

Asp Arg Leu Cys Thr Trp Gly Trp Gly Lys Cys
1               5                   10

(2) INFORMATION FOR SEQ ID NO: 170:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 170:

Asn Lys Ile Cys Ala Trp Gly Trp Gly His Cys
1               5                   10

(2) INFORMATION FOR SEQ ID NO: 171:

(i) SEQUENCE CHARACTERISTICS:
            (A) LENGTH: 11 amino acids
            (B) TYPE: amino acid
            (C) STRANDEDNESS: single

```
          (D) TOPOLOGY: linear (ii) MOLECULE TYPE: peptide (xi) SEQUENCE DESCRIPTION: SEQ ID NO: 171:

Gln His Met Cys Gly Trp Gly Trp Gly Arg Cys
1               5                   10

(2) INFORMATION FOR SEQ ID NO: 172:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 172:

Ser Phe Thr Asp Tyr Trp Arg Asp Leu Glu Gln
1               5                   10

(2) INFORMATION FOR SEQ ID NO: 173:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 173:

Pro Gly Trp Trp
1

(2) INFORMATION FOR SEQ ID NO: 174:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 174:

Ser Arg Asp Trp Gly Phe Trp
1               5

(2) INFORMATION FOR SEQ ID NO: 175:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 175:

Ser Arg Glu Trp Gly Phe Trp
1               5

(2) INFORMATION FOR SEQ ID NO: 176:

(i) SEQUENCE CHARACTERISTICS:
          (A) LENGTH: 5 amino acids
          (B) TYPE: amino acid
```

```
        (C) STRANDEDNESS: single
        (D) TOPOLOGY: linear (ii) MOLECULE TYPE: peptide (xi) SEQUENCE DESCRIPTION: SEQ ID NO: 176:

Cys Phe Phe Trp Asp
1               5

(2) INFORMATION FOR SEQ ID NO: 177:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 177:

Leu Xaa Xaa Leu Leu
1               5

(2) INFORMATION FOR SEQ ID NO: 178:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 178:

Asp Leu Tyr Asp Asp Asp Asp Lys
1               5
```

IDENTIFICATION OF DRUG COMPLEMENTARY COMBINATORIAL LIBRARIES

This application is a continuation-in-part of Ser. No. 09/050,359, filed Mar. 31, 1998, which is a continuation-in-part of PCT/US97/19638, filed Oct. 31, 1997, which is a continuation-in-part of Ser. No. 08/740,671, filed Oct. 31, 1996, now abandoned, which applications are hereby incorporated by reference in their entirety.

BACKGROUND OF THE INVENTION

Field of the Invention

This invention relates to methods of identifying drugs which can mediate the biological activity of a target protein.
Protein Binding and Biological Activity Many of the biological activities of the proteins are attributable to their ability to bind specifically to one or more binding partners (ligands), which may themselves be proteins, or other biomolecules.

When the binding partner of a protein is known, it is relatively straightforward to study how the interaction of the binding protein and its binding partner affects biological activity. Moreover, one may screen compounds for the ability of the compound to competitively inhibit the formation of the complex, or to dissociate an already formed complex. Such inhibitors are likely to affect the biological activity of the protein, at least if they can be delivered in vivo to the site of the interaction.

If the binding protein is a receptor, and the binding partner an effector of the biological activity, then the inhibitor will antagonize the biological activity. If the binding partner is one which, through binding, blocks a biological activity, then an inhibitor of that interaction will, in effect, be an agonist.

The residues whose functional groups participate in the ligand-binding interactions together form the ligand binding site, or paratope, of the protein. Similarly, the functional groups of the ligand which participate in these interactions together form the epitope of the ligand.

In the case of a protein, the binding sites are typically relatively small surface patches. The binding characteristics of the protein may often be altered by local modifications at these sites, without denaturing the protein.

While it is possible for a chemical reaction to occur between a functional group on a protein and one on a ligand, resulting in a covalent bond, protein ligand binding normally occurs as a result of the aggregate effects of several noncovalent interactions. Electrostatic interactions include salt bridges, hydrogen bonds, and van der Waals forces.

What is called the hydrophobic interaction is actually the absence of hydrogen bonding between nonpolar groups and water, rather than a favorable interaction between the nonpolar groups themselves. Hydrophobic interactions are important in stabilizing the conformation of a protein and thus indirectly affect ligand binding, although hydrophobic residues are usually buried and thus not part of the binding site.

Peptides have been found to bind proteins at the same sites as those by which the proteins interact with other proteins, macromolecules and biologically significant substances e.g. nucleic acids, lipids and enzyme substrates. The first examples of this property were in the publications of several groups who showed that there is a single peptide binding site on the biotin binding protein streptavidin. This is the same site responsible for biotin binding and these peptides compete with biotin for binding to this site (Biochemistry 34: 15430–15435 (1995) Screening of cyclic peptide phage libraries identifies ligands that bind streptavidin with high affinities, L. B. Giebel, R. T. Cass, D. L. Milligan, D. C. Young, R. Arze & C. R. Johnson; Gene 128: 59–65 (1993) An M13 phage library displaying random 38-amino-acid peptides as a source of novel sequences with affinity to selected targets, B. K. Kay, N. B. Adey, Y. S. He, J. P. Manfredi, A. H. Mataragnon & D. M. Fowlkes; Nature 354: 82–4 (1991) A new type of synthetic peptide library for identifying ligand-binding activity Septou, et al.; Proc Natl Accad Sci USA 92: 5426–5430 (1995) Library of libraries: approach to synthetic combinatorial library design and screening of "pharmacophore" motifs, I. Saggio and R. Laufer; Biochem J 293 (Pt 3): 613–6 (1993) Biotin binders selected from a random peptide library expressed on phage, I. Saggio & R. Laufer). Many other examples exist, for instance Smith demonstrated that peptides displayed on phage which bound to ribonuclease S had a specific consensus motif and that these PLs were antagonistic to ribonuclease activity, implying that the peptides and the RNA were bound by the same ligand binding site (Gene 128: 37–42 (1993) A ribonuclease S-peptide antagonist discovered with a bacteriophage display library, G. P. Smith, D. A. Schultz & J. E. Ladbury). Another example is from the binding of peptide ligands to cell surface integrins (Biochemistry 34: 3948–3955 (1995) Peptide ligands for integrin alpha v beta 3 selected from random phage display libraries, J. M. Healy, O. Murayama, T. Maeda, K. Yoshino, K. Sekiguchi & M. Kikuchi; J Cell Biol 124: 373–80 (1994) Isolation of a highly specific ligand for the alpha 5 beta 1 integrin from a phage display library, E. Koivunen, B. Wang & E. Ruoslahti). Peptides obtained in this way clearly mimic natural protein:protein interactions as in the case for the proteins MDM2 and p53 (Bottger et al. Identification of novel mdm2 binding peptides by phage display, Oncogene, 13:2141–7 (1996)). However, it has not hitherto been appreciated that this phenomenon is sufficiently common so that it might be exploited in identifying inhibitors of the interaction of a protein with an unknowing binding partner. Nor have others explained just how to take advantage of this phenomenon for that purpose.

Traditional Drug Screening

In traditional drug screening, natural products (especially those used in folk remedies) were tested for biological activity. The active ingredients of these products were purified and characterized, and then synthetic analogues of these "drug leads" were designed, prepared and tested for activity. The best of these analogues became the next generation of "drug leads", and new analogs were made and evaluated.

Both natural products and synthetic compounds could be tested for just a single activity, or tested exhaustively for any biological activity of the interest to the tester. Testing was originally carried out in animals, later, less expensive and more convenient model systems, employing isolated organ, tissue, or cell cultures, membrane extracts or purified receptors, were developed for some pharmacological evaluations.

These methods have many disadvantages. Many of these approaches require large amounts of chemical compound to test, especially testing in whole animals and isolated organs. Since the quantity of a given compound within a collection of potential medicinal compounds is limited, this requires one to limit the number of screens executed.

Also, it is inherently difficult to establish structure/activity relationships (SAR) among compounds tested using whole animals, isolated organs and cultured cells. This is because the actual molecular target of any given compound's action may be quite different from that of other compounds scoring positive in the assay. By testing a battery of compounds on a very specific target, one can correlate the action of various chemical residues with the quantitative activity and use that information to focus ones search for active compounds among certain classes of compounds or even direct the synthesis of novel compounds having a composite of the properties shared by the active compounds tested.

Another disadvantage to whole animal, organ and cell based screening is that certain limitations may prevent an active compound from being scored as such. For instance, an inability to pass through the cellular membrane may prevent a potent inhibitor, within a tested compound library, from acting on the activated oncogene ras and giving a spurious negative score in a cell proliferation assay. However, if it were possible to test ras in an isolated system, that potent inhibitor would be scored as a positive compound and contribute to the establishment of a relevant SAR. Subsequent, chemical modifications could then be carried out to optimize the compound structure for membrane permeability.

The overwhelming disadvantage to the receptor based methods for screening compounds is that they require a priori knowledge about the activity of receptor and its biological ligand. If through genetic mapping of a disease loci one determines that a particular gene product is responsible for the disease; and one lacks knowledge about the gene biochemical function because it is not a previously known receptor or enzyme, then it is very difficult to establish an assay with the methods previously known.

The present invention circumvents all these problems.

Combinatorial Libraries

Libraries of thousands, even millions, of random oligopeptides have been prepared by chemical synthesis (Houghten et al., Nature, 354:84–6(1991)), or gene expression (Marks et al., J Mol Biol, 222:581–97(1991)), displayed on chromatographic supports (Lam et al., Nature, 354:82–4 (1991)), inside bacterial cells (Colas et al., Nature, 380:548–550(1996)), on bacterial pili (Lu, Bio/Technology, 13:366–372(1990)), or phage (Smith, Science, 228:1315–7 (1985)), and screened for binding to a variety of targets including antibodies (Valadon et al., J Mol Biol, 261:11–22 (1996)), cellular proteins (Schmitz et al., J Mol Biol, 260:664–677(1996)), viral proteins (Hong and Boulanger, Embo J, 14:4714–4727(1995)), bacterial proteins (Jacobsson and Frykberg, Biotechniques, 18:878–885 (1995)), nucleic acids (Cheng et al., Gene, 171:1–8(1996)), and plastic (Siani et al., J Chem Inf Comput Sci, 34:588–593 (1994))

Libraries of proteins (Ladner, U.S. Pat. No. 5,223,409 (Ser. No. 07/664,989, filed Mar. 1, 1981), peptoids (Simon et al., Proc Natl Acad Sci USA, 89:9367–71(1992)), nucleic acids (Ellington and Szobtak, Nature, 246:818(1990)), carbohydrates, and small organic molecules (Eichler et al., Med Res Rev, 15:481–96(1995)) have also been prepared or suggested for drug screening purposes.

Sparks, et al., Nature Biotechnology, 14:741 (June 1996) used an SH3 domain-binding peptide isolated from a phage-displayed random peptide library to screen a 16-day mouse embryo cDNA expression library for proteins with SH3-domains. This process is referred to as "COLT" (cloning of ligand targets). These proteins, some of which were not previously known, may then be used as binding targets in screening peptide libraries for additional SH3-domain-binding ligands.

The chemistry of peptide libraries is quite similar to many of the natural macromolecules involved in biological processes and thus these libraries are rich in structures that mimic the natural ones which interact with the target protein. In addition, the variants are composed of linear polymers such that each actually represents a sliding window of many differing chemical constituents. For instance, if a given macromolecular interaction is based on the side chains of four amino acids within a binding peptide, then a 13 amino acid peptide has 10 potential combinations of residues which may bind; therefore a library of $10^8$ members has about $10^9$ 4-mer permutations. This, combined with ease of producing and screening exceptionally large and diverse peptide libraries, provides the incentive to use peptide combinatorial libraries for the initial identification and probing of protein functional domains.

Unfortunately, peptides per se have limited utility for use as therapeutic entities. They are costly to synthesize, unstable in the presence of proteases and in general do not transit cellular membranes. Other classes of compounds have better properties for drug candidates. However, historically, acquiring chemical compound libraries has been a barrier to the entry of smaller firms into the drug discovery arena. Due to the large quantity of chemical required for testing on whole animals and even on cells in culture, it was a given that whenever a compound was synthesized it should be done in fairly large quantity. Thus, there was a synthesis and purification throughput of less than 50 compounds per chemist per year. Large companies maintained their immensely valuable collections as trade barriers. However, with the downsizing of targets to the molecular level and the automation of screens, the quantity of a given compound necessary for an assay has been reduced to very small amounts. These changes have opened the door for the utilization of so-called combinatorial chemistry libraries in lieu of the traditional chemical libraries. Combinatorial chemistry permits the rapid and relatively inexpensive synthesis of large numbers of compounds in the small quantities suitable for automated assays directed at molecular targets. Numerous small companies and academic laboratories have successfully engineered combinatorial chemical libraries with a significant range of diversity (reviewed in Doyle, 1995, Gordon et al, 1994a, Gordon et al, 1994b).

We have developed a systematic means for development of drug discovery screens for numerous targets. One of the special advantages of this system is that the high throughput screens are essentially identical for similar and dissimilar targets, bypassing the need to develop distinct assays for biochemically diverse targets. This is desirable for several reasons. First and foremost, one is never certain how useful a specific target is for therapeutic intervention. It is not until active compounds have been isolated and tested that one can truly "validate" a molecular target. Thus it makes sense to chose as many targets as practical, establish screens for each and then validate each target pharmacologically using the identified compounds. Second, for many potential targets one may not be aware of a biochemical activity that can be used to establish molecular assays. Many potential targets can be proposed based upon the results of genetic experimentation rather than biochemical data. This has been the case for viruses due to ease of subcloning and mutagenic analysis and, now, with the outpouring of human genetic data, shall be true in many other disease areas. The challenge is to go from genetic data to development of useful drug screens.

DGI Technologies, WO96/04557 corresponding to Blume, U.S. Pat. No. 6,010,861, "Target Specific Screens and Their Use for Discovering Small Organic Molecular Pharmacophores", suggests first screening a library composed of mutated variable domains of antibodies (V-H, V-L, or single chain antibodies, which are V-H and V-L domains joined by a peptide linker) for domains which bind the target. Preferably, the parental variable domains have a solved 3D structure (p. 44).

The targets of principal interest to DGI are cell-surface receptors (pp. 149–50). They speculate that an antibody library will survey the entire surface of the target (pp. 5, 39). They are particularly interested in finding antibodies which bind a target receptor protein at a site other than the receptor's endogenous ligand binding site (p. 4).

The antibodies of interest to DGI are those which are both T+ (bind the target) and A+ (activate the target, or are capable of activating the target when combined with another ligand) (pp. 42, 14).

DGI prefers to sequence the T+A+ antibodies, predict their 3D structure on the basis of the known structure of the parental antibody, and design small organic pharmaccphores which mimic the binding conformation of the CDRs of the antibody (pp. 78–91). However, it does contemplate that one could use labeled T+A+ antibodies in competitive binding assays to screen "chemical libraries" for binding activity (pp. 91–93, 42). The chemical libraries contemplated are the kind available from Alldrich and Kodak (p. 12), which are not combinatorial libraries. That is, they are merely accretive collections of biologically active compounds. While some compounds may be related, because they came from a single research program, the collection as a whole is a hodgepodge.

All references, including any patents or patent applications, cited in this specification are hereby incorporated by reference. No admission is made that any reference constitutes prior art. The discussion of the references states what their authors assert and applicants reserve the right to challenge the accuracy and pertinency of the cited documents.

SUMMARY OF THE INVENTION

The present invention relates to a method of identifying drugs which can mediate the biological activity of a target protein via inhibition of binding of the target protein to a binding partner. Unlike prior methods, it does not require that the natural binding partner be used as a reagent, or even that it have been characterized. The need for the natural binding partner is obviated by the use of complementary combinatorial libraries.

Applicants screen a first combinatorial library for binding to the target protein. Preferably, this library is a biopolymer library, and, more preferably, an amplifiable library. Applicants then screen a second (complementary) library (preferably combinatorial in nature) for the ability to inhibit the binding of one or more of the target binding ligands in the first library to the target protein. The members of this library are typically small organic compounds, and more suitable as drugs or drug leads than the compounds of the first library.

The successful inhibitors are candidate antagonists of one or more of the biological activities of the target protein.

Applicants believe that those members of a combinatorial library, especially a biopolymer library, which bind to a target protein having a biologically significant binding activity will bind preferentially to the sites at which the target protein interacts with the natural binding partners which mediate its biological activity, as opposed to randomly, with equal probability, over the entire surface of the target protein. If so, then the target-binding members of the library in question can be used as surrogates for an unknown or unavailable natural binding partner in screening a second combinatorial library (the "complementary library"), which need not be a biopolymeric library, for members which can inhibit the complexing of target protein to its natural binding partner. The surrogate library is preferably an amplifiable (peptide or nucleic acid) library.

The active sites of proteins, by which they interact with other molecules, may consist of one or more concavities (depressions) and/or convexities (protuberances) on the surface of the protein. Generally speaking, oligopeptides, oligonucleotides, and other small organic molecules, are most likely to bind to a protein by fitting, in whole or in part, into a concavity on the surface of the protein.

Preferably, the peptides of the first library are of 5–50 amino acids. Peptides of at least five amino acids length are sufficiently large to bind to an active site with a reasonably high activity. Peptides larger than about 50 amino acids are generally too large to fit into an active site, and also are more cumbersome to synthesize.

The surrogate peptides of the present invention are superior to antibodies for use as surrogate ligands in the identification of pharmaceutically useful small organic compounds. Structural data from diverse sources indicate that the binding sites of antibodies are deep pockets in the surface of antibodies, and are therefore are less suitable than oligopeptides for binding to concavities on the surface of targets. Such concavities are the probable binding sites of small ligands.

Unlike peptide ligands, antibodies do not appear to discriminate the endogenous ligand binding sites from the remainder of a target protein. Hence, they are a poor choice for a surrogate ligand.

For the foregoing reasons, when the first combinatorial library is composed of peptides, the peptides do not comprise an antibody-like domain. Thus, the peptides cannot be antibodies, single chain antibodies, or isolated variable heavy or light domains thereof. This exclusion applies both to naturally occurring antibodies, and to mutant antibodies which retain the normal structure of an antibody variable domain. The term "antibody-like domain" refers to a peptide having the normal structure of an antibody variable domain, as defined at col. 15, lines 59–68 of Ladner, U.S. Pat. No. 5,403,484.

The term "library" generally refers to a collection of chemical or biological entities which can be screened simultaneously for a property of interest. (They may be screened sequentially, if desired, but simultaneous screening is more efficient.) Typically, they are related in origin, structure, and/or function.

The term "combinatorial library" refers to a library in which the individual members are either systematic or random combinations of a limited set of basic elements, the properties of each member being dependent on the choice and location of the elements incorporated into it. Typically, the members of the library are at least capable of being screened simultaneously. Randomization may be complete or partial; some positions may be randomized and others predetermined, and at random positions, the choices may be limited in a predetermined manner. The members of a combinatorial library may be oligomers or polymers of some kind, in which the variation occurs through the choice of monomeric building block at one or more positions of the oligomer or polymer, and possibly in terms of the connecting linkage, or the length of the oligomer or polymer, too. Or the members may be nonoligomeric molecules with a standard core structure, like the 1,4-benzodiazepine structure, with the variation being introduced by the choice of substituents at particular variable sites on the core structure.

The ability of one or more members of such a library to recognize a target molecule is termed "Combinatorial Recognition".

In a "simple combinatorial library", all of the members belong to the same class of compounds (e.g., peptides) and can be synthesized simultaneously. A "composite combinatorial library" is a mixture of two or more simple libraries, e.g., DNAs and peptides. The number of component simple libraries in a composite library will, of course, normally be smaller than the average number of members in each simple library, as otherwise the advantage of a library over individual synthesis is small.

A biased combinatorial library is one in which, at one or more positions in the library member, only one of the possible basic elements is allowed for all members of the library, i.e., the biased positions are invariant.

The term "amplifiable combinatorial library" refers to a library in which the individual members, after found to bind to a target, may be amplified in vivo or in vitro, using elements already present in the library as starting materials. There are two classes of amplifiable members. First, nucleic acids may be amplified in vivo through natural replicative processes, or in vitro through techniques such as polymerase chain reaction (PCR). Second, peptides, when presented on phage, or otherwise associated with an encoding nucleic acid, may be amplified indirectly by in vivo or in vitro amplification of the associated nucleic acid encoding the peptide, the amplified nucleic acid being expressed to produce the peptide.

The term "biopolymeric library" refers to a library composed of peptides (together with peptoids), nucleic acids, and/or oligosaccharides. (It is not necessary that they be composed of naturally occurring amino acids, bases, or sugars, respectively.) However, because of the greater complexity of carbohydrate synthesis, peptides and nucleic acids are of greater interest.

A "panel of combinatorial libraries" is a collection of different (although possibly overlapping) and separately screenable simple or composite combinatorial libraries. A "panel" differs from a composite library in that the component simple libraries have not been mixed together, that is, they may still be screened separately.

A "structural panel" is a panel as defined above where there is some structural relationship between the member libraries. For example, one could have a panel of 20 different biased peptide libraries where, in each library, the middle residue is held constant as a given amino acid, but, in each library the constant residue is different, so, collectively, all 20 possible genetically encoded amino acids are explored by the panel.

A "scanning residue library" refers to the preparation of panel of biased combinatorial peptide libraries such that the position of the constant residue shifts from one library to the next. For example, in library 1, residue 1 is held constant as a particular residue AA, in library, residue 2 is, and so forth through two or more (usually all) positions of the peptide.

One may have structured panels of libraries in which one may define subpanels, too. For example, in one subpanel, the middle residue $AA_1$ may be the same for all libraries, but the libraries also have a constant residue $AA_2$ which is scanned through all other residue positions.

A library screening program is a program in which one or more libraries (e.g., a structured panel of biased peptide libraries) are screened for activity. The libraries may be screened in parallel, in series, or both. In serial screening, the results of one screening may be used to guide the design of a subsequent library in the series.

The size of a library is the total number of molecules in it, whether they be the same or different. The diversity of a library as the number of different molecules in it. "Diversity" does not measure how different the structures of the library; the degree of difference between two structures is referred to here as "disparity" or "dispersion". The "disparity" is quantifiable in some respects, e.g., size, hydrophilicity, polarity, thermostability, etc. The average sampling frequency of a library is the ratio of size to diversity. The sampling frequency should be over the detection limit of the assay in order to assure that all members are screened.

The combinatorial libraries usually will have a diversity of at least $10^3$ different structures. Preferably, the initial, surrogate-generating library is of high diversity, e.g., preferably at least about $10^6$, more preferably at least about $10^9$ different members. While a peptide library is preferred, a library composed of a different class of compounds (e.g., peptoids or nucleic acids) is acceptable if there would be a detectable preference for binding the activity-mediating binding sites of the target protein.

The complementary library need not be, and preferably is not, a peptide library and it may be of lower overall diversity. It may be screened against all of the surrogate peptides; or only against selected ones. The screenings may be individual or collective. Often, the members of the complementary library will be less specific in their binding to the paratopes of the target protein than are the members of the first library, possibly because their surface area is smaller and offers fewer opportunities for favorable (or unfavorable) interactions with other molecules. A preferred complementary library is a benzodiazepine library.

The degree of complex-inhibitory activity of the members of the complementary library may be quantified by means of a labeled surrogate peptide and an insolubilized target protein. Either the amount of labeled surrogate peptide is fixed, and the amount of complementary compound varied, or, more preferably, the amount of labeled surrogate peptide is varied and the amount of complementary compound held constant. The greater the activity of the complementary compound, the less labeled surrogate peptide will be in the solid phase (i.e., complexed to the target protein) and the more will be in the liquid phase (i.e., uncomplexed). The amount of label in either phase is then measured and correlated with the amount of the variable component. Conventional method of screening libraries for binding molecules do not lend themselves to quantification of the degree of affinity.

It is possible that some of the target protein binding members of the first library will not bind the target protein at the site bound by the natural binding partner which mediates the biological activity of interest, or bind it that site but still do not have an effect similar to that of the natural binding partner, i.e., that these nominal surrogates are not true surrogates for the natural binding partner. However, as long as one or more of the identified members are true surrogates, if all of the nominal surrogates are used in screening the complementary library, then one necessarily will screen for inhibitors of the binding of the true surrogates to the target protein, too.

To reduce the number of "false hits" generated (i.e., compounds which inhibit the binding of a false surrogate to the target protein, or which inhibit binding of a true surrogate but at the wrong site), one may first test the nominal surrogates in a suitable biological system, for the ability to interact with the target protein so as to mediate its biological activity of interest (or at least a related activity that is evaluatable in that biological system). Then only those nominal surrogates which are active in this model system are used in screening the complementary library.

It is expected that most of the compounds of the complementary library which inhibit the complexing of the surrogate peptide to the target protein will achieve this inhibition by binding to the target protein in such a manner as to block its interaction with the surrogate peptide. While it is theoretically possible that the complementary compound will bind to the surrogate peptide instead of the target protein, this interaction is likely to be weak, since most oligopeptides do not have a stable conformation.

It is, of course, a simple matter to distinguish inhibitory compounds which bind the target protein from those which bind the surrogate peptide by use of either the target protein or surrogate peptide alone, in labeled or immobilized form, as an assay or affinity separation reagent.

For each of 16 targets, the sequences of the binding peptides identified by screening phage display libraries were analyzed First, for peptides binding a given target, a consensus sequence was determined, and from this, a core binding region. The amino acids in the core region of all the peptides binding that target were tallied, and the tallies were divided by the number of peptides in question, to obtain a subtotal for each target. The target subtotals were then added and divided by the number of targets. The final totals were converted into percentages. If all of the residues were represented equally their values would be 5%.

Figure 3:
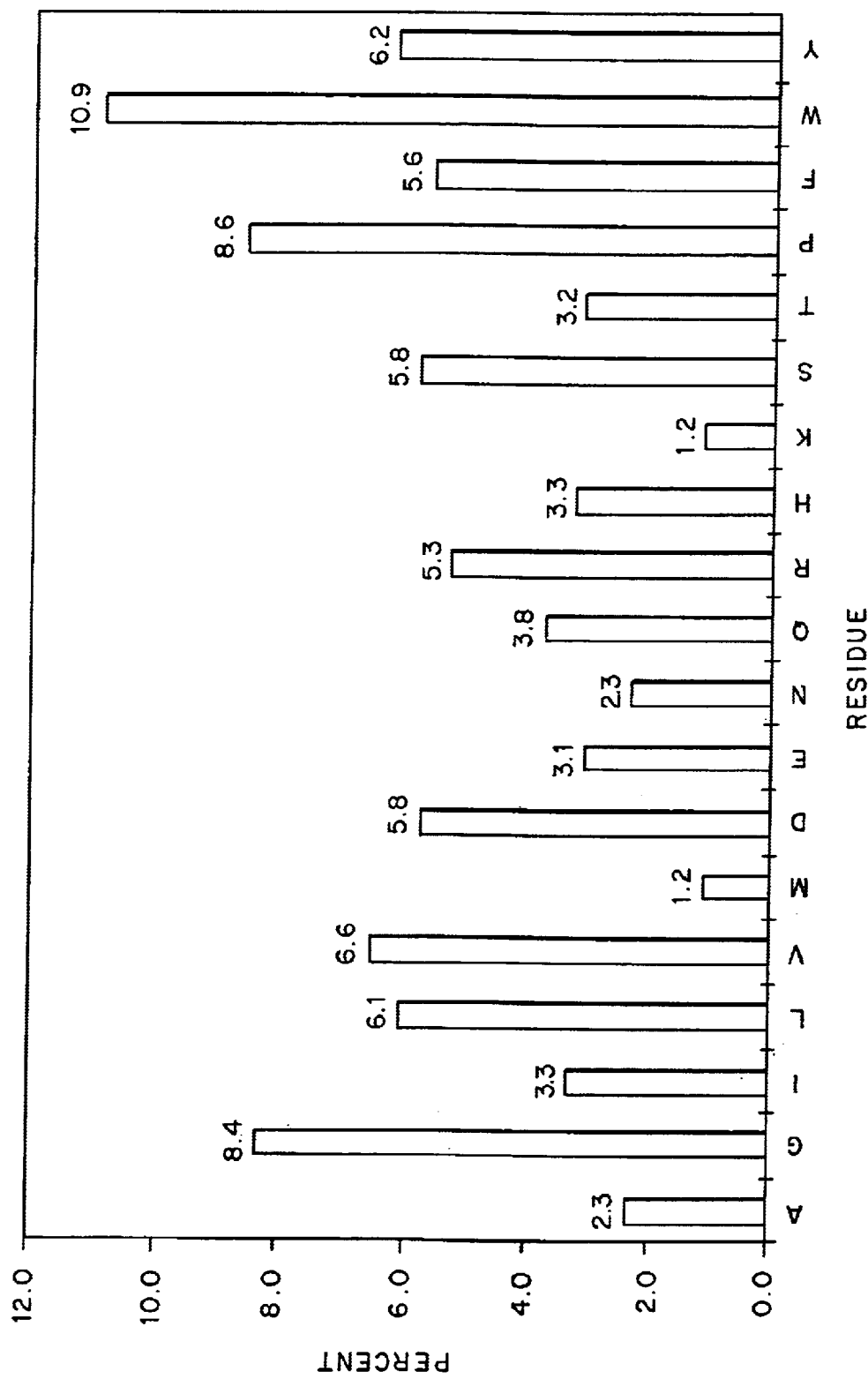
FIG. 3. Occurrence of Amino Acids (AA) in Binding Peptides Identified by screening from Phage Display Libraries.
Figure 4:
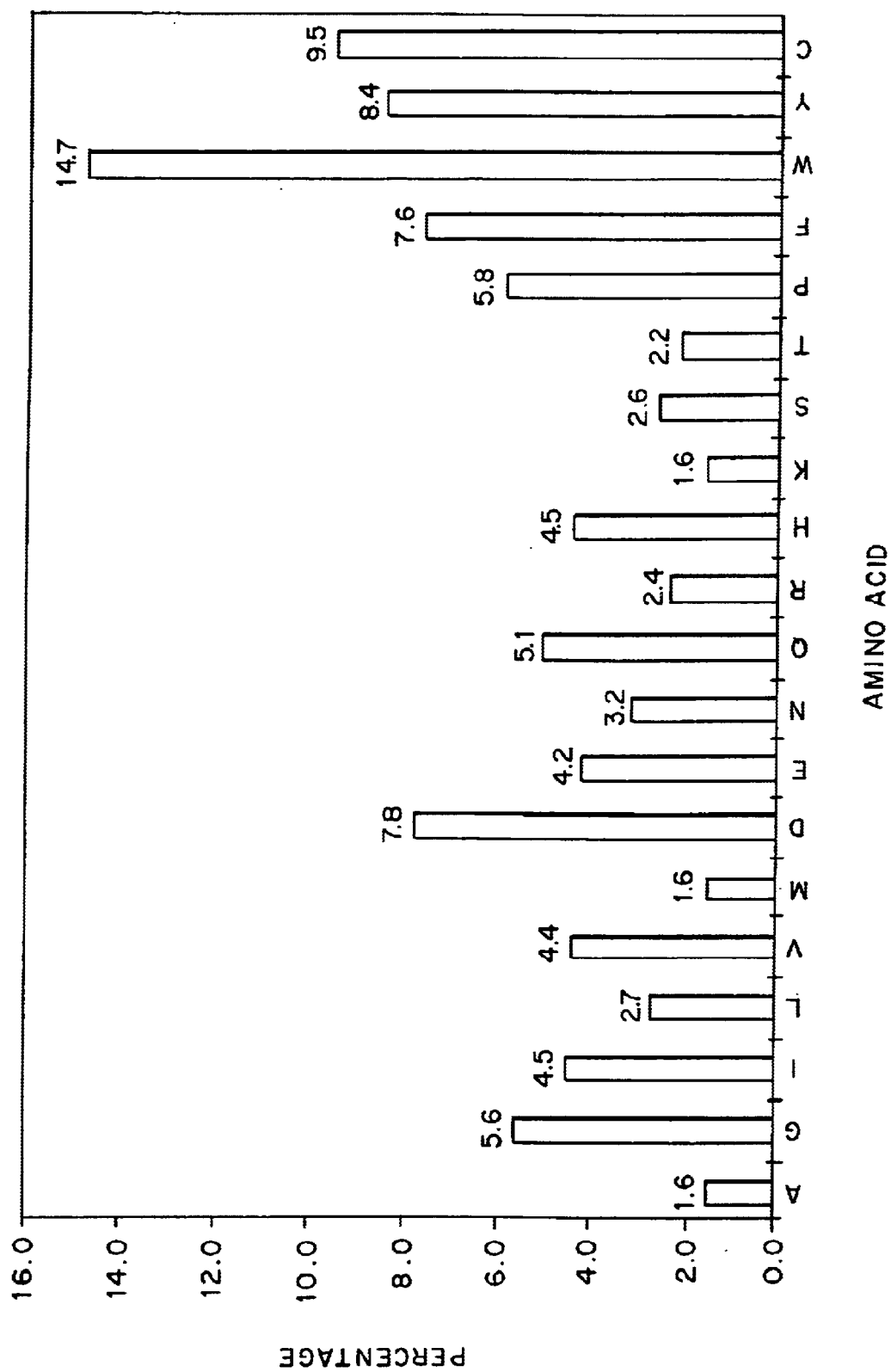

FIG. 4. Occurrence of amino acid residues in binding peptides identified by screening phage display libraries, after correcting for codon usage. The numbers in FIG. 3 were divided by the number of codons available for each residue using an NNK coding scheme and the resulting numbers normalized to 100%.

Figure 5:
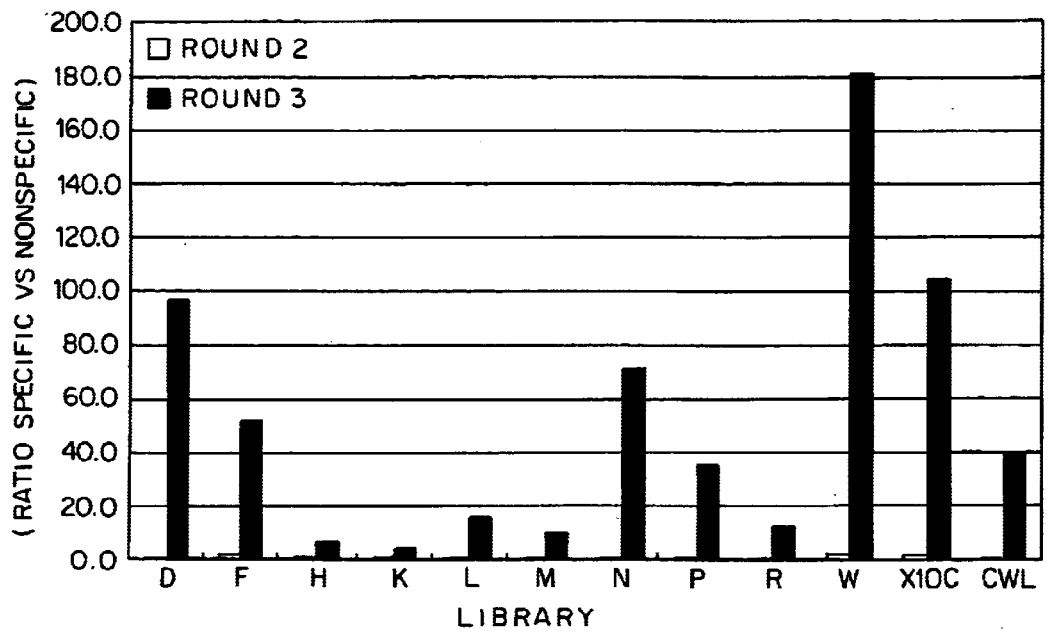

FIG. 5. Enrichment of Phage Binding to CMV UL44. The proportion of phage binding to UL44 was monitored after 2 and three rounds of selection as described in the text. The ratio represents the number of blue plaques/# of white plaques. The library letters represent the residue held constant in each library.

Figure 6:
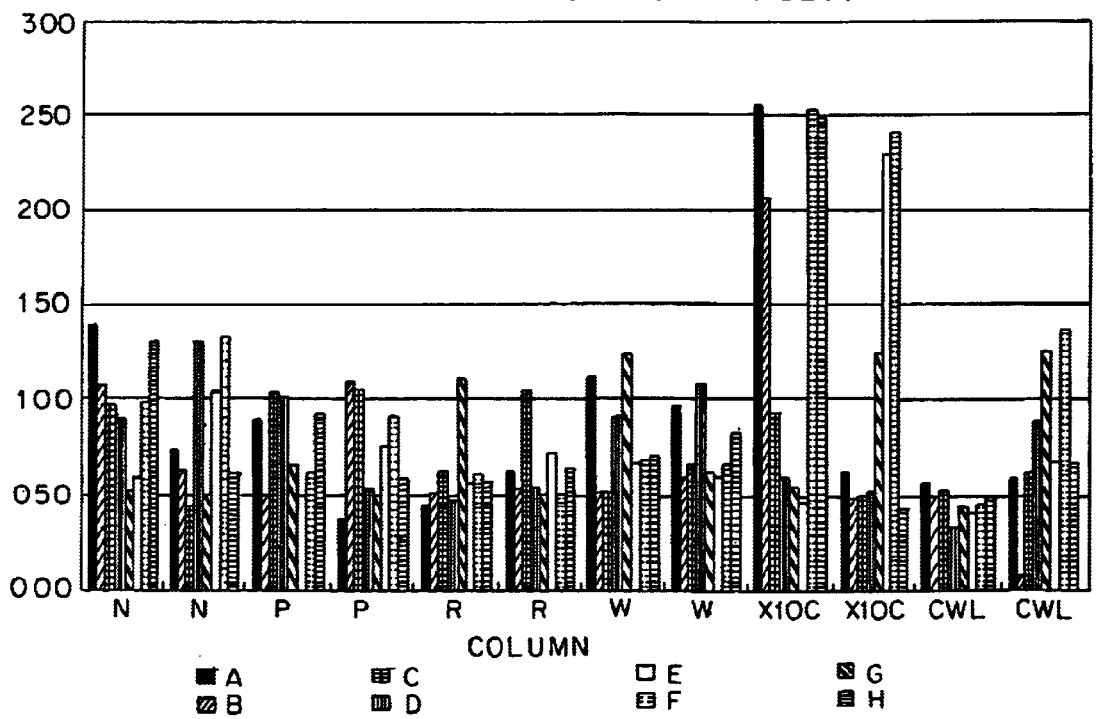

FIG. 6. Individual phage ELISAs for CMV UL44. Individual clones were picked after three rounds of selection on UL44 and tested for binding in a phage ELISA format. Letters under the graph represent the libraries that individual clones were isolated from. Letters A-H in the legend represent the row designation on the microtiter plate.

Figure 7A:
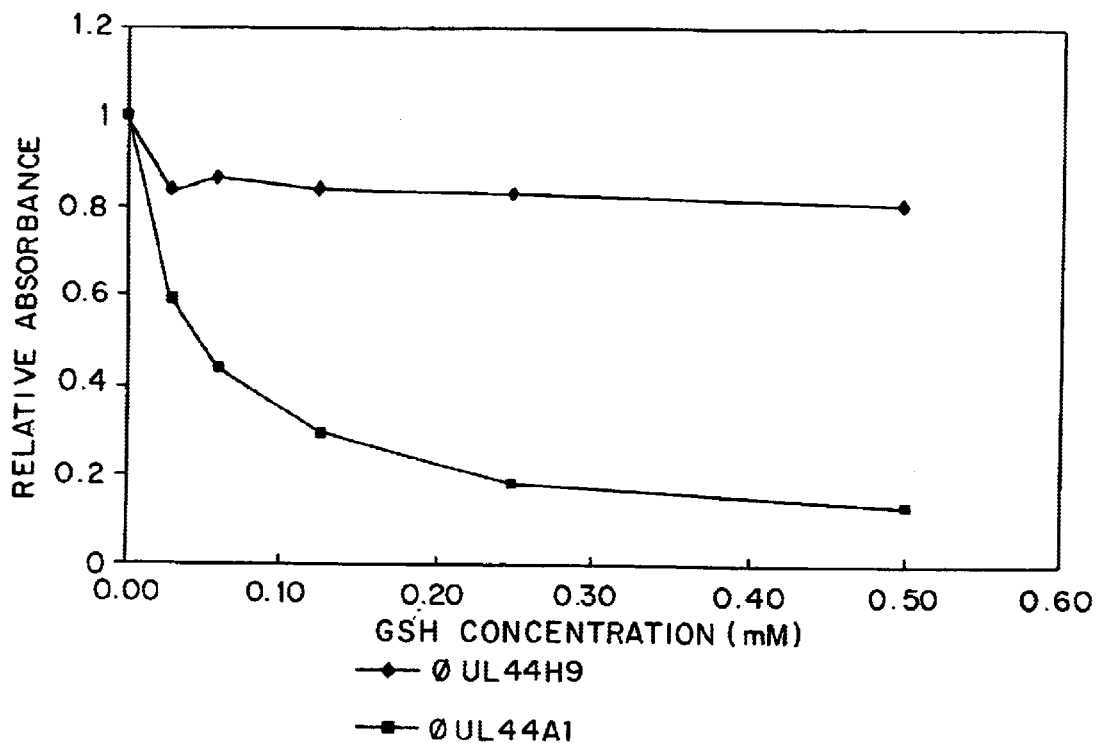
Figure 7B:
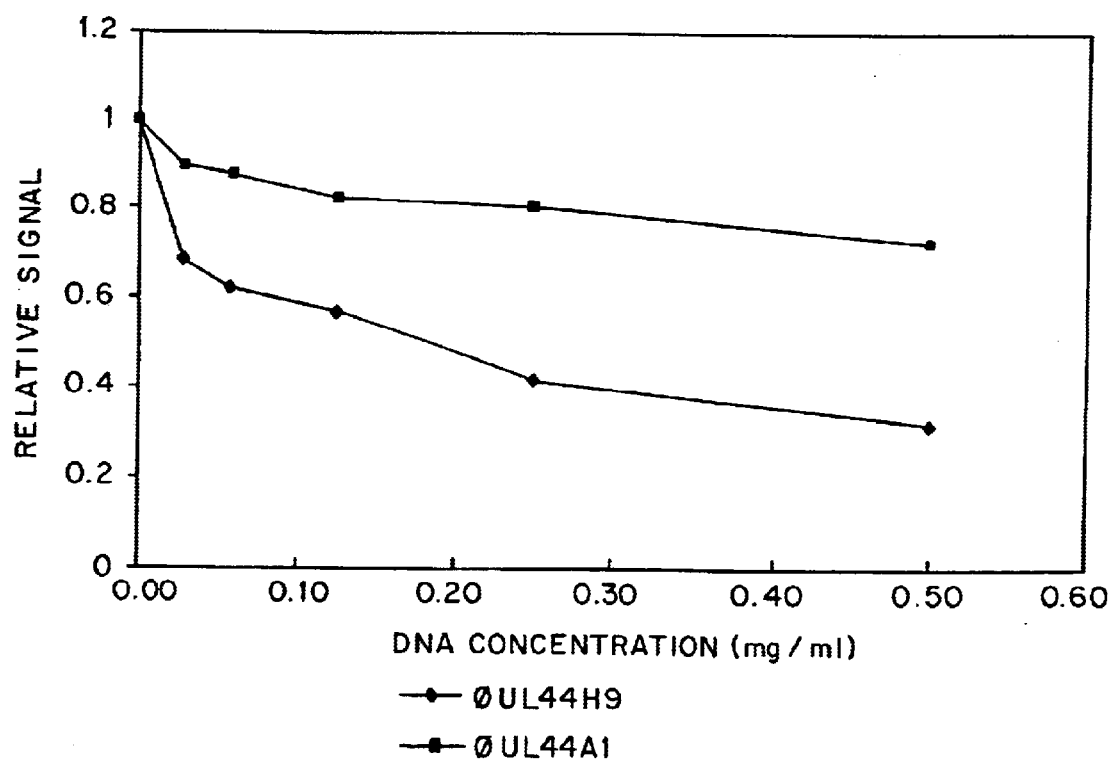

FIG. 7. Competition for binding between phage and substrates. Competitive binding experiments were carried out as described in the text using GSTUL44 immobilized on plates as a target. Various concentrations of (a) glutathione (FIGS. 7a) or (b) DNA (FIG. 7b) was added to each well and the binding of phage was monitored using a phage ELISA. Square boxes represent phage which bind to the GST portion of the fusion and diamonds represent phage which bind to the UL44 portion of the fusion protein.

Figure 8:
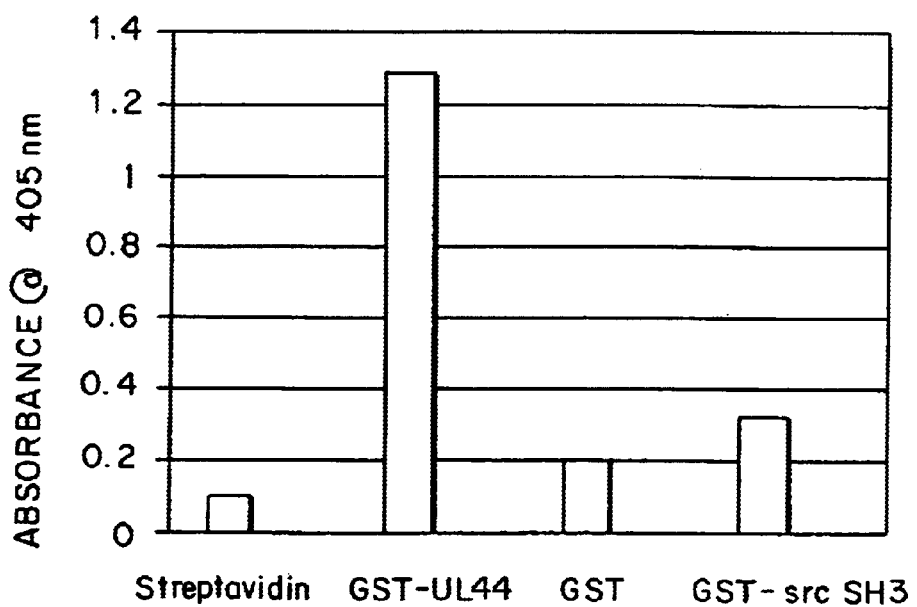

FIG. 8. ELS Assay of UL44 BioKey (surrogate ligand). The peptide isolated from affinity selection against UL44 was synthesized and tested for specific binding as described in the text. (ELS=Enzyme Linked Spectrophometric). The targets tested were streptavidin, GST-UL44, GST, and GST-src SH3. The amount of biotinylated peptide binding was monitored using a streptavidin-HRP conjugate.

Figure 9:
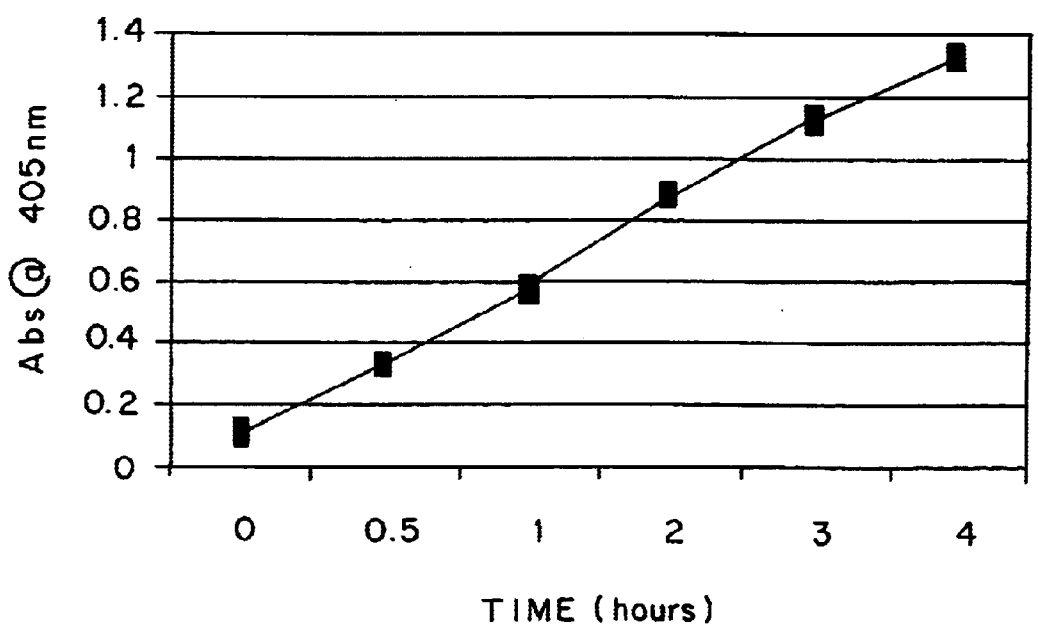

FIG. 9. Time Course of 50 pmol UL44 BioKey (surrogate ligand) Binding to GST-UL44. The binding of the UL44 Surrogate ligand was monitored as a function of time. The signal increases in a linear fashion for at least 4 hours.

Figure 10:
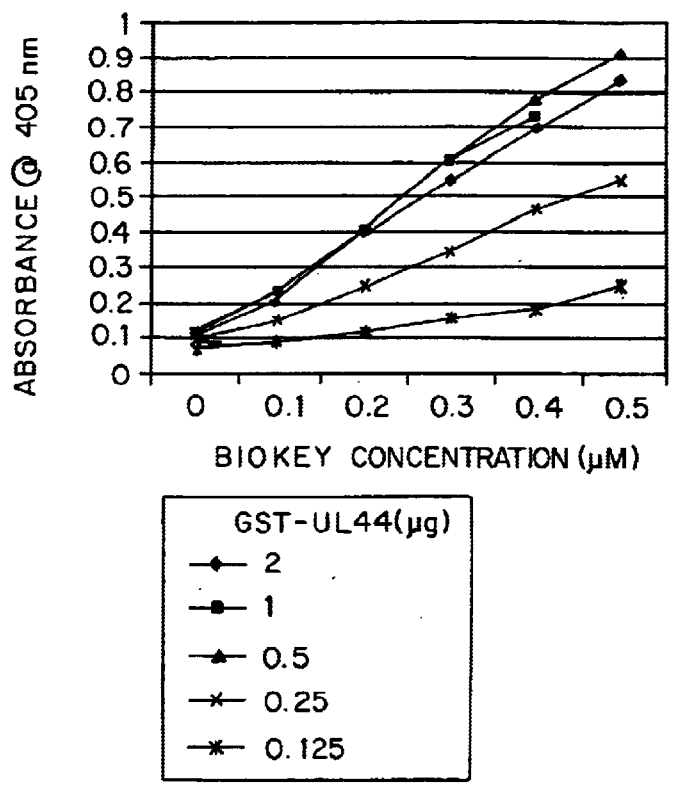

FIG. 10. Titration Curves for Binding of UL44 BioKey (surrogate ligand) to GST-UL44. The binding of biotinylated peptide was monitored as a function of target concentration immobilized on the plate (from 0.125 migrograms to 2 micrograms) and as a function of peptide concentration (from 0.1 to 0.5 micrograms).

Figure 11:
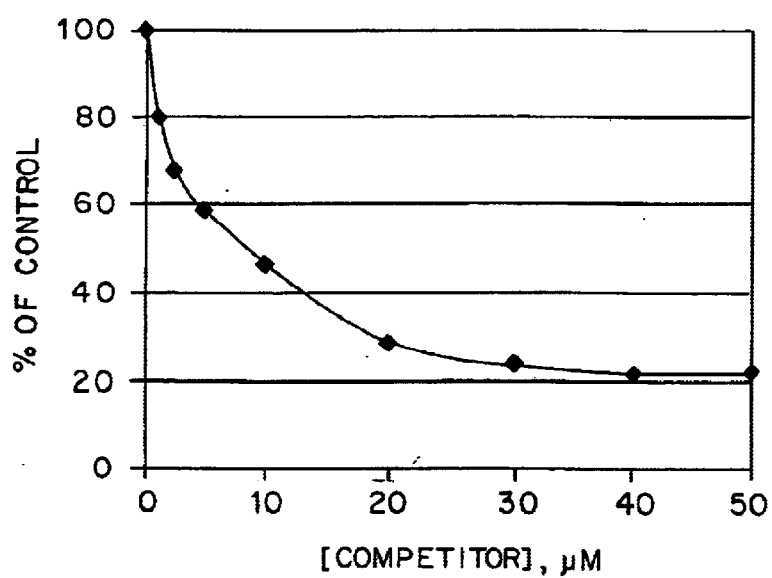

FIG. 11. UL44 BioKey (surrogate ligand): Self-Competition between biotinylated UL44 surrogate ligand and non-biotinylated surrogate ligand was determined. Competitor is the concentration on non-biotinylated UL44 peptide added. The signals are presented as a percent of binding compared to no inhibitor added.

Figure 12:
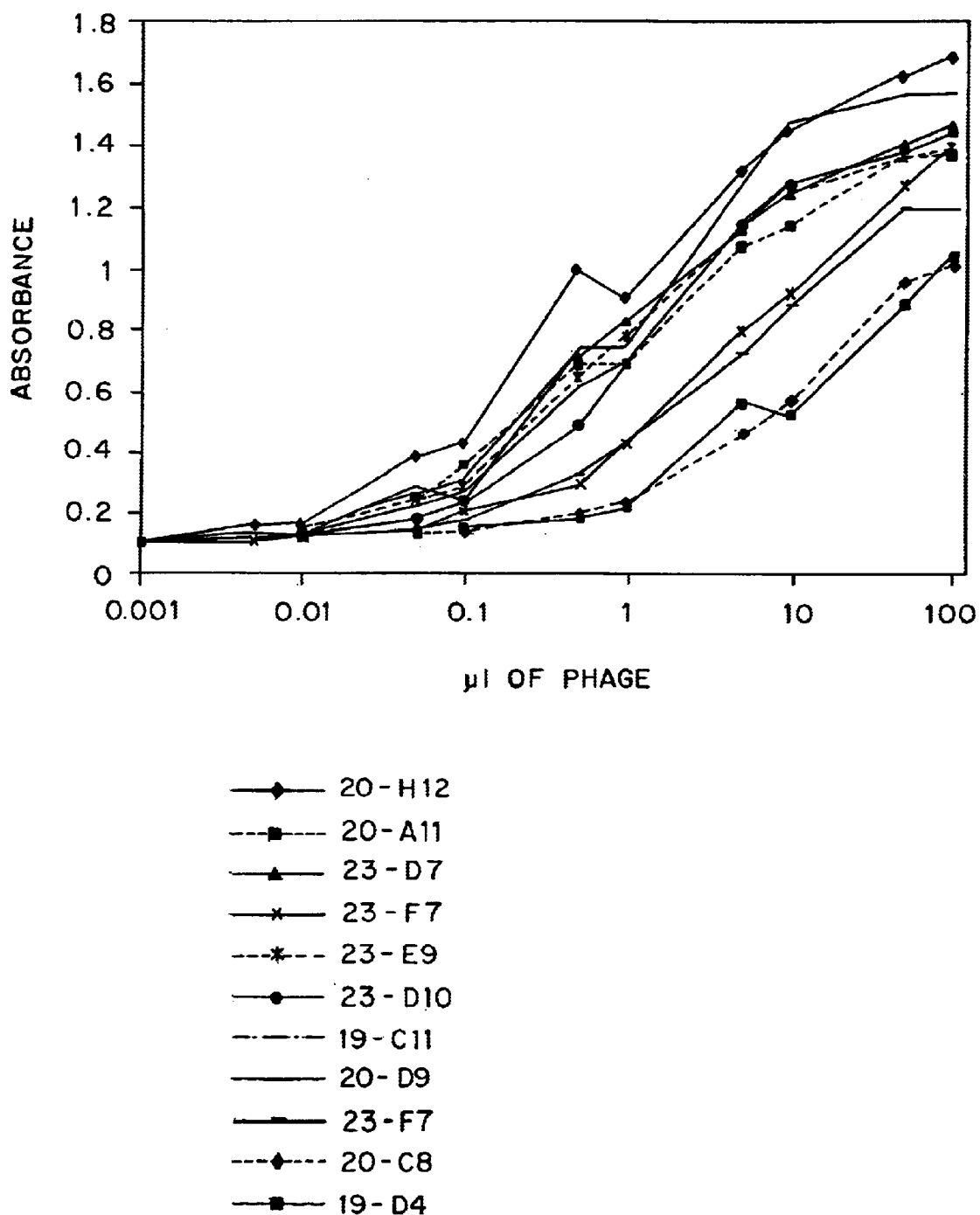

FIG. 12. Titration of PKC binding phage. A serial dilution of phage were incubated with immobilized PKC and the amount of phage binding monitored using a phage ELISA.

Figure 13A:
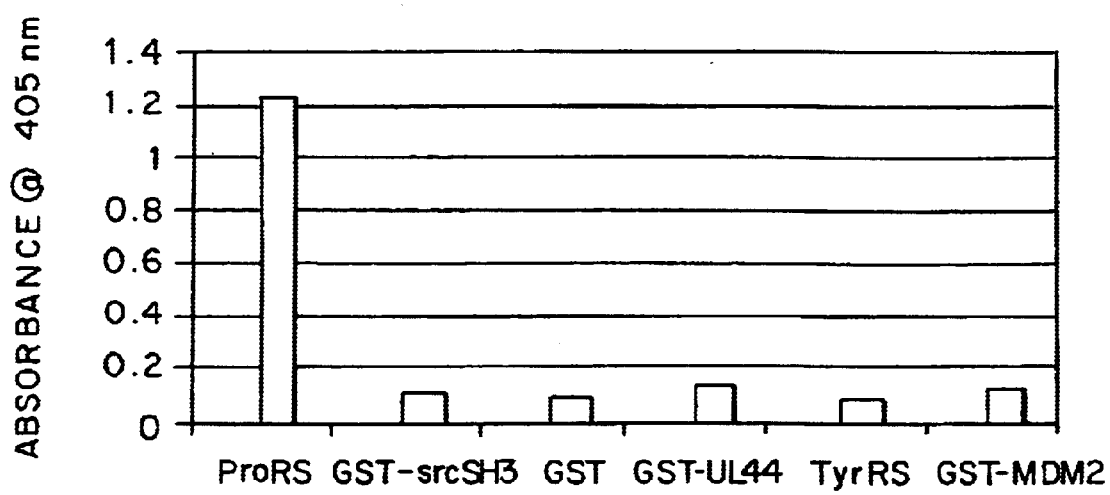
Figure 13B:
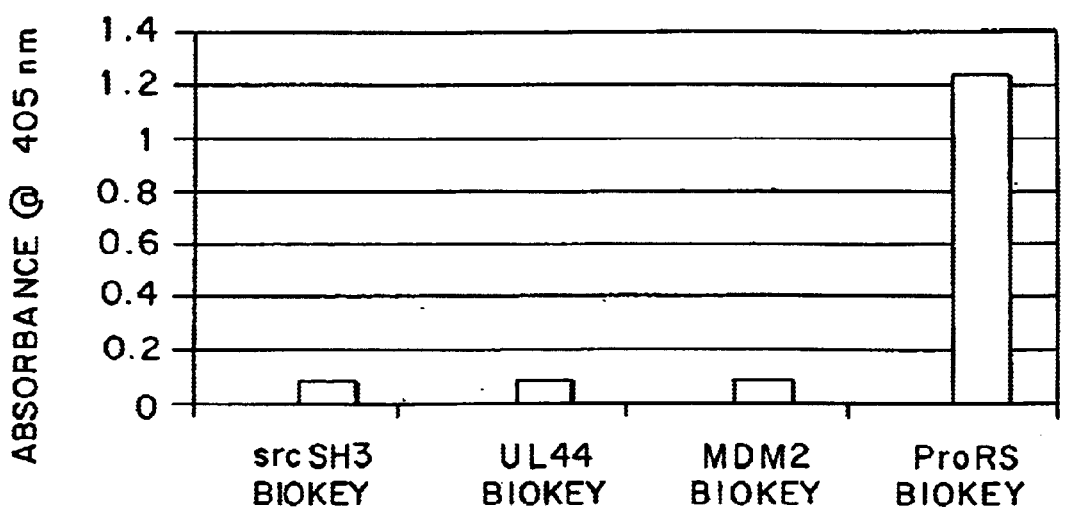

FIG. 13a. Specific Binding of the ProRS BioKey (surrogate ligand). (a) The peptide isolated from affinity selection against ProRS was synthesized and tested for specific binding as described in the text. The targets tested were ProRS, GST-src SH3, GST, GST-UL44, TyrRS and GST-MDM2. The amount of biotinylated peptide binding was monitored using a streptavidin-HRP conjugate. FIG. 13b BioKeys (Surrogate ligands) for other targets do not bind to ProRS. Surrogate ligands for src SH3, UL44, and MDM2 were tested for binding to ProRS as described in the text.

Figure 14A:
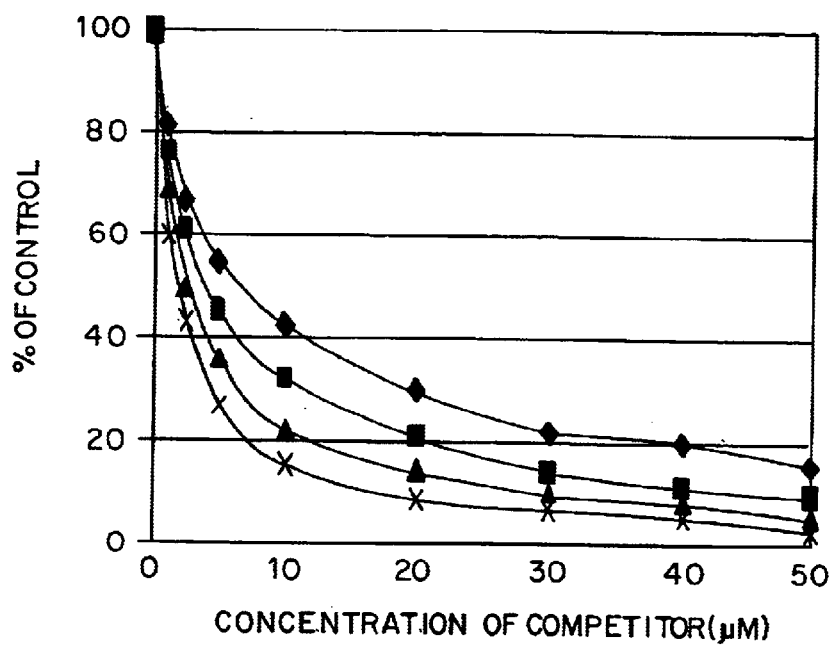
Figure 14B:
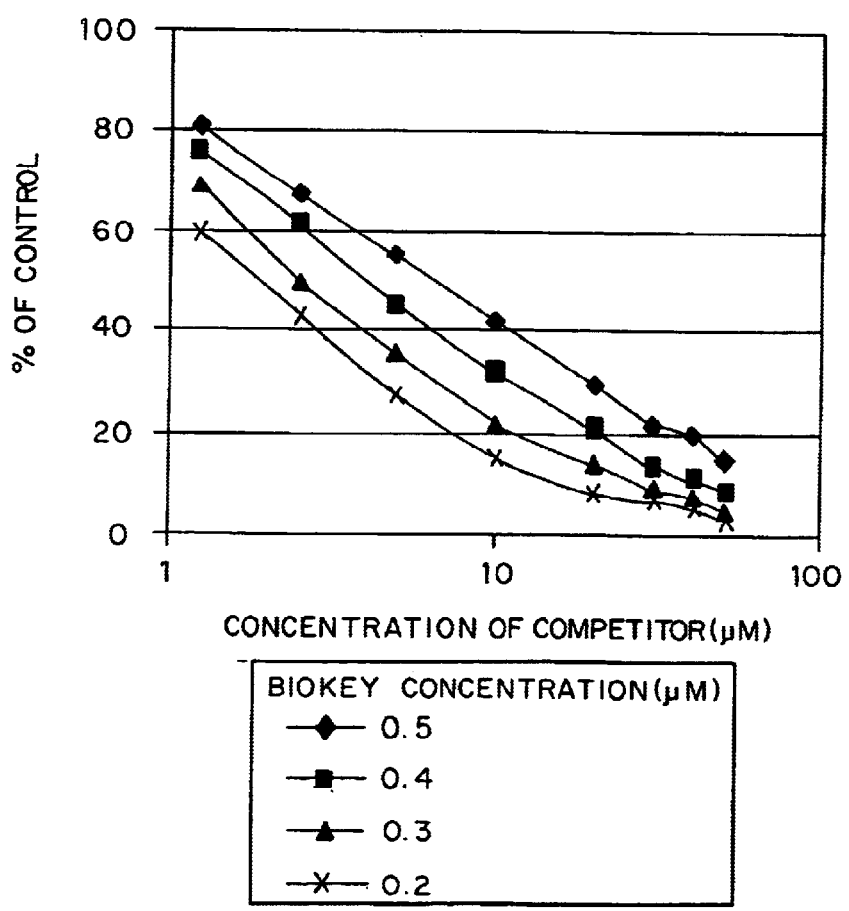

FIG. 14. Self competition for ProRs BioKey. Self-Competition between biotinylated ProRS surrogate ligand and non-biotinylated surrogate ligand was determined. Competitor is the concentration on non-biotinylated ProRS peptide added. BioKey concentration is the concentration of biotinylated ProRS surrogate ligand used. The signals are presented as a percent of binding compared to no inhibitor added and are graphed in two formats: (a) linear (FIGS. 14a) and (b) log (FIG. 14b) scales of the competitor concentrations.

Figure 15A:
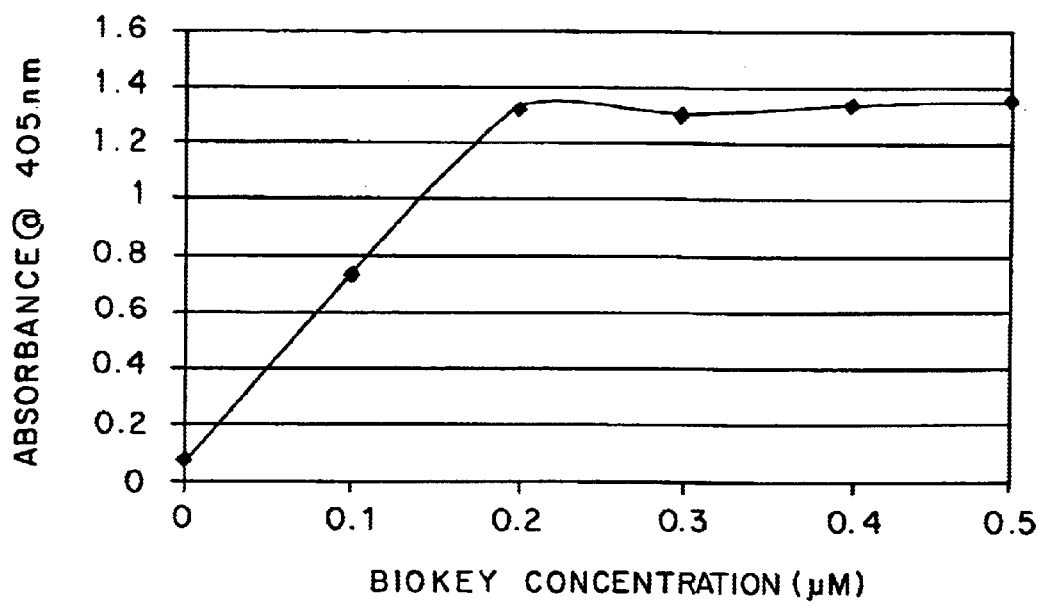
Figure 15B:
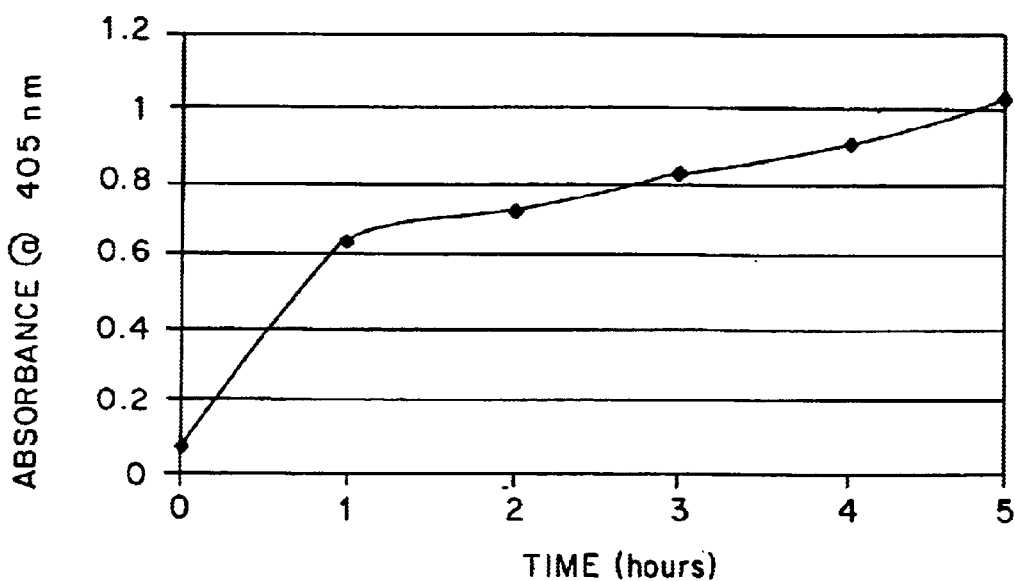

FIG. 15. Concentration and time dependence of ProRS surrogate ligand binding. (a) The binding of biotinylated peptide was monitored as a function of peptide concentration (from 0.1 to 0.5 micrograms) (FIG. 15a). (b) The binding of biotinylated peptide was monitored as a function of time (FIG. 15b).

Figure 16:
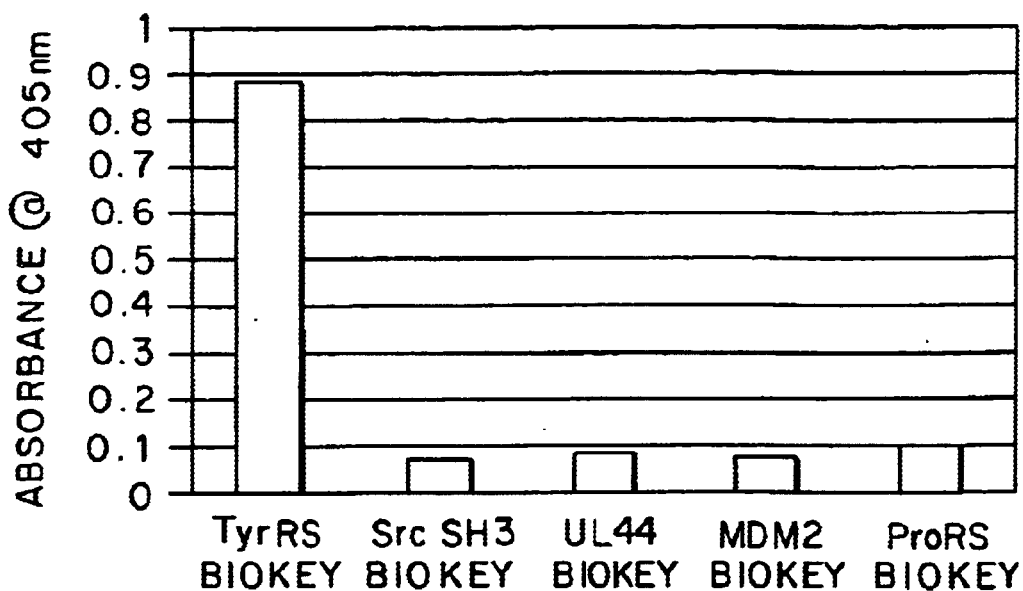

FIG. 16. Other BioKeys (Surrogate ligands) for other targets do not bind to TyrRS. Surrogate ligands for src SH3, UL44, MDM2 and ProRS were tested for binding to ProRS as described in the text.

Figure 17:
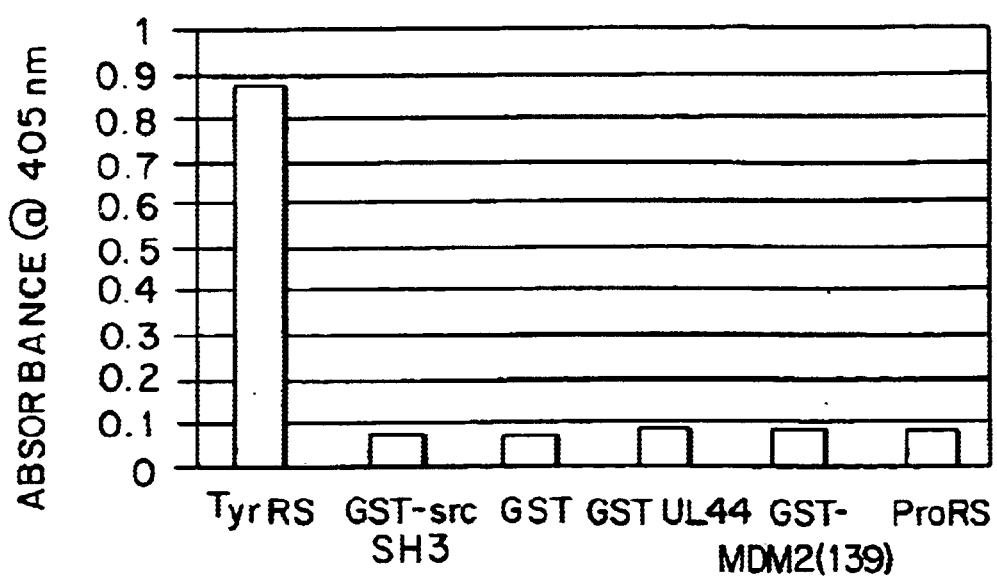

FIG. 17. Binding Specificity of the TyrRS BioKey (surrogate ligand). The peptide isolated from affinity selection against TyrRS was synthesized and tested for specific binding as described in the text. The targets tested were TyrRS, GST-src SH3, GST, GST-UL44, GST-MDM2 and ProRS. The amount of biotinylated peptide binding was monitored using a streptavidin-HRP conjugate.

Figure 18:
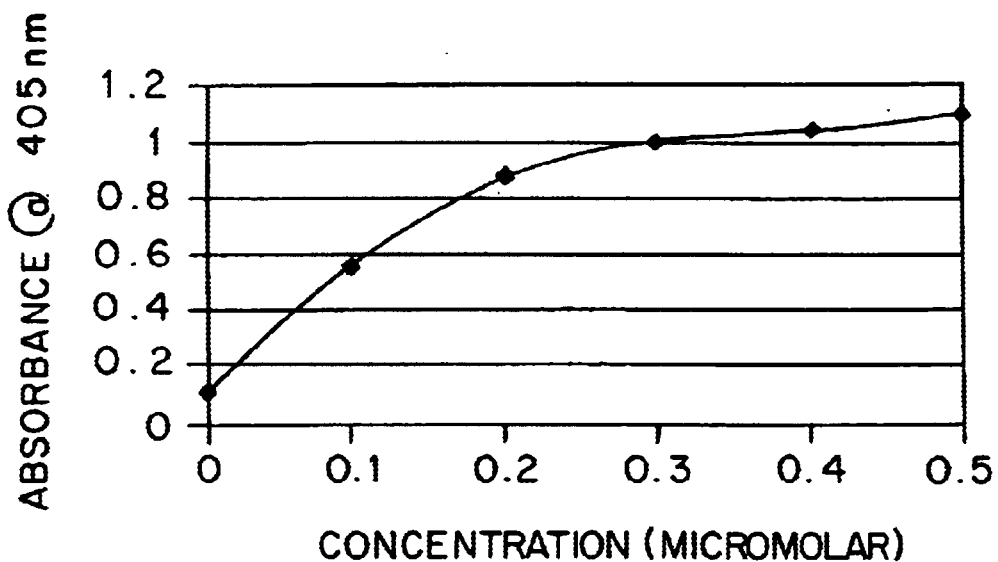

FIG. 18. Concentration dependent binding of the TyrRS BioKey (surrogate ligand). The binding of biotinylated peptide was monitored as a function of peptide concentration (from 0.1 to 0.5 micrograms).

Figure 19:
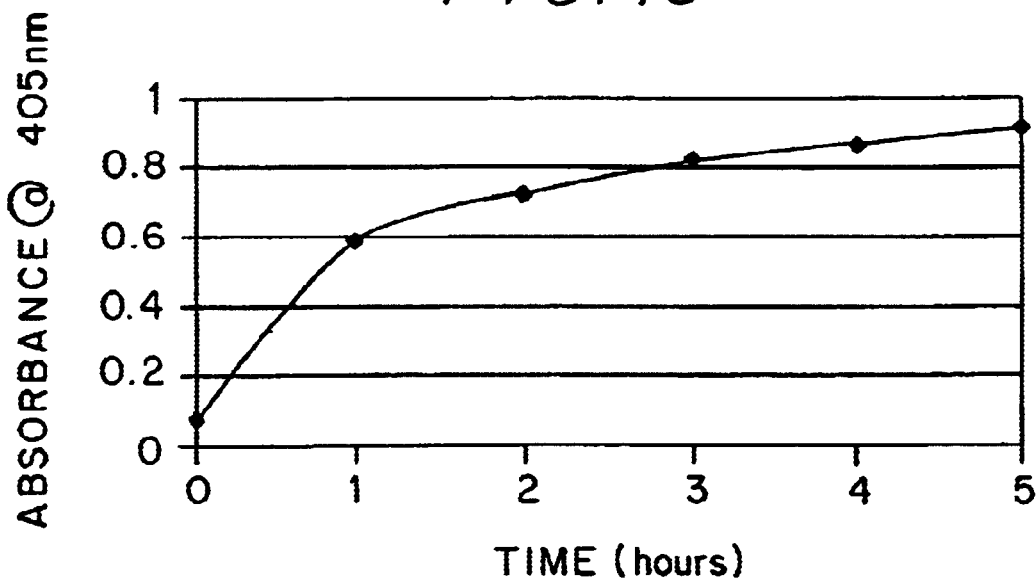
Figure 20:
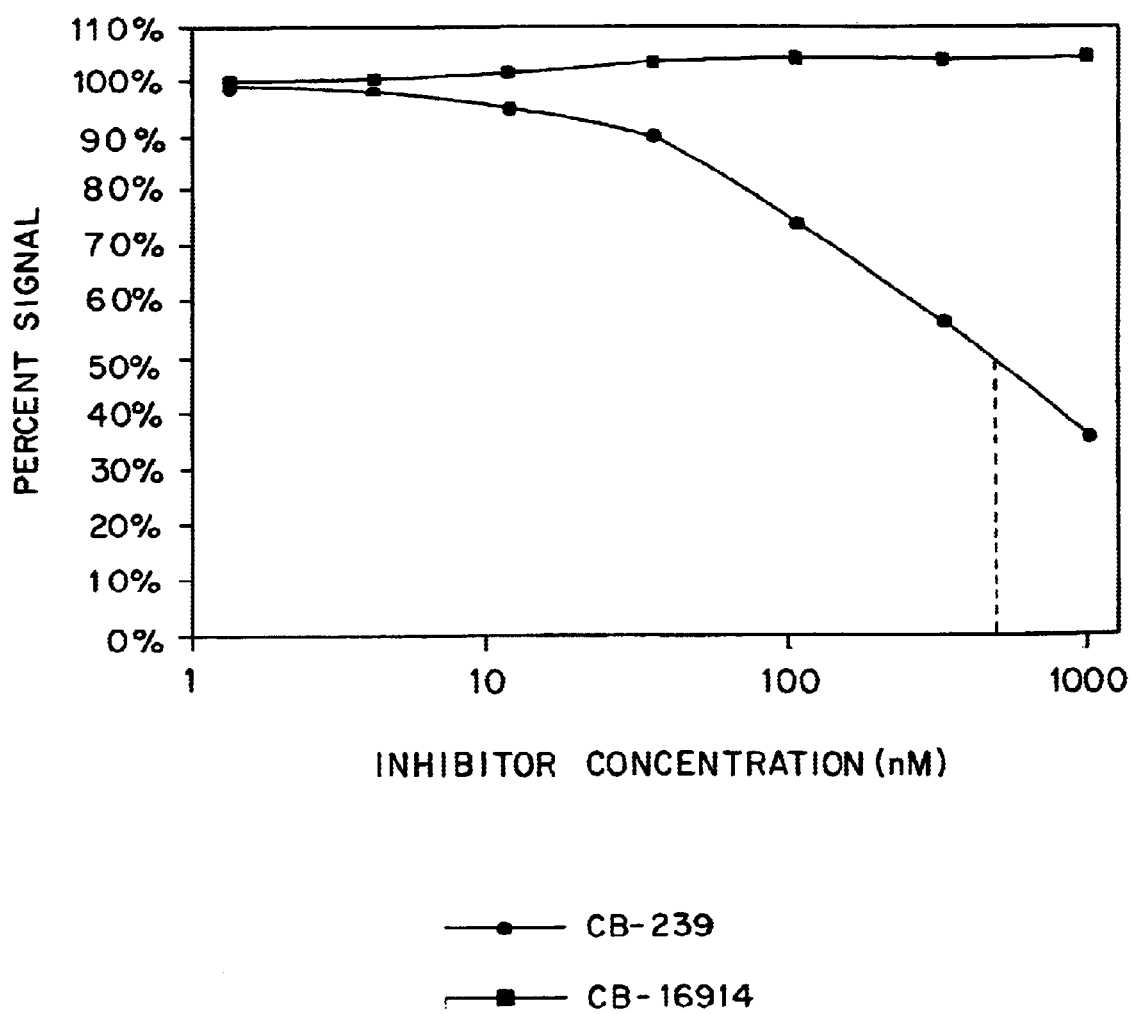

FIG. 19. Time Course for Binding of TyrRS BioKey (biotinylated peptide). FIG. 20. Competition between HiTyrRs BioKey and CB239 and CB16914 for binding between surrogate ligand and inhibitor. Competitive binding experiments were carried out as described in the text using TyrRS immobilized on plates as a target. Various concentrations of inhibitor CB239 was added to each well and the binding of surrogate ligand was monitored using a ELISA. Diamonds represent competition with a specific inhibitor (CB239) which binds to the active site of the enzyme. Square boxes represent competition with a related inhibitor (CB16914) which has no effect on TyrRS activity.

Figure 21:
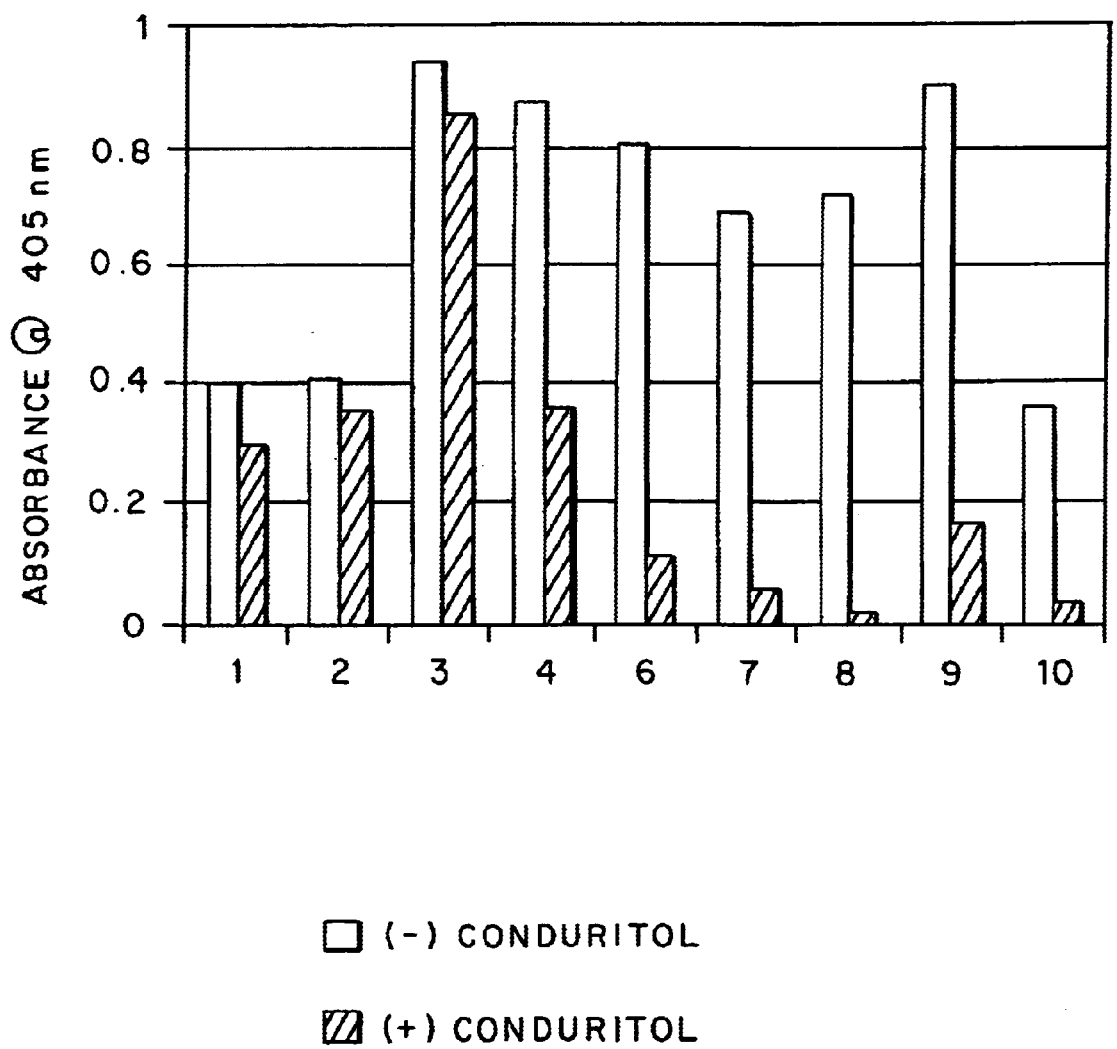

FIG. 21. Competition for binding between phage and an inhibitor. Competitive binding experiments were carried out as described in the text using beta-glucosidase immobilized on plates as a target. The binding of phage was monitored using a phage ELISA. Solid bars represent phage binding in the absence of inhibitor and hatched bars represent phage binding in the presence of inhibitor.

Figure 22:
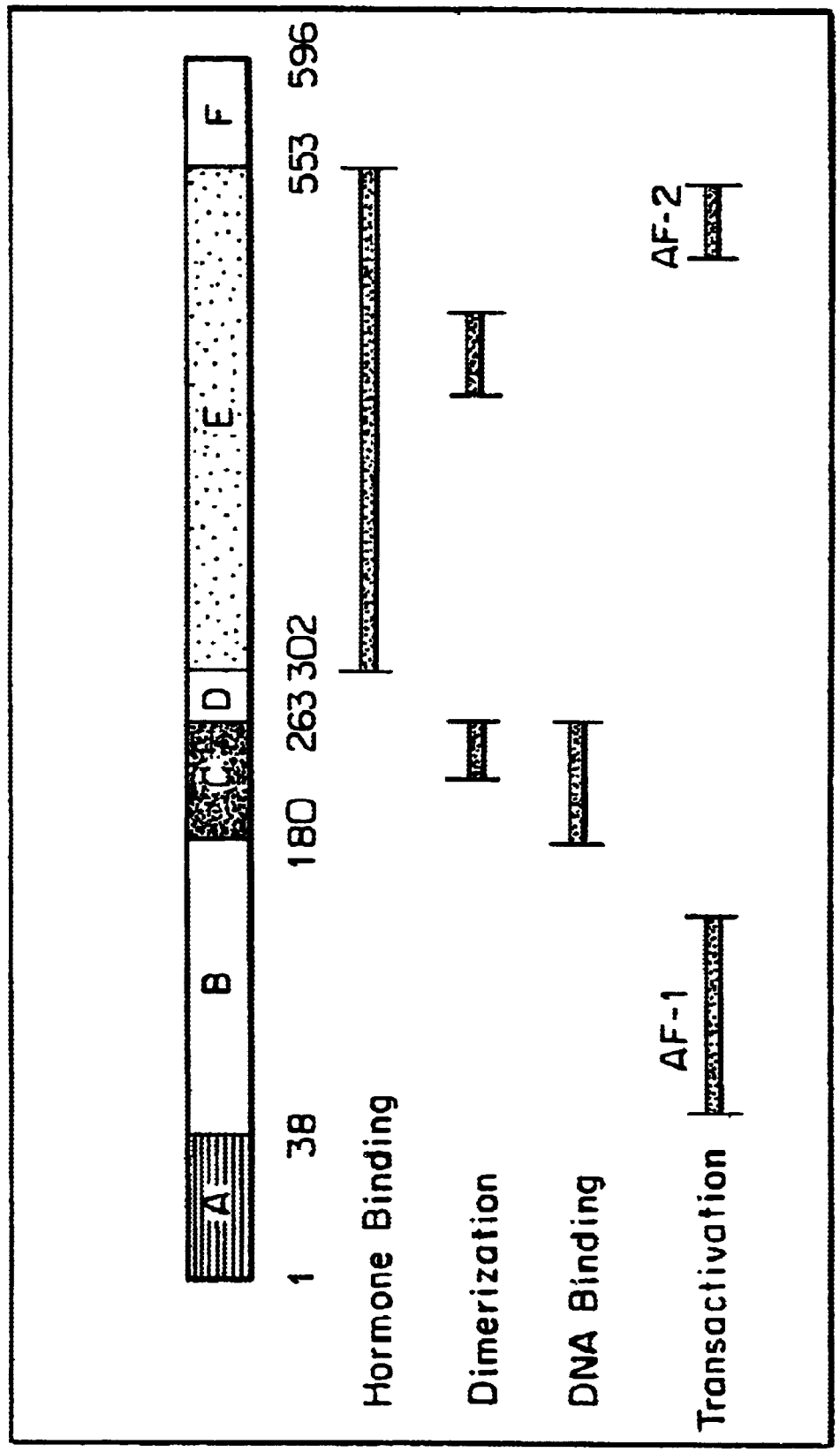

FIG. 22. Structural and Functional Domains of the Estrogen Receptor. Structural domains are labeled A-F. Functional domains for hormone binding, dimerization, DNA binding, and transactivation are indicated.

Figure 23:
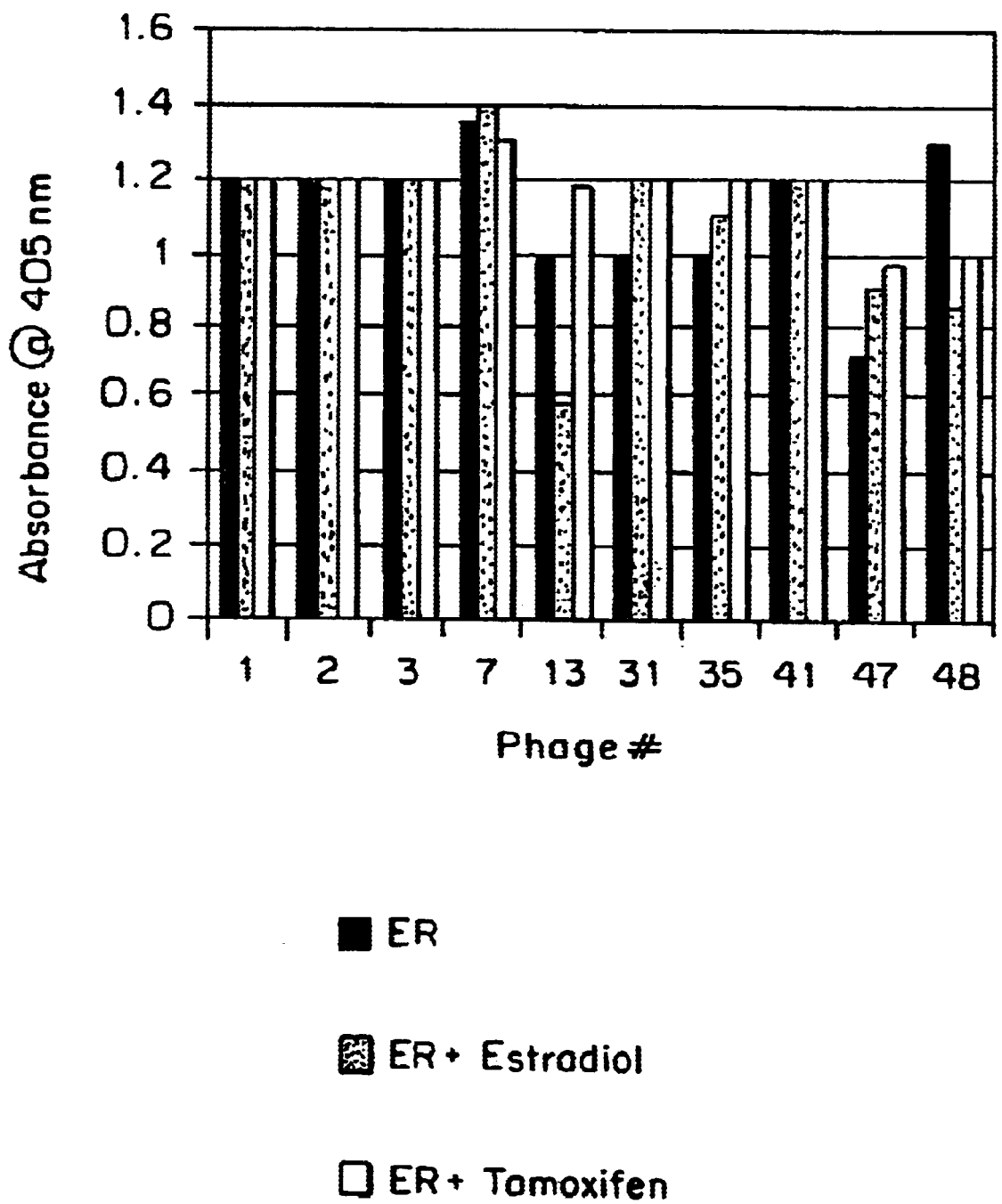

FIG. 23. Competition of estrogen receptor (ER) binding phage with estradiol and tamoxifen in a phage ELISA-format.

Figure 24A:
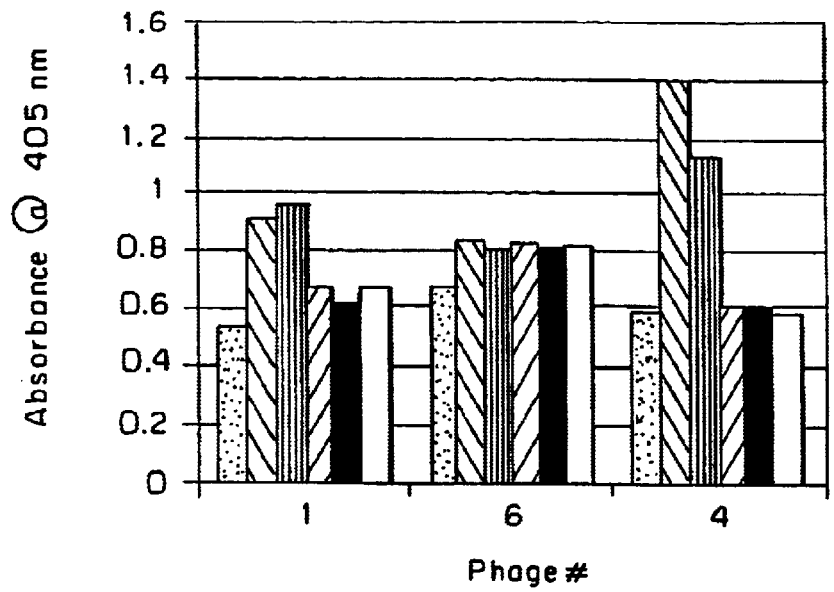

FIG. 24A. Binding Activity of phage with LXXLL (Seq. ID. No.121) motif to Estrogen Receptor, in presence of estradiol, estriol, tamoxifen, nafoxidene, clomiphene, or without a competitor.

Figure 24B:
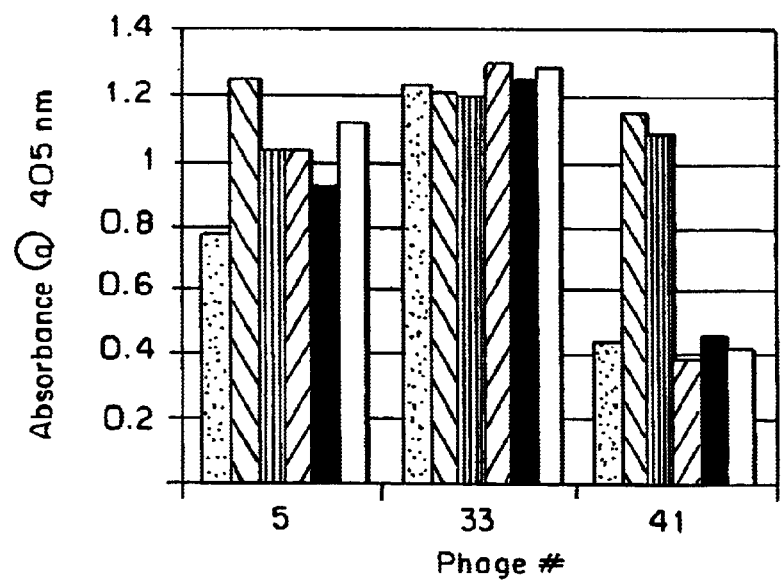

FIG. 24B. Binding Activity of phage without LXXLL (Seq. ID. No.121) motif to Estrogen Receptor, in presence of estradiol, estriol, tamoxifen, nafoxidene, clomiphene, or without a competitor.

In both FIGS. 24A and 24B, the phage were selected for binding to ER in the presence of estradiol.

DETAILED DESCRIPTION OF THE PREFERRED EMBODIMENTS

The present invention is directed to the identification of compounds in a compound library which can mediate the biological activity of a target receptor protein, even when the ligands which mediate that activity through binding to that receptor are not already known. Such compounds can then be used as "drug leads", i.e., used as a starting point for the design of analogues which can in turn be tested for activity.

The method of the invention comprises three steps:
(1) Screen at least one potential surrogate combinatorial library (as previously defined) for members (preferably peptides or nucleic acids) binding to the target protein (TP) and hence capable of use as surrogates for the unknown ligand in steps (2) and (3).
(2) Screen at least one complementary library, preferably a combinatorial library, (which is not limited to, and may not even include, peptides, or nucleic acids and hence is referred to on occasion as a "compound library") for compounds which inhibit the binding of one or more surrogates (peptides or nucleic acid which bind TP to TP.
(3) Determine whether the inhibitory compound mediates the biological activity of the said TP.

A library screening program may include multiple rounds of surrogate library screening, with the first library sampling a broad "sequence space", and later libraries focusing on sequences related to those previously found to bind the target. Or the different libraries may sample different sequence spaces, such as peptides and nucleic acids, or peptides of different length or composition. Similarly, it may include multiple rounds of screening of complementary library. The later rounds may sample the same class of compounds, a different class of compounds, or a subclass of those previously screened. Different rounds may use different surrogates in the screen. The screenings may occur in any rational order, e.g., surrogate/complementary/surrogate/complementary, or surrogate/surrogate/complementary/complementary. The compounds of the complementary library may be screened simultaneously or sequentially.

If the invention is described below with specific reference to peptide surrogates, such description applies mutatis mutandis to nucleic acids, too.

In effect, since the natural ligands of the receptor protein are not known (or for some other reason are not desirable for use in screening) a peptide library is searched to identify surrogate ligands. Of course, even if a given peptide does bind the receptor protein, there is no guarantee that it binds it at the correct site. However, by screening a diverse peptide library, many TP-binding peptides can be identified. It is likely that at least one of these peptides will bind the TP at the same site as it is bound by a natural ligand. The peptide library "samples" the surface of the TP for sites having a high interaction potential. It is likely that the TP evolved to offer one or more such sites and that such a site evolved to permit binding by the natural ligand (or that the natural ligand evolved to bind such a site on the TP). Preferably, the peptide library is a biased library as hereafter defined.

If desired, once TP-binding peptides have been identified, they may be screened for ability to act as a surrogate for the natural ligand, i.e., to mediate the biological activity of the TP. If so, then only the TP-binding peptides with this mediative property need be used in the second step.

In the second step, a compound library is screened for the ability of the compounds to inhibit the binding of the TP-binding peptides of step (1) with the TP. The compounds need not be peptides, and may be screened sequentially or simultaneously.

The affinity range of the TP-binding (surrogate) peptides for the TP must be such that binding is detectable, and that inhibition of such binding by the compounds sought to be found is also detectable. Initially, the compounds screened are likely to have low inhibitory activity. As lead optimization progresses, compounds of higher inhibitory activity are more likely to be present. Different surrogate peptides may be preferred for initial and subsequent rounds of library construction and screening. Generally speaking, affinity in the range of 10–5 to $10^{-11}$ M is desirable. The affinity of the surrogate ligand for the TP and the affinity range of compounds sought for in the first round will determine the concentrations of surrogate ligand and drugs used in the screen. It is preferable to keep the surrogate ligand concentration below its binding constant and the drug lead concentration above its binding constant. For example, if a peptide surrogate ligand has a binding constant of $1\times10^{-7}$ M, it should be used at concentrations of less than this in the assay. Conversely, if one wished to find compounds which bound to the TP with affinities around $1\times10^{-6}$ M, then the compounds should be present at higher concentrations than this in the assay. This does place limits on useful ligands and compounds. The ligand must be used at a concentration where its binding can still be detected. Thus with present detection methods, it is not desirable to use surrogate ligands with binding constants less (affinity greater) than $1\times10^{-12}$ M, and compounds with binding constants greater (affinities poorer) than $10^{-6}$ M are not likely to be detected. As detection limits improve, the desired affinities will change.

The foregoing is not to be construed as limiting the invention to a particular affinity range.

The compounds may inhibit the binding of the TP-binding peptides to the TP either by binding to the peptide, or to the TP. Those that actually bind to the TP are more likely to mediate the biological activity of the TP. Those that bind to the TP-binding peptide alone are less likely to be useful, unless the TP-binding peptide is a true surrogate for the natural ligand, i.e., the compound cross-inhibits the natural ligand.

Finally, we determine whether the inhibitory compounds in fact mediate the biological activity of the TP.

In theory, it is possible to screen the compound library directly for ability to interact with the TP. For instance one can label the TP directly (see below) and test binding directly to a library of diverse compounds which are themselves immobilized on pins (Proc Natl Acad Sci USA 91: 4708–12 (1994) The combinatorial synthesis and chemical and biological evaluation of a 1,4-benzodiazepine library, B. A. Bunin, M. J. Plunkett & J. A. Ellman) or beads (Proc Natl Acad Sci USA 90: 10922–6 (1993) Complex synthetic chemical libraries, indexed with molecular tags, M. H. Ohlmeyer, R. N. Swanson, L. W. Dillard, J. C. Reader, G. Asouline, R. Kobayashi, M. Wigler & W. C.Still). However, such screening by direct binding severely limits the selection of compound libraries that can be screened. For instance, many large pharmaceutical companies have accumulated many thousands of compounds over the years. Such compounds are stored either as dry powders or in solution and hence can not be assayed for direct interaction with a putative protein drug target since they are not immobilized to any sort of solid matrix.

Furthermore, binding of the TP to immobilized compounds may be sterically hindered due to its orientation to the pin or bead matrix. Thus, screening assays carried out in solution, as in the preferred method of screening of the complementary library in the present invention, are preferred.

Another advantage this method provides is focusing drug leads to sites on the TP which are biologically relevant. Assays which only require the compound binding to the target do not select for compounds which affect the activity of the TP, e.g., an interaction (e.g., enzymatic) of the TP with a biological ligand (for example another protein).

In another aspect, the present invention is used to identify the biological activity of a target protein whose biological function is not known and perhaps cannot be determined directly.

In this method, compounds of known (or determinable) biological activity are screened for their ability to inhibit the binding of a peptide which binds the target protein. If such a compound inhibits such binding, it is hypothesized that the target protein mediates one or more of the biological activities of the compound.

The complementary library need not be a combinatorial library, provided that it is a library of substantial (e.g., 100 compound) structural diversity, e.g., a library of isolated natural products from various plant or animal sources, or a library of analogues previously made in various drug development programs.

Target Protein

The target protein may be a naturally occurring protein, or a subunit or domain thereof, from any natural source, including a virus, a microorganism (including bacterial, fungi, algae, and protozoa), an invertebrate (including insects and worms), or the normal or cancerous cells of a vertebrate (especially a mammal, bird or fish and, among mammals, particularly humans, apes, monkeys, cows, pigs, goats, llamas, sheep, rats, mice, rabbits, guinea pigs, cats and dogs). Alternatively, the target protein may be a mutant of a natural protein. Mutations may be introduced to facilitate the labeling or immobilization of the target protein, or to alter its biological activity (An inhibitor of a mutant protein may be useful to selectively inhibit an undesired activity of the mutant protein and leave other activities substantially intact).

A target protein may be said to be associated with a particular organism if the organism is genetically capable of expressing the protein, or a precursor thereof, and does produce it in detectable quantities under some conditions. It need not produce it all times, or in large amounts. A viral protein is deemed to be associated with the virus, rather than with the host organism, even though the virus causes the host cells to produce the protein.

The target protein may be, inter alia, a glyco-, lipo-, phospho-, or metalloprotein. It may be a nuclear, cytoplasmic, membrane, or secreted protein. It may, but need not, be an enzyme. The known binding partners (if any) of the target protein may be, inter alia, other proteins, oligo- or polypeptides, nucleic acids, carbohydrates, lipids, or small organic or inorganic molecules or ions. The biological activity or function of the target protein may be, but is not limited to, being a Kinase
   protein kinase
     tyrosine kinase
     Threonine kinase
     Serine Kinase
   nucleotide kinase
   polynucleotide kinase
Phosphatase
   Protein phosphatase
   nucleotide phosphatase
   acid phosphatase
   alkaline phosphatase
   pyrophosphatase
Deaminase
Protease
   endoprotease
   exoprotease
   metalloprotease
   serine endopeptidase
   cysteine endopeptidase Nuclease
   Deoxyribonuclease
   ribonuclease
   endonulcease
   exonuclease
Polymerase
   DNA Dependent RNA polymerase
   DNA Dependent DNA polymerase
   telomerase
   primase
Helicase
Dehydrogenase
Transferase
   peptidyl transferase
   transaminase
   glycosyltransferase
   ribosyltransferase
   acetyltransferase
Hydrolase
   urease
Carboxylase
Isomerase
   dismutase
   rotase
   topoisomerase
Glycosidase
   endoglycosidase
   exoglycosidase
Deaminase
Lipase
Esterase
Sulfatase
Cellulase
Lyase
Reductase
Synthetase
   Ion Channel
DNA Binding
RNA Binding
Ligase
   RNA ligase
   DNA ligase
Adaptor or Scaffolding Protein
Structural Protein
   fibrin(ogen)
   collagen
   elastin
   talin
Tumor Suppressor
Adhesion Molecule
Oxygenase
Oxidase
   peroxidase
Chaperonin
Transporter
   electron transporter
   protein transporter
   peptide transporter
   hormone transporter
     serotonin
     DOPA
   nucleic acid transporter
Signal Transduction
Neurotransmitter
Structural Component
   of viruses
   of cells
   of organs
   of organisms
Information Carrier/storage
Antigen Recognition Protein
   MHC I complex
   MHC II complex
Receptor
   TNFα Receptor
   TNFβ Receptor
   β-Adrenergic Receptor
   α-Adrenergic Receptor
   IL-8 Receptor
   IL-3 Receptor
   CSF Receptor
   Erythropoeitin Receptor
   FAS Ligand Receptor
   T-cell Receptors
   B-Cell Antigen Receptor
   F epsilon Receptor
   Growth Hormone Receptor
   Nuclear Receptors
     Glucocorticoid
     Estrogen
     Testosterone The binding protein may have more than one paratope and they may be the same or different. Different paratopes may interact with epitopes of different binding partners. An individual paratope may be specific to a particular binding partner, or it may interact with several different binding partners. A protein can bind a particular binding partner through several different binding sites. The binding sites may be continuous or discontinuous (vis-a-vis the primary sequence of the protein)

The present invention applies, mutatis mutandis, to macromolecular targets which are not proteins.

Peptide Libraries

A peptide library is a combinatorial library, at least some of whose members are peptides having three or more amino acids connected via peptide bonds. In an oligopeptide library, the lengths of the peptides do not exceed 50 amino acids. The peptides may be linear, branched, or cyclic, and may include nonpeptidyl moieties. The amino acids are not limited to the naturally occurring amino acids.

A biased peptide library is one in which one or more (but not all) residues of the peptides are constant residues. The individual members are referred to as peptide ligands (PL). In one embodiment, an internal residue is constant, so that the peptide sequence may be written as $(X_{aa})_m - AA_1 - (X_{aa})_n$ Where Xaa is either any naturally occurring amino acid, or any amino acid except cysteine, m and n are chosen independently from the range of 2 to 20, the Xaa may be the same or different, and $AA_1$ is the same naturally occurring amino acid for all peptides in the library but may be any amino acid. Preferably, m and n are chosen independently from the range of 4 to 9.

Preferably, $AA_1$ is located at or near the center of the peptide. More preferably, $AA_1$ is either (a) at least five residues from both ends of the peptide, or (b) is in the middle 50% of the peptide. More preferably, that m and n are not different by more than 2; most preferably m and n are equal. Even if the chosen $AA_1$ is required (or at least permissive) of the TP binding activity one may need particular flanking residues to assure that it is properly positioned. If $AA_1$ is more or less centrally located, the library presents numerous alternative choices for the flanking residues. If $AA_1$ is at an end, this flexibility is diminished.

The most preferred libraries are those in which $AA_1$ is tryptophan, proline or tyrosine. Second most preferred are those in which $AA_1$ is phenylalanine, histidine, arginine, aspartate, leucine or isoleucine. Third most preferred are those in which $AA_1$ is asparagine, serine, alanine or methionine. The least preferred choices are cysteine and glycine. These preferences are based on evaluation of the results of screening random peptide libraries for binding to many different TPs.

The effect of fixing one position in a library is to increase the occurrence of that particular residue from 1 in 20 to 20 in 20, an increase of 20 fold. Thus in theory if a particular residue is required for binding in the middle of the peptide, the rate of finding clones would be 20 fold higher than if a random residue were used. Therefore by using 20 libraries with one fixed residue the chances of finding members that bind to the target protein would be increased [20×(# of residues conserved for binding)] when compared to using completely random libraries. These 20 libraries (or at least a subset of them) would be effective against any target and no prior knowledge of the sequence for the peptide ligand would be required.

Ligands that bind to functional domains tend to have both constant as well as unique features. Therefore, by using "biased" peptide libraries, one can ease the burden of finding ligands.

For example, HPQ occurs in most streptavidin-binding peptides, which bind with the HPQ side chains oriented inward so as to interact with the biotin-binding site of the TP streptavidin. Some of the residues that participate in binding biotin also interact with the peptides; however, the peptides adopt an alternate method of utilizing binding determinants (Biochemistry 31: 9350–4 (1992) [93003082], Crystal structure and ligand-binding studies of a screened peptide complexed with streptavidin, P. C. Weber, M. W. Pantoliano & L. D. Thompson). Therefore, if one starts off with a biased library e.g. X(6)-H-X(6), then one finds many binding peptides in a short period of time because that library will be rich in peptides having the cognate binding site.

The example above showed a biased library with one residue held constant. The net effect of this is to increase the number of peptides with the constant residue in that position. If this residue at this position is helpful for binding, then the number of individuals per library that will bind to the target protein will be increased. If all the amino acids are represented equally, then the number of potential binding peptides is increased 20 fold in a library made up of the 20 naturally occurring amino acids. Libraries using different ratios of amino acids will be enriched according to the proportion of each residue in the starting library.

Of course, if the library is biased with a constant residue which happens to disrupt binding, the screening results will be negative. Therefore, it may be advantageous to screen a plurality of different biased peptide libraries in parallel. One could have a constant Trp, another, a constant Glu, etc.

If two residues were held constant and both were required for binding, then the incidence of binders would be increased by a much larger amount. The incidence of occurrence is independent at each position, therefore holding two residues constant is multiplicative: in a simple case of equal representation, 20 fold for each site or 400 fold overall. Evidence supporting this was found in the use of a two residue biased library to enrich for peptides which bind to src domains (SH3) (Proc. Natl. Acad. Sci. USA. 93:1540–1544 (1996) Distinct ligand preferences of Src homology 3 domains from Src, Yes, Abl, Cortactin, p53bp2, PLCgamma, Crk, and Grb2. A. Sparks, J. Rider, N. Hoffman, D. Fowlkes, L. Quilliam, and B. Kay). The authors found an increase in the titers of SH3-binding phage approximately 100 fold over random libraries of the same size and complexity. This is close to the theoretical increase for these libraries ((2 codons for P divided by 31 possible codons)$^2$=240 fold increase).

The use of libraries biased at two positions known to be required for binding is an extremely powerful tool. However, to make parallel biased libraries which collectively include all eleven amino acid peptides, with, in each individual biased library, two constant residues, would require 44,000 libraries. (11 positions for fixed residue 1×20 amino acids×10 positions for fixed residue 2×20 amino acids). Even if one of the constant residues were always the middle residue, there would be 4,000 libraries. While screening this number of libraries may be possible, the increase in the number of binding peptides would probably not justify the complexities of the task. However, if the number of libraries was limited to less than 100, these could be screened with relative ease.

The task can be reduced to this practical level if the following assumptions and approaches are used. First, some residues have similar functional groups and are often interchangeable for peptide target interactions. In addition, due to the degeneracy in the genetic code, many amino acids can be encoded by allowing one base in a codon to be degenerate. Amino acids can be grouped and coded for in the following manner.

| 1 | W | TGG |
| 2 | F, Y | T(T,A)T |
| 3 | P | CCT |
| 4 | H | CAT |
| 5 | D, E | GAX |
| 6 | K, R | A(G,A)A |
| 7 | N | AAT |
| 8 | Q | CAA |
| 9 | L, I, V | (G,A,C)TT |
| 10 | M | ATG |
| 11 | S, T | A(G,C)T |
| 12 | A, G | G(G,C)T |
| 13 | C | TGT |

This reduces the number of variables to 13, however this would still require 1690 (13×13×10) libraries to represent all the possible combinations in a 11 mer with the central residue held constant and one additional constant residue scanning the remaining 10 positions. This number can be reduced 10 fold by constructing the libraries using mixed oligonucleotides in the following way. In this example a central residue is held constant as a W (encoded by TTG), and D, E (encoded by GAX) are scanned through the remaining 10 positions. To construct the library, 10 oligonucleotides are synthesized:

```
1   GAX NNK NNK NNK NNK TGG NNK NNK NNK NNK NNK        (SEQ ID NO:1)

2   NNK GAX NNK NNK NNK TGG NNK NNK NNK NNK NNK        (SEQ ID NO:2)

3   NNK NNK GAX NNK NNK TGG NNK NNK NNK NNK NNK        (SEQ ID NO:3)

4   NNK NNK NNK GAX NNK TGG NNK NNK NNK NNK NNK        (SEQ ID NO:4)

5   NNK NNK NNK NNK GAX TGG NNK NNK NNK NNK NNK        (SEQ ID NO:5)

6   NNK NNK NNK NNK NNK TGG GAX NNK NNK NNK NNK        (SEQ ID NO:6)

7   NNK NNK NNK NNK NNK TGG NNK GAX NNK NNK NNK        (SEQ ID NO:7)

8   NNK NNK NNK NNK NNK TGG NNK NNK GAX NNK NNK        (SEQ ID NO:8)

9   NNK NNK NNK NNK NNK TGG NNK NNK NNK GAX NNK        (SEQ ID NO:9)

10  NNK NNK NNK NNK NNK TGG NNK NNK NNK NNK GAX        (SEQ ID NO:10)
```

These are converted to double stranded oligonucleotides, mixed together and cloned as a group into a phage display vector by conventional methods. The end result is a library that displays peptides with a central W residue and enriched for either D or E in each of the 10 flanking positions. The enrichment in the flanking residues occurs only once per peptide, thereby allowing the rest of the peptide to be random. Thus if the enriched residues (in this case D or E) increase binding in position 1 but are deleterious for binding in other positions, these libraries would still code for a higher number of peptides with the ability to bind to the target protein. This is an advantage over constructing libraries from triplet codon subunits and varying the ratio of each codon represented at each position and constructing the library from a single codon.

One additional complexity added to this calculation is the use of an NNK coding scheme to represent all 20 amino acids. Residues L, R, and S are overrepresented 3 fold in this scheme while V, T, A, G, and P are overrepresented 2 fold. These residues are present in higher amounts using the NNK coding scheme and the increase in the number of surrogate ligands isolated by enriching for these residues will be less than those residues that are coded for only once. The degree of overrepresentation/underrepresentation may be reduced by using non-equimolar mixtures of bases at each position. This problem could be avoided altogether if the nucleic acid were synthesized triplet by triplet, rather than base by base, so at each step one added one out of 20 possible trinucleotides, each encoding a different amino acid.

It is desirable to enrich for residues that are important for protein-peptide interactions. These residues contain side chains that can interact with other amino acids and are less likely to pack tightly, allowing a greater degree of freedom for interaction with other ligands. A study of residues at protein binding sites showed an overrepresentation of R, H, W, and Y (Villar and Kauvar, FEBS Letters 349: 125–130 (1994) Amino acid preferences at protein binding sites). A compilation of peptide sequences derived from the phage display against a series of proteins reveals that the amino acids are not found in equal amounts, that is to say that some amino acids appear in peptides that bind to various targets more frequently than other amino acids. A graph which shows the raw incidence of residue occurrence in peptides binding to any of 16 proteins is shown in FIG. 3; FIG. 4 shows the effect of correcting for codon usage. There is a clear overrepresentation of aromatic residues, proline, cysteine and aspartic acid. Biased libraries with these residues fixed or scanning through the displayed peptide are preferred, whereas biased libraries with residues that are under represented (such as alanine, methionine, and lysine) are less preferred with libraries containing the remaining residues fixed or scanning of intermediate usefulness. As new peptides are described for additional targets this data set should be updated and reevaluated, however, the trends are quite clear.

An empirical way of determining which residues are preferred would be to take a representative mixture of proteins and bind to them a random synthetic peptide library. After washing away the peptides that did not bind, the remaining peptides could be eluted and the molar ratio of residues remaining bound could be determined. The profile should tell which residues result in peptides which would bind to the original mixture of proteins. This approach would also work on an individual target, providing initial information on residues important for binding. An alternative method for determining which residues are preferred would be to take the mixture of proteins and use a set of phage display libraries in which one residue of the displayed peptide is fixed to select for binding phage. After several rounds of affinity selection, the libraries with the greatest number of binding phage should be those where the fixed residue is contributing to the binding of the displayed peptides.

Using the information from above, the number of libraries can be reduced greatly if the central residue that is held constant is from group 1 through 7 and 13. The C residue is a special case where the C held constant will be placed at the end of the peptide, not in the middle. However, there are special uses for libraries having cysteine contrained loops (see examples 1, 2, and 4) and this method would be especially useful to increase the number of binding peptides from these libraries. These 8 constant residues can be combined with residues from groups 1–7, giving a structured panel of 56 libraries, a practical number to construct and manipulate.

While certain synthetic strategies have been discussed above, the present invention is not limited to any particular method of synthesizing a combinatorial peptide library with one or more predetermined positions held constant, or with a particular mixture of amino acids at a given position.

Another way of thinking about the biased libraries is that they represent a more efficient way of generating complexity. If the structural properties of the binding site on the TP is such that only PLs with a certain residue, say W can bind, then a library with a single fixed, centrally positioned W will have more potential binding motifs than will a totally random library with the same numbers of unique members. However, it is readily apparent that using a library with a fixed VI will in fact be a hindrance if the TPs binding site does not (and especially if they cannot) bind PLs with a W.

Therefore, it is important to take note of any apparent motifs shared in common between the diverse PLs identified which bind to a specific TP. This has two purposes. Firstly, if the TP has more that one functional domain (FD), then it may bind to two distinct populations of PLs. It is desirable to discern this before actual setting up the drug screens themselves. If there is more than a single FD in a TP, then the likelihood of finding a suitable drug lead by creating and carrying out screens for all FDs is increased. The more domains on a target for a potential drug to interact, the more likely one is of identifying compounds that act on that particular TP. However, there are no assurances that one can detect multiple FDs if they actually exist. For example, a TP might have two very similar FDs (such as two SH3 domains within the adaptor protein Grb-2) and thus the PLs may be of a single class even though the TP has two FDs.

Secondly, the chemical nature of the residue side chains composing the motifs provide very useful information about the nature of the LP/FD interaction. This information is quite helpful in directing one's attention to particular compound libraries, or certain subsets of compound libraries for the screening process. Each amino acid has characteristic side chains, with particular characteristics of size, charge and hydrophilicity. If particular amino acids are favored at certain positions in the peptide library it suggests what substituents might be favored in the compound libraries. Some examples are given below:

| Residues | Substituents to consider |
|---|---|
| Ser, Thr | hyroxylated species, especially those aliphatic in nature. Also thiolated species. |
| Asp, Glu | carboxylated species, especially those aliphatic in nature. Esters and alcohols. |
| Asn, Gln | carboxylated species; amides. |
| Lys, Arg | aminated species; derivatives of the delta-guanido group. |
| His | aromatic compounds with heterocyclic nitrogen especially imidazole derivatives. |
| Phe | aromatic compounds, substituted or not. |
| Tyr | as for Phe, but also hydroxylated species. |
| Trp | aromatic structures, especially with two or three fused rings; the rings may include heterocyclic nitrogen; indole derivatives are of particular interest. |
| Cys | thiolated and hydroxylated species. |
| Met | thiolated species; sulfonium salts; sulfoxides; sulfones. |
| Ala, Val, Leu, Ile | aliphatic hydrocarbons |
| Pro | pyrrolidine derivatives. |

It must be emphasized that these are suggestions, not requirements.

Giving priority to the libraries likely to provide the most "hits" is time and cost effective. The process is akin to "rational drug design" but is probably better called "rational library selection" herein.

If more than one peptide ligand is identified, they can be tested against each other. Competitive inhibition implies that they bind to the same site; its absence, that they bind to different sites. If the functional domains of the TP are known, these domains can be used separately as screening targets to identify which ligands bind which domains.

A peptide library may be prepared by biological or nonbiological synthesis methods. In a biological synthesis method, a gene encoding the peptides of interest is expressed in a host cell so that the peptides are displayed either on the surface of the cell or on the outer coat of phage produced by the cell. Of course, to achieve diversity, the gene must be randomized at those codons corresponding to variable residues of the peptide. It thus is not a single DNA, but rather a DNA mixture, which is introduced into the host cell culture, so that each cell has the potential, depending on which DNA it receives, of expressing any of the many possible peptide sequences of the library. (On average, each cell will express only one of the sequences of the mixture.) The gene may be randomized by, in the course of synthesis, using a mixture of nucleotides rather than a pure nucleotide during appropriate synthetic cycles. The synthesis cycles may add one base at a time, or an entire codon.

The peptide library may also be prepared nonbiologically by stepwise addition of amino acids. During the cycles which incorporate variable residues, the activated AA is chosen randomly from an AA mixture. Preferably, the synthesis is carried out on a solid surface, such as a pin or bead. See (Proc Natl Acad Sci USA 81: 3998–4002 (1984) [84248046], Use of peptide synthesis to probe viral antigens for epitopes to a resolution of a single amino acid, H. M. Geysen, R. H. Meloen & S. J. Barteling) or bead (Nature 354: 82–4 (1991) [92049760] A new type of synthetic peptide library for identifying ligand-binding activity K. S. Lam, S. E. Salmon, E. M. Hersh, V. J. Hruby, W. M. Kazmierski & R. J. Knapp).

The peptide library may be attached to a polysome, see Kawasaki, U.S. Pat. Nos. 5,643,768 and 5,658,754; Gersuk, et al., Biochem. Biophys. Res. Comm. 232:578 (1997); Mattheakis, et al., Proc. Nat. Acad. Sci. USA, 91:9022–6 (1994).

If the peptide library is on a solid phase, then it is usual for the target protein to be labeled. The peptide "marked" by the labeled TP can then be sequenced.

Preferably the tags are such that only a minimal number of steps are necessary and that special handling such as that required for using radioisotopes can be minimized. Suitable epitopes e.g. cMyc or influenza hemagglutinin, or enzymes such as beta-galactosidase, luciferase, orglutathione-S-transferase (GST), or fluorochromatic proteins (e.g., the green fluorescent protein of algae), are incorporated into the primary structure of the TP using recombinant DNA skills. Such epitopes are conveniently detected by use of the appropriate enzyme (alkaline phosphatase is preferred over horseradish peroxidase) conjugated antibodies. Other tags that can be incorporated via recombinant techniques include substrate sites for enzymes such as protein kinase A which allows for the rapid and efficient labeling of the TP with $^{32}P$. Less desirable, but still feasible, is the radio labeling of the recombinant protein, e.g., in vivo with $^{14}C$ or $^{3}H$ labeled amino acids or in vitro with $^{125}I$.

If the peptide library is in a solution phase, the TP may be immobilized, and the library screened by the method of Cantley, infra. The target may be immobilized on chromatographic media either directly, e.g., using AFFIGEL matrix (BioRad), or indirectly. In indirect immobilization, the TP is noncovalently conjugated to the support by means of an affinity reagent. For example, target protein tagged with six histidines may be immobilized on QIAGEN nickel binding resin, or a GST (glutathione S-transferase) tagged target immobilized on glutathione SEPHAROSE chromatography matrix (Pharmacia), or a maltose binding protein/target protein fusion immobilized on maltose (New England Biolabs) or dextran media. Subsequently, one uses the immobilized target to separate out peptides with desired activity by the method of Cantley et. al. (Trends Biochem. Sci. 20: 470–475 (1995)[96108162] Recognition and specificity in protein tyrosine kinase-mediated signalling.S. Zhou & L. C. Cantley and Methods Enzymol 254: 523–535 (1995)[96052729] SH2 domain specificity determination using oriented phosphopeptide library. S. Zhou & L. C. Cantley and Cell 72: 767–78 (1993)[9320159] SH2 domains recognize specific phosphopeptide sequences. S. Zhou, S. E. Shoelson, M. Chaudhuri, G. Gish, T. Pawson, W. G. Haser, F. King, T. Roberts, S. Ratnofsky, R. J. Lechleider & . . . ). In this method a mixture of peptides are eluted from the TP and the whole mixture sequenced by automated techniques. Useful information is most readily achieved by using biased peptide library pools wherein one amino acid resident is "fixed", for example, x-x-x-x-Y-x-x-x-x-x. If a tyrosine (Y) is in fact contained with a binding motif for a domain contained within the TP, then other residues within the motif will be in register with the tyrosine. Thus, if cognate binding peptides must have a leucine following the tyrosine, then the sequencing of the pool will yield a sequence of x-x-x-x-Y-L-x-x-x-x. Without a priori knowledge of the natural binding partner, this makes it preferable to use up to 19 (all amino acids except for cysteine) library pools. This is not really so overwhelming as the costs of the random peptide pools is not prohibitive. It is preferable to avoid cysteine as a component as peptides with an odd number of cysteines do not bind well.

In screening phage libraries, it is also routine to immobilize the TP on a solid support, since nonbinding phage can be removed. (Science 249: 404–6 (1990)[90333257], Random peptide libraries: a source of specific protein binding molecules, J. J. Devlin, L. C. Panganiban & P. E. Devlin; Science 249: 386–90 (1990)[90333256], Searching for peptide ligands with an epitope library, J. K. Scott & G. P. Smith; Gene 128: 59–65 (1993)[93285470], An M13 phage library displaying random 38-amino-acid peptides as a source of novel sequences with affinity to selected targets, B. K. Kay, N. B. Adey, Y. S. He, J. P. Manfredi, A. H. Mataragnon & D. M. Fowlkes).

The advantage of identifying peptides using the chemical synthesis-on-a-support (e.g., pins or beads) approach over peptide from phage display libraries are mostly due to the ease of identification of D-amino acid containing peptides which gives one a significant additional source of diversity. Conversely, the advantage of utilizing phage display libraries is that one can screen greater numbers of phage (perhaps $10^9$ or $10^{10}$) than pins (perhaps $10^4$ or $10^5$) or even possibly beads (perhaps $10^6$).

Peptoid Libraries

Peptoids are oligomers, similar to peptides, in which the peptide bond (—NHCO—) is replaced by an analogous linkage. For example, the —NH— may be replaced by —NR—, where R is a functional group other than H. It may be, for example, an alkyl or aryl group. The —NH— may also be replaced by, e.g., an isostere, such as —O—, —S—, or —CH=CH—. The —CO— may be replaced by, e.g., —SiO—, —CS—, —SO$_2$—, —PO(OH)—, or —COR—.

It is not necessary that all of the linkages in a peptoid be identical; e.g., the R in each —NRCO— may be different, as an additional (or alternative) source of diversity. A peptoid may include one or more peptidyl bonds, provided that at least one of the main chain linkages between units is not a peptidyl bond.

It is likely that peptoids will enjoy advantages similar to those of peptides for screening purposes, except that peptoid libraries cannot be prepared biologically.

Compound Library

The compound library is a combinatorial library whose members are suitable for use as drugs if, indeed, they have the ability to mediate a biological activity of the target protein.

Peptides have certain disadvantages as drugs. These include susceptibility to degradation by serum proteases, and difficulty in penetrating cell membranes. Preferably, all or most of the compounds of the compound library avoid, or at least do not suffer to the same degree, one or more of the pharmaceutical disadvantages of peptides.

In designing a compound library, it is helpful to bear in mind the methods of molecular modification typically used to obtain new drugs. Three basic kinds of modification may be identified: disjunction, in which a lead drug is simplified to identify its component pharmacophoric moieties; conjunction, in which two or more known pharmacophoric moieties, which may be the same or different, are associated, covalently or noncovalently, to form a new drug; and alteration, in which one moiety is replaced by another which may be similar or different, but which is not in effect a disjunction or conjunction. The use of the terms "disjunction", "conjunction" and "alteration" is intended only to connote the structural relationship of the end product to the original leads, and not how the new drugs are actually synthesized, although it is possible that the two are the same.

The process of disjunction is illustrated by the evolution of neostigmine (1931) and edrophonium (1952) from physostigmine (1925). Subsequent conjunction is illustrated by demecarium (1956) and ambenonium (1956).

Alterations may modify the size, polarity, or electron distribution of an original moiety. Alterations include ring closing or opening, formation of lower or higher homologues, introduction or saturation of double bands, introduction of optically active centers, introduction, removal or replacement of bulky groups, isosteric or bioisosteric substitution, changes in the position or orientation of a group, introduction of alkylating groups, and introduction, removal or replacement of groups with a view toward inhibiting or promoting inductive (electrostatic or conjugative (resonance) effects.

Thus, the substituents may include electron acceptors and/or electron donors. Typical electron donors (+I) include—CH$_3$, —CH$_2$R, —CHR$_2$, —CR$_3$ and —COO—. Typical electron acceptors (-I) include —NH$_3$+, —NR$_3$+, —NO$_2$, —CN, —COOH, —COOR, —CHO, —COR, —COR, —F, —Cl, —Br, —OH, —OR, —SH, —SR, —CH=CH$_2$, —CR=CR$_2$, and —C=CH.

The substituents may also include those which increase or decrease electronic density in conjugated systems. The former (+R) groups include —CH$_3$, —CR$_3$, —F, —Cl, —Br, —I, —OH, —OR, —OCOR, —SH, —SR, —NH$_2$, —NR$_2$, and —NHCOR. The later (-R) groups include —NO$_2$, —CN, —CHC, —COR, —COOH, —COOR, —CONH$_2$, —SO$_2$R and —CF$_3$.

Synthetically speaking, the modifications may be achieved by a variety of unit processes, including nucleophilic and electrophilic substitution, reduction and oxidation, addition elimination, double band cleavage, and cyclization.

For the purpose of constructing a library, a compound, or a family of compounds, having one or more pharmacological activities (which need not be related to the known or suspected activities of the target protein), may be disjoined into two or more known or potential pharmacophoric moieties. Analogues of each of these moieties may be identified, and mixtures of these analogues reacted so as to reassemble compounds which have some similarity to the original lead compound. It is not necessary that all members of the library possess moieties analogous to all of the moieties of the lead compound.

The design of a library may be illustrated by the example of the benzodiazepines. Several benzodiazepine drugs, including chlordiazepoxide, diazepam and oxazepam, have been used on anti-anxiety drugs. Derivatives of benzodiazepines have widespread biological activities; derivatives have been reported to act not only as anxiolytics, but also as anticonvalsants, cholecystokin (CCK) receptor subtype A or B, kappa opioid receptor, platelet activating factor, and HIV transactivator Tat antagonists, and GPIIbIIa, reverse transcriptase and ras farnesyltransferase inhibitors.

The benzodiazepine structure has been disjoined into a 2-aminobenzophenone, an amino acid, and an alkylating agent. See Bunin, et al., Proc. Nat. Acad. Sci. USA, 91:4708 (1994). Since only a few 2-aminobenzophenone derivatives are commercially available, it was later disjoined into 2-aminoarylstannane, an acid chloride, an amino acid, and an alkylating agent. Bunin, et al., Meth. Enzymol., 267:448 (1996). The arylstannane may be considered the core structure upon which the other moieties are substituted, or all four may be considered equals which are conjoined to make each library member.

Figure 1:
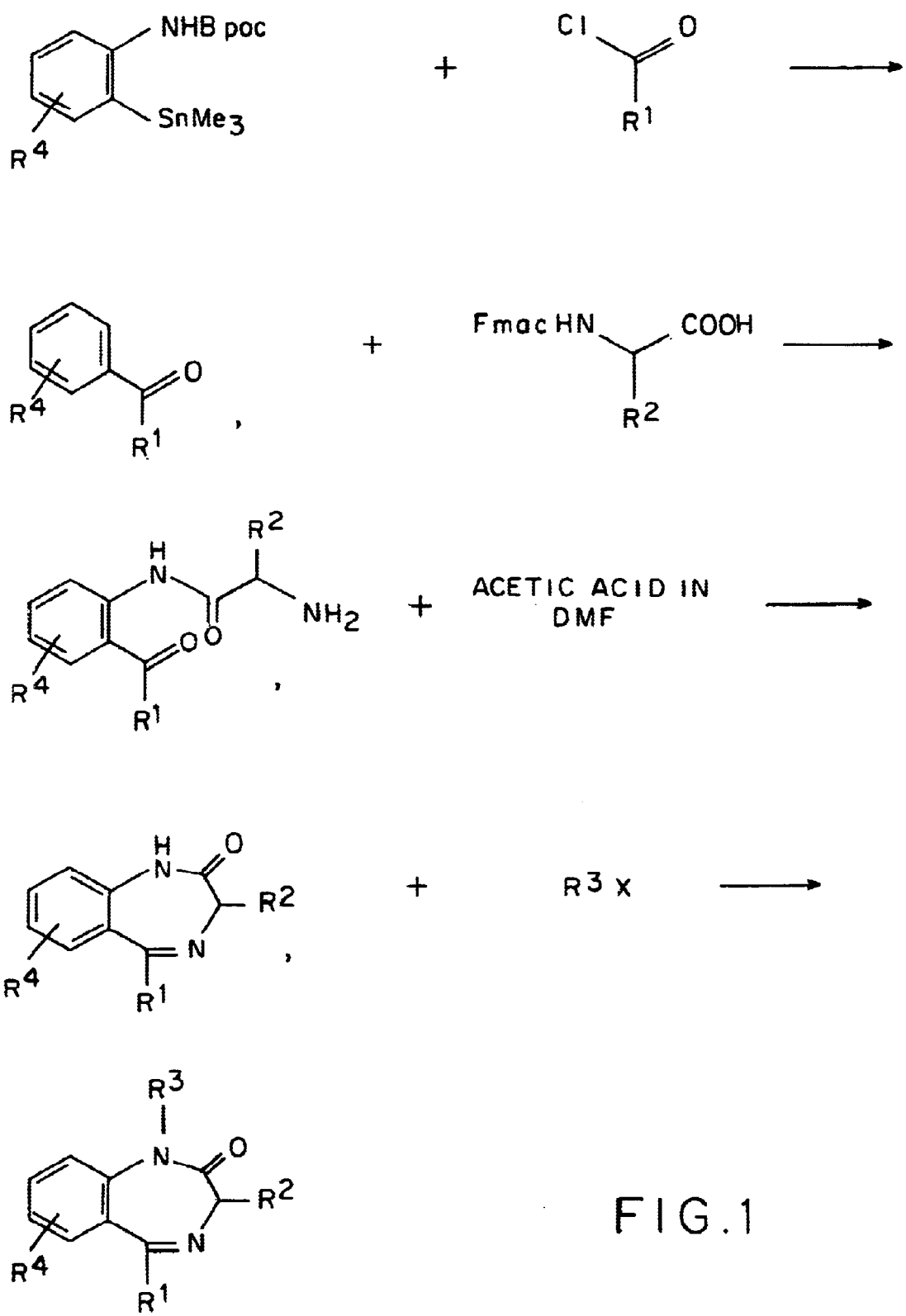
FIG. 1. Benzodiazepine scaffold used to create a combinatorial library, and a synthetic pathway leading to that structure.
Figure 2:
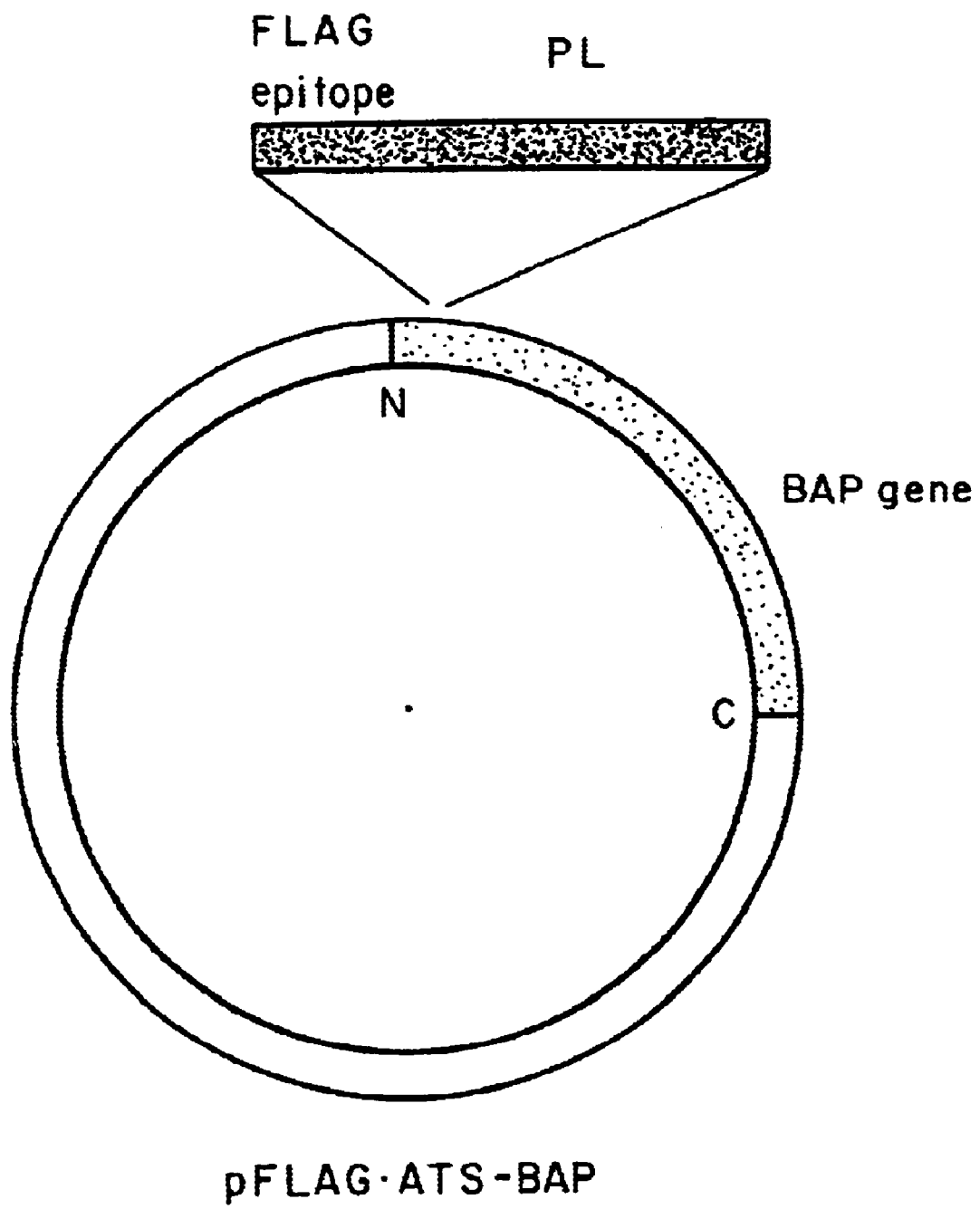
FIG. 2. Vector pFLAG-ATS-BAP for expression of peptide ligands fused to bacterial alkaline phosphatase. This vector has been used to successfully express both large and small domains of signaling proteins. In most instances the protein is secreted and one simply concentrates the fusion protein by ammonium sulfated precipitation from the media. In rare instances the protein is not secreted, but accumulates within the cells. In this case, we wash the cells in tris buffered saline then sonicate to release active fusion protein. In either instance, sufficient amounts of the material are obtained from 100 ml cultures. The FLAG epitope is disclosed, as a tag for a fusion protein, in Grihalde, et al., Gene, 166:187–95 (1995).

The basic library synthesis plan and member structure is shown in FIG. 1. The acid chloride building block introduces variability at the $R^1$ site. The $R^2$ site is introduced by the amino acid, and the $R^3$ site by the alkylating agent. The $R^4$ site is inherent in the arylstannane. Bunin, et al. generated a 1,4-benzodiazepine library of 11,200 different derivatives prepared from 20 acid chlorides, 35 amino acids, and 16 alkylating agents. (No diversity was introduced at $R^4$; this group was used to couple the molecule to a solid phase.) According to the Available Chemicals Directory (HDL Information Systems, San Leandro Calif.), over 300 acid chlorides, 80 Fmoc-protected amino acids and 800 alkylating agents were available for purchase (and more, of course, could be synthesized). The particular moieties used were chosen to maximize structural dispersion, while limiting the numbers to those conveniently synthesized in the wells of a microtiter plate. In choosing between structurally similar compounds, preference was given to the least substituted compound.

The variable elements included both aliphatic and aromatic groups. Among the aliphatic groups, both acyclic and cyclic (mono- or poly-) structures, substituted or not, were tested. (While all of the acyclic groups were linear, it would have been feasible to introduce a branched aliphatic). The aromatic groups featured either single and multiple rings, fused or not, substituted or not, and with heteroatoms or not. The secondary substitutents included —$NH_2$, —OH, —OMe, —CN, —Cl, —F, and —COOH. While not used, spacer moieties, such as —O—, —S—, —OO—, —CS—, —NH—, and —NR—, could have been incorporated.

Bunin et al. suggest that instead of using a 1,4-benzodiazepine as a core structure, one may instead use a 1,4-benzodiazepine-2,5-dione structure.

As noted by Bunin et al., it is advantageous, although not necessary, to use a linkage strategy which leaves no trace of the linking functionality, as this permits construction of a more diverse library.

Other combinatorial nonoligomeric compound libraries known or suggested in the art have been based on carbamates, mercaptoacylated pyrrolidines, phenolic agents, aminimides, N-acylamino ethers (made from amino alcohols, aromatic hydroxy acids, and carboxylic acids), N-alkylamino ethers (made from aromatic hydroxy acids, amino alcohols and aldehydes) 1,4-piperazines, and 1,4-piperazine-6-ones.

DeWitt, et al., Proc. Nat. Acad. Sci. (USA), 90:6909–13 (1993) describes the simultaneous but separate, synthesis of 40 discrete hydantoins and 40 discrete benzodiazepines. They carry out their synthesis on a solid support (inside a gas dispersion tube), in an array format, as opposed to other conventional simultaneous synthesis techniques (e.g., in a well, or on a pin). The hydantoins were synthesized by first simultaneously deprotecting and then treating each of five amino acid resins with each of eight isocyanates. The benzodiazepines were synthesized by treating each of five deprotected amino acid resins with each of eight 2-amino benzophenone imines.

Chen, et al., J. Am. Chem. Soc., 116:2661–62 (1994) described the prepartion of a pilot (9 member) combinatorial library of formate esters. A polymerbead-bound aldehyde preparation was "split" into three aliquots, each reacted with one of three different ylide reagents. The reaction products were combined, and then divided into three new aliquots, each of which was reacted with a different Michael donor. Compound identity was found to be determinable on a single bead basis by gas chromatography/mass spectroscopy analysis.

Holmes, U.S. Pat. No. 5,549,974 (1996) sets forth methodologies for the combinatorial synthesis of libraries of thiazolidinones and metathiazanones. These libraries are made by combination of amines, carbonyl compounds, and thiols under cyclization conditions.

Ellman, U.S. Pat. No. 5,545,568 (1996) describes combinatorial synthesis of benzodiazepines, prostaglandins, beta-turn mimetics, and glycerol-based compounds. See also Ellman, U.S. Pat. No. 5,288,514.

Summerton, U.S. Pat. No. 5,506,337 (1996) discloses methods of preparing a combinatorial library formed predominantly of morpholino subunit structures.

Heterocyclic combinatorial libraries are reviewed generally in Nefzi, et al., Chem. Rev. 97:449–72 (1997).

Examples of candidate simple libraries which might be evaluated include derivatives of the following:

Cyclic Compounds Containing One Hetero Atom

Heteronitrogen
        pyrroles
            pentasubstituted pyrroles
        pyrrolidines
        pyrrolines
        prolines
        indoles
        beta-carbolines
        pyridines
            dihydropyridines
            1,4-dihydropyridines
            pyrido[2,3-d]pyrimidines
            tetrahydro-3H-imidazo[4,5-c]pyridines
    Isoquinolines
        tetrahydroisoquinolines
    quinolones
    beta-lactams
    azabicyclo[4.3.0]nonen-8-one amino acid
    Heterooxygen
        furans
            tetrahydrofurans
                2,5-disubstituted tetrahydrofurans
        pyrans
            hydroxypyranones
            tetrahydroxypyranones
        gamma-butyrolactones
    Heterosulfur
        sulfolenes Cyclic Compounds with Two or More Hetero atoms Multiple heteronitrogens
        imidazoles
        pyrazoles piperazines
    diketopiperazines
    arylpiperazines
    benzylpiperazines
benzodiazepines
1,4-benzodiazepine-2,5-diones
hydantoins
    5-alkoxyhydantoins
dihydropyrimidines
1,3-disubstituted-5,6-dihydopyrimidine-2,4-diones
cyclic ureas
cyclic thioureas
quinazolines
    chiral 3-substituted-quinazoline-2,4-diones
triazotes
    1,2,3-triazoles
purines
Heteronitrogen and Heterooxygen
    dikelomorpholines
    isoxazoles
    isoxazolines
Heteronitrogen and Heterosulfur
    thiazolidines
        N-axylthiazolidines
    dihydrothiazoles
        2-methylene-2,3-dihydrothiazates
        2-aminothiazoles
    thiophenes
        3-amino thiophenes
    4-thiazolidinones
    4-melathiazanones
    benzisothiazolones For details on synthesis of libraries, see Nefzi, et al., Chem. Rev., 97:449–72 (1997), and references cited therein.

One or more moieties of the following types may be incorporated into compounds of the library, as many drugs fall into one or more of the following categories:

acetals
    acids
    alcohols
    amides
    amidines
    amines
    amino acids
    amino alcohols
    amino ethers
    amino ketenes
    ammonium compounds
    azo compounds
    enols
    esters
    ethers
    glycosides
    guanidines
    halogenated compounds
    hydrocarbons
    ketones
    lactams
    lactones
    mustards
    nitro compounds
    nitroso compounds
    organo minerals
    phenones
    quinones
    semicarbazones
    stilbenes
    sulfonamides
    sulfones
    thiols
    thioamides
    thioureas
    ureas
    ureides
    urethans Without attempting to exhaustively recite all pharmacological classes of drugs, or all drug structures, one or more compounds of the chemical structures listed below have been found to exhibit the indicated pharmacological activity, and these structures, or derivatives, may be used as design elements in screening for further compounds of the same or different activity. (In some cases, one or more lead drugs of the class are indicated.)

Hypnotics
    higher alcohols (clomethiazole)
    aldehydes (chloral hydrate)
    carbamates (meprobamate)
    acyclic ureides (acetylcarbromal)
    barbiturates (barbital)
    benzodiazepine (diazepam)

Anticonvulsants
    barbiturates (phenobarbital)
    hydantoins (phenytoin)
    oxazolidinediones (trimethadione)
    succinimides (phensuximide)
    acylureides (phenacemides)

Narcotic Analgesics
    morphines
    phenylpiperidines (meperidine)
    diphenylpropylamines (methadone)
    phenothiazihes (methotrimeprazine)

Analgesics, Antipyretics, Antirheumatics
    salicylates (acetylsalicylic acid)
    p-aminophenol (acetaminophen)
    5-pyrazolone (dipyrone)
    3,5-pyrazolidinedione (phenylbutazone)
    arylacetic acid (indomethacin)
    adrenocortical steroids (cortisone, dexamethasone, prednisone, triamcilone)
    athranilic acids Neuroleptics
    phenothiazine (chlorpromazine)
    thioxanthene (chlorprothixene)
    reserpine
    butyrophenone (halopendol)

Anxiolytics
    propandiol carbamates (meprobamate)
    benzodiazepines (chlordiazepoxide, diazepam, oxazepam)

Antidipressants
    tricyclics (imipramine)

Muscle/relaxants
    propanediols and carbamates (mephenesin)

CNS Stimulants
  xanthines (caffeine, theophylline)
  phenylalkylamines (amphetamine)
  (Fenetylline is a conjunction of theophylline and amphetamine)
  oxazolidinones (pemoline)
Cholinergics
  choline esters (acetylcholine)
  N,N-dimethylcarbamates
Adrenergics
  aromatic amines (epinephrine, isoproterenol, phenylephrine)
  alicyclic amines (cyclopentamine)
  aliphatic amines (methylhexaneamine)
  imidazolines (naphazoline)
Anti-adrenergics
  indolethylamine alkaloids (dihydroergotamine)
  imidazoles (tolazoline)
  benzodioxans (piperoxan)
  beta-haloalkylamines (phenoxybenzamine)
  dibenzazepines (azapetine)
  hydrazinophthalazines (hydralazine)
Antihistamines
  ethanolamines (diphenhydramine)
  ethylenediamines (tripelennomine)
  alkylamines (chlorpheniramine)
  piperazines (cyclizine)
  phenothiazines (promethazine)
Local Anesthetics
  benzoic acid
  esters (procaine, isobucaine, cyclomethycaine)
  basic amides (dibucaine)
  anilides, toluidides, 2,6-xylidides (lidocaine)
  tertiary amides (oxetacaine)
Vasodilators
  polyol nitrates (nitroglycerin)
Diuretics
  xanthines
  thiazides (chlorothiazide)
  sulfonamides (chlorthalidone)
Antihelmintics
  cyanine dyes
Antimalarials
  4-aminoquinolines
  8-aminoquinolines
  pyrimidines
  biguanides
  acridines
  dihydrotriazines
  sulfonamides
  sulfones
Antibacterials
  antibiotics
    penicillins
    cephalosporins
    octahydronapthacenes (tetracycline)
  sulfonamides
  nitrofurans
  cyclic amines
  naphthyridines
  xylenols
Antitumor
  alkylating agents
    nitrogen mustards
    aziridines
    methanesulfonate esters
    epoxides
  amino acid antagonists
  folic acid antagonists
  pyrimidine antagonists
  purine antagonists
Antiviral
  adamantanes
  nucleosides
  thiosemicarbazones
  inosines
  amidines and guanidines
  isoquinolines
  benzimidazoles
  piperazines For pharmacological classes, see, e.g., Goth, *Medical Pharmacology: Principles and Concepts* (C. V. Mosby Co.: 8th ed. 1976); Korolkovas and Burckhalter, *Essentials of Medicinal Chemistry* (John Wiley & Sons, Inc.: 1976). For synthetic methods, see, e.g., Warren, *Organic Synthesis: The Disconnection Approach* (John Wiley & Sons, Ltd.: 1982); Fuson, *Reactions of Organic Compounds* (John Wiley & Sons: 1966); Payne and Payne, *How to do an Organic Synthesis* (Allyn and Bacon, Inc.: 1969); Greene, *Protective Groups in Organic Synthesis* (Wiley-Interscience). For selection of substituents, see e.g., Hansch and Leo, *Substituent Constants for Correlation Analysis in Chemistry and Biology* (John Wiley & Sons: 1979).

The library is preferably synthesized so that the individual members remain identifiable so that, if a member is shown to be active, it is not necessary to analyze it. Several methods of identification have been proposed, including:

(1) encoding, i.e., the attachment to each member of an identifier moiety which is more readily identified than the member proper. This has the disadvantage that the tag may itself influence the activity of the conjugate.

(2) spatial addressing, i.e., each member is synthesized only at a particular coordinate on or in a matrix. This might be, for example, the location of a particular pin, or a particular well on a microtiter plate.

The present invention is not limited to any particular form of identification.

However, it is possible to simply characterize those members of the library which are found to be active, based on the characteristic spectroscopic indicia of the various building blocks.

Solid phase synthesis permits greater control over which derivatives are formed. However, the solid phase could interfere with activity. To overcome this problem, some or all of the molecules of each member could be liberated, after synthesis but before screening.

Screening of Compound Libraries

There are many suitable formats for carrying out efficient screens. The choice of format, in part, is dependent on the nature of the compound library being screened. Solid phase libraries consisting of compounds immobilized on pins or beads must be screened differently than compound libraries consisting of soluble compounds.

In general, assays for soluble compounds are composed of 1) an immobilized target and 2) a soluble, labeled ligand. The design of the assay is such that one measures the formation of PL/TP complex. Compounds that bind to the PL's cognate TP binding site (i.e. the FD) and prevent the binding of the PL and hence the formation of a PL/TP complex. Such interactions generally follow first order kinetics, that is, the amount of complex formed decreases with increasing amounts of compound. Compounds with potential utility shall display elements of "specificity. This means that useful compounds will inhibit the formation of one or only some PL/TP complexes, but not all.

It is necessary to establish assay kits which contain controls for the inhibition of the readout per se. For instance, if the readout of the amount of PL/TP complex formed is via an Elisa assay utilizing alkaline phosphatase, then it is necessary to be able to distinguish between a test compound's inhibition of the phosphatase versus inhibition of the PL/TP complex. NOTE: Because all screens established using this invention involve generically the same reagents i.e. PL and a protein target, there is an inherent advantage of the subject process since many functionally similar and dissimilar PL/TP complexes can be tested virtually simultaneously, so that the specificity of a given compound's activity can be determined with great easy.

In the specific instance of this invention, the target is the TP of interest and its cognate PL. Because the PL is a peptide, there are numerous means of labeling the PL. One very convenient means of labeling the peptide is to have it chemically synthesized with a biotin moiety attached to its amino or carboxy terminus. Preferable, the biotin moiety is separated from the peptide sequence identified above by the addition of one or more residues common in protein loops (reverse turns), or in interdomain spacers in natural multidomain proteins, e.g., glycine and serine residues. However, many permutations work well e.g. two glycines, G-S-G, S-G-S etc. The purpose is to have the biotin flexibly linked some distance away from the residues on the peptide that bind to the FD within the TP. Once the PL/TP complex is formed, it can be detected by a procedure using commercially available alkaline phosphatase-conjugated streptavidin to form a tertiary complex which is then detected through the use of soluble calorimetric substrates for alkaline phosphatase. Since the amount of substrate hydrolyzed per unit of time is a direct reflection on the amount of initial PL/TP complex present one can conveniently use a microtiter plate reader with kinetic capacity to estimate the inhibition of complex formation by a given compound without the requirement for testing multiple dilutions of a compound in the initial screen.

It is desirable to pre-complex the biotinylated peptide to the streptavidin complex. This reduces the number of steps required in the assay per se and by increasing the valency of the PL reagent, thus increasing the apparent avidity leading to a stronger signal to noise ratio. If the affinity of the PL/TP complex is especially low, it is preferable to use complexes with greater avidity e.g. the peptide can be complexed to dextran polymers (DEX) which have been pre-labeled with biotin as described by Dwyer (Nature Biotechnology, 14:348–351, Detection of Low Affinity Interactions between Peptides and Heat Shock Proteins by Chemiluminescence of Enhanced Avidity reactions (CLEAR), Leslie D. Causey and Donard S. Dwyer). This very nicely circumvents any need to laboriously seek out PL of high affinity for the TP.

An example of the results expected are shown below. In this experiment, About 100 ul of peptides conjugated to DEX (at a molar ratio of 5:1 to 10:1, diluted to 1.0 ug/ml) are brought into contact with recombinant GST fusions of the Target Proteins which have been coated onto standard low-background "ELISA" grade microtiter plates using the standard methods for binding antibodies. After 15 minutes, 100 ul of the diluted test compounds (10 micromolar in 5% DMSO in PBS, pH 7.4) are added to wells in the same position in each plate. After 15 minutes, the wells are washed several times with PBS and the amount of complex formed evaluated using calorimetric reagents. In the hypothetical examples below, numerical output from the microtiter plate reader has been scored as, full binding (+++), less binding (++), some binding (+) and no detectable binding (−).

TABLE I

Peptide Ligand One/Protein Target One tested against 18 compounds

| A1: +++ | A2: +++ | A3: +++ | A4: +++ | A5: +++ |
| B1: +++ | B2: +++ | B3: — | B4: +++ | B5: +++ |
| C1: +++ | C2: — | C3: +++ | C4: +++ | C5: +++ |
| D1: +++ | D2: +++ | D3: +++ | D4: +++ | D5: — |

+++: Complete complex formed. Wells A1 and D5 contain compound diluent but no test compound. No PL ligand is added to D5, thus any signal generated here is the result of non-specific background and is subtracted from the values for all wells.

TABLE II

Peptide Ligand Two/Protein Target Two tested against 18 compounds

| A1: +++ | A2: +++ | A3: +++ | A4: +++ | A5: +++ |
| B1: +++ | B2: +++ | B3: +++ | B4: +++ | B5: +++ |
| C1: +++ | C2: — | C3: +++ | C4: — | C5: +++ |
| D1: +++ | D2: +++ | D3: +++ | D4: +++ | D5: — |

+++: Complete complex formed. Wells A1 and D5 contain compound diluent but no test compound. No PL ligand is added to D5, thus any signal generated here is the result of non-specific background and is subtracted from the values for all wells.

TABLE III

Peptide Ligand Three/Protein Target Three tested against 18 compounds

| A1: +++ | A2: +++ | A3: +++ | A4: +++ | A5: +++ |
| B1: +++ | B2: +++ | B3: +++ | B4: +++ | B5: +++ |
| C1: +++ | C2: — | C3: +++ | C4: +++ | C5: +++ |
| D1: +++ | D2: +++ | D3: +++ | D4: +++ | D5: — |

+++: Complete complex formed. Wells A1 and D5 contain compound diluent but no test compound. No PL ligand is added to D5, thus any signal generated here is the result of non-specific background and is subtracted from the values for all wells.

Interpretation of Results: Since the compound added to well C2 prevented complex formation and/or blocked phosphatase label in all cases, it appears that it has non-specific effects. The compound added to wells B3 specifically blocks the formation of PL One/TP One complex; therefore, compound B3 appears to be a specific inhibitor of the binding site in the FD on TP One responsible for binding to PL One. Similarly, the compound in wells C4 specifically blocks the binding of PL Two to its cognate binding site in TP Two. In this assay, no compounds were observed to specifically block the interaction between PL Three and PT Three.

Compounds that interact with FDs on PTs can be identified directly by testing for direct PT binding to compound immobilized on a pin or bead. However, this is not advantageous. Firstly, it does not work well for "sticky" proteins. If the protein of interest binds to substrata e.g. plastic or amide resin with a high background, then it is difficult to detect specific binding. More importantly, because the compounds are synthesized on the pins or beads at a rather high density, then the protein target may bind due to a very high apparent avidity between the compound and the PT, thus the signal background is too high for reliable detection of suitable lead compounds. Finally, there is no convenient means to estimate affinity between the immobilized compound and the PT.

One can significantly improve upon direct binding assays, by using a labeled (to detect binding to the bead or pin) TP and test the specificity and affinity of the interaction of the TP and a given compound by specific inhibition by the appropriate PL. Here too, it is desirable to complex the peptide with dextran (average molecular weight ca. 6,000–8000) (about 10 peptides/mol). The dextran/PL complex is premixed with the labeled PT which are together brought into contact with the immobilized compound. The presence of the dextran per se minimizes the formation of non-specific complexes with the compound's plastic support and the dextran/PL complex modulates specific, high avidity binding of the labeled TP to the immobilized compound.

While compounds may be synthesized and evaluated immobilized to a matrix, their ultimate use will be in solution. Thus, having prepared PL cognates for the PT, one can evaluate putative inhibitory compounds for selectivity and specificity as described in the first example above.

Compounds can also be evaluated after synthesis on sheets of matrix e.g. derivatized plastic, nylon or nitrocellulose sheets using pre-labeled TP in a mixture of dextran/PL complex. The benefits to this method are that it lends itself to miniaturization and simple record keeping by having many samples on a single sheet. Once putative inhibitory compounds are identified, they can be synthesized in larger quantities for solution based studies such as those described above.

EXAMPLES

The following examples are given to further illustrate, but not limit, the invention.

Reference Example A

The Effect of Single Residue Biased Phage Display Libraries on the Selection of Binding Peptides Introduction Phage Libraries have been used as a means of displaying large collections of peptides while at the same time carrying the genetic information which encode them. This is a powerful tool for the discovery of peptide ligands for various molecules, however, it does have some limitations. At the present time it is possible to make libraries with a complexity on the order of $1-5\times10^9$ clones. It is technically feasible to make libraries with random stretches of 25 residues, however, in order to represent all possible combinations of amino acids, the length of the displayed peptide is limited to about 7 amino acids ($20^7$ or $1.28\times10^9$ possibilities). This may be sufficient for some interactions, however, some protein:peptide interactions may require more that a 7 amino acid peptide to accurately imitate the interaction of two proteins. We are thus forced to choose between using a library which represents all possible amino acid combinations with a peptide which may be sub optimal for binding or using a library which has the possibility of displaying a more optimal peptide at the cost of not having any of the binding peptides being represented.

To circumvent this problem we have taken a novel approach. The consensus sequences for ligands have at least one amino acid residue which is highly conserved. Purpose built libraries (i.e. a X-X-X-P-P-X-X-P-X-X (SEQ ID NO:13) library (Yu H, Chen J K, Feng S, Dalgarno D C, Brauer A W and Schreiber S L (1994) Cell 76:933–945)) based on consensus ligand sequences have been successfully used to isolate large numbers of phage displaying binding peptides using proteins in the same family. We theorized that libraries which have a single fixed residue flanked by regions coding for a random peptide should work in a similar fashion for targets for which no information on peptide ligands is available. If the fixed residue is important in the formation of a ligand, the number of phage which will display a peptide with binding characteristics will be enriched. Conversely, if the fixed residue is deleterious for the formation of a binding peptide, the number of phage in this library which display binding characteristics will be reduced.

We have tested this hypothesis using the SH3 domains from Abl and Src as targets, two domains for which a body of information exists on peptides which will bind. Ligands were screened for in libraries which display:

1) a completely random 12 amino acid peptide (random library),
2) four libraries having a peptide in which one fixed amino acid is flanked on each side by a random 5 mer (biased library) and
3) a $X_6PXPPXPX_2$ (SEQ ID NO:14) motif which conforms to the consensus for ligands that bind SH3 domain containing proteins (Class I SH3 purpose built library).

The four different biased libraries used contained a fixed proline, arginine, aspartate or phenylalanine residue. The predicted effect of the fixed proline was to be advantageous, the arginine and aspartate residues neutral, and the phenylalanine deleterious. The results indicate that the biased proline library was much more efficient than the random library and was almost as good as the purpose built library for isolating phage that bind specifically. The biased arginine library was more efficient than the random library and the biased aspartate and phenylalanine libraries were less efficient than the random library.

Methods

Phage were panned. Briefly, Src and Abl GST fusion proteins were immobilized on ELISA plates and blocked with BSA. Approximately $2\times10^{11}$ phage from each library was added to each well and allowed to bind. After washing the phage were eluted and amplified overnight in *E. coli* DH5αF'. The amplified phage were then put through 2 additional rounds of binding and elution without any amplification. Titers were approximated by spotting serial dilutions on a lawn of DH5αF'. Individual dilutions were then plated and clonal phage isolated by picking well separated plaques. Specificity was established using an anti-phage ELISA as previously described. Plates were coated with specific fusion protein or GST alone and phage bound as above. Bound phage were detected using an anti-phage antibody conjugated to horseradish peroxidase.

Results

Individual phage were isolated from each library for both proteins and the specificity of binding determined by anti-phage ELISA. The results are shown and discussed below.

Abl Binding Phage

The library that was most effective for isolating phage that bound specifically was the Class I SH3 purpose built: 10 out of 12 specific and of those 8 gave very strong signals indicating that the affinity is likely to be very high. The proline biased library was almost as effective with 7 out of 12 specific, all of them with very strong signals. The arginine biased library gave 6 out of 12 specific signals, however only two of those were of moderate strength. The aspartate biased library gave only one signal which was of moderate strength. The phenylalanine library gave signals which did not differ appreciably from background. The random library gave 12 out of 12 signals which were of low strength, indicating that they are likely not of very high affinity.

TABLE A-1

Phage isolated with Abl SH3 domain data

| Library | Strong Binding >1.75 OD | Weak Binding 0.5–1.74 OD | non-specific <0.5 OD |
|---|---|---|---|
| Random $X_{12}$ | 0 | 10 | 2 |
| $X_5FX_5$ | 0 | 0 | 12 |
| $X_5DX_5$ | 0 | 2 | 10 |
| $X_5RX_5$ | 2 | 4 | 6 |
| $X_5PX_5$ | 7 | 0 | 5 |
| $X_6PXPPXPX_2$ (Class I SH3) | 7 | 3 | 2 |

TABLE A-2

Phage isolated with the Src SH3 domain

| Library | Strong Binding >1.75 OD | Weak Binding 0.5–1.74 OD | non-specific <0.5 OD |
|---|---|---|---|
| Random $X_{12}$ | 3 | 0 | 2 |
| $X_5FX_5$ | 1 | 1 | 3 |
| $X_5DX_5$ | 4 | 1 | 0 |
| $X_5RX_5$ | 0 | 0 | 5 |
| $X_5PX_5$ | 4 | 1 | 0 |
| $X_6PXPPXPX_2$ (Class I SH3) | 3 | 0 | 2 |

Conclusions

The use of single residue biased libraries greatly enhances the isolation of phage displayed peptides which have desirable binding characteristics. In both cases, single residue biased libraries yielded a larger number of high affinity binders than the random library. This enhancement is both in the number of phage isolated and in the affinity that the phage have for the target. Furthermore, in each instance, the biased. libraries were as good as the so-called purpose built library. The purpose built library was made using a priori knowledge of the residues necessary for ligand affinity of the SH3 domain containing target.

This technique will be extremely valuable in the isolation of peptide ligands to proteins for which little or no information on the molecules with which they interact is available.

Example 1

Identification of Drugs for Treatment of Human Cytomegalovirus Infections

Human cytomegalovirus: disease associations. Human cytomegalovirus (HCMV) is a ubiquitous human pathogen (for recent reviews see Huang and Kowalik, 1993; Britt and Alford, 1996). HCMV is highly species specific. Humans are the only reservoir for the virus, and transmission occurs by direct or indirect contact among individuals. HCMV infections are generally asymptomatic in healthy children and adults. However, HCMV is responsible for about 8% of mononucleosis cases (Klemola et al., 1970; Horwitz et al., 1979) and for transfusion disease (Reyman, 1966) in some individuals that receive blood products contaminated with the virus. HCMV can cause serious disease in unborn children and in immunocompromised people.

HCMV is the most common congenital infection in humans (Britt and Alford, 1996); about 40,000 infected children are born each year in the United States. Given estimates that about 10–15% of these infected infants exhibit long-term neurological pathology, then HCMV is the leading infectious cause of central nervous system maldevelopment in newborn children (Fowler et al., 1992). Damage to perceptual organs is the most common outcome of intrauterine infection, and congenital HCMV infection appears to be the most common non-genetic cause of childhood hearing loss in the United States (Hicks et al., 1993).

HCMV disease is a common posttransplantation complication in solid organ allograft recipients. In general, the degree of immunosuppression in the allograft recipient correlates with the probability of clinically significant HCMV disease. More than 60% of heart, kidney and liver allograft recipients develop active HCMV infections (reviewed in Pollard, 1988; Britt and Alford, 1996). Solid organ allograft recipients exhibit a range of clinical syndromes resulting from HCMV infection, such as prolonged fever, leukopenia, thrombocytopenia, atypical lymphocytosis and elevated hepatic transaminases (Hofflin et al., 1987; Singh et al., 1988; Smyth et al., 1991) with life threatening complications that include severe infections of the gastrointestinal tract with perforations of abdominal viscera, hepatitis, and pneumonia (reviewed in Dummer, 1990; Smyth et al., 1991). Superinfection with fungal, protozoal and bacterial pathogens occurs late in the progression of HCMV disease (Chatterjee et al., 1978; Rand et al., 1978), possibly as a result of the ability of HCMV to suppress natural killer cell activity and T cell proliferation (Schrier et al., 1986).

HCMV infection is seen in about 40–50% of allogeneic bone marrow transplant recipients, and pneumonia is the most common clinical syndrome that results (reviewed in Wingard et al., 1990). Even with the availability of gangcyclovir, the mortality rate following bone marrow transplant remains at 10–20% for patients with HCMV pneumonia (Goodrich et al., 1991; Schmidt et al., 1991; Yau et al., 1991; Enright et al., 1993; Winston et al., 1993).

HCMV might be a cofactor in the pathogenesis of HIV. Epidemiological studies have suggested that HCMV infection is associated with increased risk for the development of AIDS in HIV-infected individuals (Webster et al., 1989; Webster, 1991; Webster et al., 1992). Although there is no direct evidence for such a role, there have been clear demonstrations that HCMV can influence HIV gene expression and growth in cultured cells (Barry et al., 1990; Rando et al., 1990; Biegalke et al., 1991; Koval et al., 1991; Peterson et al., 1992). In addition to its uncertain role as a cofactor in HIV progression, HCMV is a major life-threatening opportunistic infection in AIDS. Although HCMV disease in AIDS has been reported to affect almost every organ system, clinically significant HCMV infections have been reported most frequently in the central nervous system (principally retinitis which is found in 20–25% of long lived AIDS patients), the gastrointestinal system and the lung (Britt and Alford, 1996).

Prevention and treatment of human cytomegalovirus disease. Several recent reviews have described the different approaches to the prevention and treatment of HCMV disease (Coen, 1992; Britt and Alford, 1996).

Passive immunoprophylaxis using HCMV-specific immunoglobulin generally has not met with success as a therapy for established HCMV disease (Britt and Alford, 1996), and active immunoprophylaxis is also problematic. Attenuated HCMV vaccines have failed to provide protection in human trials (Stern, 1984; Plotkin et al., 1989). Furthermore, the use of live virus vaccines has met with safety concerns because of limited understanding of HCMV pathogenesis and virulence determinants and concerns about inoculation of women of childbearing age with a possibly teratogenic virus (Plotkin et al., 1990). Most recently there has been interest in developing subunit vaccines using individual HCMV proteins such as gB (Plotkin et al., 1990; Spaete, 1991).

Two well studied drugs have proven useful in the treatment of HCMV disease. Ganciclovir, a congener of acyclovir, and foscarnet both exhibit potent anti-HCMV activity in cell culture assays. Ganciclovir is preferentially phosphorylated in HCMV-infected cells by a viral gene product, UL97, and its subsequent incorporation into growing DNA chains by viral DNA polymerase encourages chain termination (Frank et al., 1984; Reid et al., 1988). Mutations in the viral polymerase or in UL97 confer resistance to ganciclovir (Sullivan et al., 1993; Baldanti, et al., 1995; Hanson, et al. 1995). Foscarnet inhibits the HCMV DNA polymerase directly (Snoeck et al., 1993). Numerous studies have demonstrated the efficacy of ganciclovir and foscarnet in the control of HCMV disease in both allograft recipients and AIDS patients (reviewed in Britt and Alford, 1996), although the utility of foscarnet is limited since its chronic use often leads to renal toxicity (Chrisp and Clissold, 1991; Reusser et al., 1992). In the case of AIDS, anti-HCMV drug therapy often must be continued on a long term basis since viral replication resumes shortly after withdrawal of the drug, and, as a consequence, viral variants that are resistant to one or both drugs are becoming increasingly common (Drew et al., 1991; Balfour, 1992), underscoring the need for additional drugs with anti-HCMV activity. Recently, a new drug with anti-HCMV activity was approved by the FDA for the treatment of retinitis in patients with AIDS. Vistide is a nucleotide analog which has performed well in clinical trials, although it can cause renal impairment.

One can envision many HCMV gene products that might be targets for the development of antiviral drugs. However, two HCMV proteins are most often cited as potential targets. The first is a proteinase encoded by the HCMV UL80 open reading frame and termed assemblin (Welch et al., 1991a and b). This proteinase functions during assembly of the virion particle. A temperature-sensitive allele of the homologous herpes simplex virus gene is defective for virus assembly at the nonpermissive temperature (Preston et al., 1983), predicting that a drug that interfered with the activity of assemblin, would block viral assembly and spread. The second target is the UL44-coded polymerase accessory protein. This protein, together with the UL54-coded polymerase, is the topic of this example.

Human cytomegalovirus DNA replication as a target for drug discovery. Currently available anti-HCMV drugs target the viral polymerase either directly or indirectly, validating HCMV DNA replication as a target for drug intervention. We propose to develop powerful screening assays for drugs that directly interfere with the processivity function of the HCMV-encoded DNA polymerase.

The approximately 230,000 base-pair HCMV genome is packaged into virions as a unit length, linear, double-stranded DNA molecule (reviewed in Mocarski, 1996). When the viral DNA enters a newly infected cell, it is believed to circularize (LaFemina and Hayward, 1983) and then replicate in the nucleus, producing huge concatemeric molecules. HCMV DNA replication requires both a cis-acting DNA origin of replication, termed oriLyt (Hamzeh et al., 1990; Anders et al., 1992; Masse et al., 1992), and a set of trans-acting viral proteins. Eleven trans-acting viral replication proteins have been identified (Pari and Anders, 1993; Pari et al., 1993) using a transient replication assay originally developed to study herpes simplex virus DNA replication (Challberg, 1986). In this assay, cells are co-transfected with a reporter plasmid containing the oriLyt sequence plus combinations of plasmids or cosmids that supply required viral trans-acting replication proteins. Replicated reporter plasmid DNA that is resistant to Dpn I is then monitored by DNA blot assay. The eleven HCMV products required for replication of the reporter are listed in Table 101. Five of the HCMV replication genes were originally identified on the basis of their sequence homology to known herpes simplex virus type 1 (HSV-1) replication proteins and on the basis of biochemical studies that confirmed predicted functions. These include a DNA polymerase, encoded by the UL54 HCMV open reading frame (Huang, 1975; Ye and Huang, 1993), and a polymerase accessory protein, UL44 (Ertl et al., 1991; Ertl and Powell, 1992); a single-stranded DNA-binding protein, UL57 (Anders et al., 1986; Kemble et al., 1987; Anders and Gibson, 1988); and putative helicase/primase proteins, UL105 and UL70 (Martignetti and Barrell, 1991; Chee et al., 1990). Further, it was noted that HCMV UL102 was located on the viral chromosome relative to other viral genes at a similar position as the HSV-1 UL8 gene encoding a primase associated factor (Chee et al., 1990), i.e., these genes were positional homologs. These proteins probably act directly at the replication fork to mediate HCMV DNA replication. Candidate homologs of this set of proteins have been found in all herpes viruses sequenced to date (EBV: Baer et al., 1984; VZV: Davison and Scott, 1986; HSV-1: McGeoch et al., 1988; HCMV: Chee et al., 1990; HVS: Albrecht et al., 1992; HHV6:), suggesting that they might represent a characteristic set of herpesvirus replication machinery proteins.

TABLE 101

Genes that are required for HCMV DNA replication when assayed by the transfection assay of Challberg (1986)

| HCMV Gene | Function | HSV Homolog | EBV Homolog |
|---|---|---|---|
| UL54 | Polymerase | UL30 | BALF5 |
| UL44 | Polymerase accessory factory | UL42 | BMRF1 |
| UL57 | ssDNA-binding protein | UL29 | BALF2 |
| UL105 | DNA helicase | UL5 | BBLF4 |
| UL70 | Primase | UL52 | BSLF1 |
| UL101–102 | Primase-associated factor | UL8 | BBLF2/3 |
| IE1/IE2 | Regulatory | none | none |
| UL84 | Binds IE2 | none | none |
| UL36–38 | Regulatory | none | none |
| UL112–113 | Regulatory | none | none |
| IRS1 | Regulatory | none | none |

Modified from Pari and Anders (1993). The indicated gene products were expressed under the control of their native promoters. The five regulatory components listed in the bottom portion of the table might serve entirely to activate expression of the five components listed at the top of the table that function directly in DNA replication (Iskenderian et al., 1996). Some of the genes listed in the table encode multiple polypeptides, e.g. UL112–113 encodes four polypeptides (Wright et al., 1988), and it is not yet known which members of the set are important for replication function. The Epstein-Barr virus (EBV) homologs listed have also been shown to be essential for complementation of lytic EBV replication (Fixman et al., 1992).

The IE1/IE2, UL36–38, and IRS1-TRS1 HCMV genes encode immediate early gene products have been shown to regulate the expression of viral and cellular genes at the level of transcription (e.g. Pizzorno et al., 1988; Cherrington and Mocarski, 1989; Depto and Stenberg, 1989; Stenberg et al., 1990; Colberg-Poley et al., 1992; Stasiak and Mocarski, 1992). The UL84 and 112–113 genes encode early viral proteins with unknown functions (Wright et al., 1988; He et al., 1992). Although no effect on transcriptional regulation has been observed, the UL84 protein has been shown to bind to the IE2 protein (Spector and Tevethia, 1994) and therefore might somehow modulate its transcriptional regulatory function. Recently, Iskenderian et al. (1996) demonstrated that the combination of IE1/IE2, UL36–38, IRS1, and UL112–113 cooperated as a group to more effectively activate expression from several HCMV promoters controlling HCMV replication proteins. Thus, these proteins as well as UL84 might serve to facilitate expression of the set of HCMV proteins that act at the replication fork.

The studies on HCMV replication failed to identify a homolog of the HSV-1 UL9 protein which is required for HSV-1 DNA replication. This is not surprising since this protein binds in a sequence-specific fashion to the HSV-1 origin of DNA replication (Elias et al., 1986; Koff and Tegtmeyer, 1988). The HSV-1 UL9 protein together with the six HSV proteins identified in Table 101 are necessary and sufficient to reconstitute HSV-1 DNA replication in the transfection assay (Challberg, 1986) described above. Thus, it is highly likely that all HCMV proteins that participate directly in viral replication, with the exception of an origin-binding protein, have been identified. If HCMV utilizes an origin-binding protein, it presumably is one of the 11 proteins identified in Table 101.

Of particular interest to this example is the HCMV UL44 protein. As mentioned above, this protein is generally referred to as the DNA polymerase accessory protein. The HCMV UL44 protein has some homology to the HSV-1 UL42 protein (data not shown). Both of these proteins exist in a 1:1 complex with viral DNA polymerase (UL42: Powell and Purifoy, 1977; Gallo et al., 1988, Crute and Lehman, 1989; UL44: Huang, E.-S., 1975; Ertl and Powell, 1992). The HSV-1 UL42 protein has been shown to be essential for viral DNA replication by analysis of viral mutants (Johnson et al., 1991; Digard et al., 1993), and the HCMV UL44 protein has been shown to be essential for viral DNA replication in antisense experiments (Ripalti et al., 1995). Mutations that disrupt the HSV-1 polymerase-processivity factor interaction block virus DNA replication, arguing that: the interaction is required for DNA replication (Digard et al., 1993a and b; Reddig et al., 1994), reinforcing the conclusion that the polymerase-processivity factor interaction is essential for viral growth. Amino acids at the extreme C-terminus of the polymerase (Digard and Coen, 1990; Digard et al., 1993a; Stow, 1993; Tenny et al., 1993; Digard et al., 1995) and two distinct regions within the HSV-1 processivity factor (Monahan et al., 1993) have been shown to be important for the interaction.

Biochemical studies have established that the HSV-1 UL42 and HCMV UL44 proteins dramatically enhance the processivity of the viral polymerases by discouraging dissociation of the enzyme from the growing DNA strand's terminus (Gottlieb et al., 1990; Hernandez and Lehman, 1990; Weiland et al., 1994). Therefore, agents that destabilize the interaction of the processivity factor with the polymerase, interfere with the interaction of the processivity factor with DNA (the processivity factor was first identified as a DNA-binding protein), or otherwise perturb the function of the processivity factor are very likely to interfere with viral DNA replication. As a result, such agents could likely interfere with viral replication; and, therefore, would be candidate anti-viral drugs.

The goal of this example is the development of a high throughput screen for the identification of small molecule anti-HCMV drug candidates that target the viral UL44 processivity factor. We will focus on the DNA synthesis processivity factor, UL44; however, the Combinatorial Recognition system can be readily applied to other viral proteins. This drug discovery system is especially useful for proteins that are not readily placed into biochemical assays, e.g. regulatory factors. We chose to use UL44 as a target for our combinatorial recognition system because it is known to be necessary for viral replication and in vitro synthesis of CMV DNA. Thus, we can rapidly evaluate the action of any potential compounds that act on UL44 with both biochemical and viral replication assays.

What advantages are provided by using Combinatorial Recognition to identify inhibitors of HCMV replication? Assays for viral factors such as the UL44 processivity factor are difficult and expensive to automate. Presently, the action of the processivity factor is measured by running a sample for each time point on an agarose gel. High throughput assays for other viral regulatory proteins are virtually impossible to design. However, the process we describe below can provide high throughput screens for many viral proteins.

Experimental Design and Methods
Cloning and Expression of UL44

The first step is production of recombinant protein to use as a molecular affinity selection tool. We have found that fusions to glutathione-S-transferase (GST) are easily constructed and efficiently produce the desired protein products.

Like most HCMV mRNAs, the mRNA encoding UL44 is not spliced. Therefore, it is possible to isolate the complete UL44 coding sequence as a functional unit from HCMV genomic DNA prepared from purified virions. We have used the following oligonucleotide primers and the PCR to amplify the coding region of UL44 from CMV DNA: 5'-CTGTGCGGATCCATGGATCGCAAGACG-3' (SEQ ID NO:15) and 5'-CTGTGCGAATTCCTAGCCGCACTTTTG-3' (SEQ ID NO:16). The resulting 1.3 kb product was purified using a WIZARD PCR PREPS clean up resin, blunted with T4 DNA Polymerase (NEB), cut with BamHI repurified on an agarose gel and cloned into the vector pGex2T digested with BamHI and SmaI. Individual clones were tested for the correct insert by restriction enzyme digests and two clones were sequenced in entirety to insure the correct protein was encoded by the clone. *E. coli* DH5aF' carrying the plasmid were induced with IPTG to produce the fusion protein and the product was purified by affinity chromatography using glutathione SEPHAROSE matrix as recommended by the manufacturer (Pharmacia). The resulting protein was used as a fusion protein or was cleaved from the glutathione SEPHAROSE chromatography matrix using the protease thrombin (which cleaves between the GST portion of the fusion and the UL44 protein) by treating 1 mg of fusion protein on beads with 50 Units of Thrombin (Pharmacia) for 2 hours at room temperature. The resulting UL44 protein was analyzed by SDS gel electrophoresis and contained two major cleavage products, one of full length and the other roughly 5 kdaltons smaller.

Phage Libraries

Phage libraries were made using published protocols (Construction of Random Peptide Libraries in Bacteriophage M13 in Phage Display of Peptides and Proteins: A Laboratory Manual. Edited by B. Kay, J. Winter and J.

McCafferty. Academic Press 1996.). Briefly, oligonucleotides which encoded the random peptide with one residue fixed were converted to double stranded DNA by extending a complementary primer using SEQUENASE modified T7 DNA polymerase (USB). The resulting fragments were digested with XhoI and XbaI, gel purified and ligated into previously digested mBAX vector. The ligation was introduced into bacteria by ten successive electroporations and the transformed bacteria were amplified overnight. The supernatant containing phage was harvested and the phage precipitated using PEG/NaCl, resuspended in 1× PBS containing 10% glycerol and frozen at −80° C. Ten of the oligonucleotides encoded peptides with the following structure: $X_5UX_5$ where X is any amino acid and U is a fixed residue. The following residues were fixed, one in each library: D(GAT), F(TTC), H(CAC), K(AAA), L(CTG), M(ATG), N(AAT), P(CCG), R(CGT), and W(TGG). For convenience, the $X_5DX_5$ library is referred to as a "D" library, $X_5FX_5$ as an "F" library, etc. The oligonucleotide sequence for each was 5'-GACTGTGCCTCGAGK(NNK)$_5$xxx(NNK)$_5$TCTAGACGTGTCAGT-3' (SEQ ID NO:17) where xxx is the codon shown above for each residue fixed. In addition, a library with 10 random residues followed by a fixed C (TGC) was constructed with the same flanking sequences. This is referred to as the "$X_{10}C$" library. The oligonucleotide with the sequence of 5'-ACTGACACGTCTAGA-3' (SEQ ID NO:18) was used as the primer to convert the ssDNA to double stranded.

The Carolina Workshop Library (CWL) is a 12-a.a. "unbiased" (no constant residue) peptide phage library, with each amino acid encoded by NNK.

Affinity Selection of Phage Specific for UL44

UL44 or GSTUL44 was immobilized on microtiter plates (Costar) by incubating 1 μg of protein in 200 μl of 0.1 M NaHCO$_3$, pH 8.5 overnight at 4° C. The remaining protein binding sites on the plate were blocked by adding 150 μl of 1% BSA in 0.1 M NaHCO$_3$ and incubating the plate at room temperature for 1 hour. The plate was then washed 5 times with 300 μl of TBST (100 mM Tris-Cl, pH 7.5, 150 mM NaCl, TWEEN detergent). Phage libraries were then added to the wells in 200 μl of TBST and allowed to incubate at room temperature for 5 hours. The wells were washed 5× with TBST and the phage were eluted by incubating with 200 μl of 50 mM Glycine, pH 2.0 for 10 minutes. The eluant was removed to a tube at the pH neutralized with 200 μl of 200 mM NaHPO4 buffer, pH 7.0. The phage were then amplified by adding the eluted phage to 5 ml of 2XYT broth containing 1:100 dilution of an overnight culture of E. coli DH5αF'. The cultures were grown with agitation overnight at 37° C. The next morning the bacteria were removed by centrifugation at 3000 ×g for 10 minutes in a SS-34 rotor. 100 μl of the supernatant containing the amplified phage were then used in the next round of affinity purification.

Enrichment for phage that bind to UL44 were monitored by including a non-specific phage which formed white plaques on DH5αF' in the affinity selection process starting at round 2. Upon plating each round of selection, the ratio of blue:white plaques was monitored by plating the phage in the presence of X-gal and IPTG. Phage from our libraries appear blue and the non-specific control phage appear as white plaques. If a particular library has been enriched for phage which bind to the target, then they should be selectively retained in higher numbers than the control phage and this is reflected in the ratio of blue to white plaques (FIG. 5). Based on this data we tested individual isolates from the D, F, N, W, $X_{10}C$, and CWL (Carolina Workshop Library) libraries when GSTUL44 was used as the target protein. 87 out of 96 phage bound to GSTUL44, and of these 86 bound to other GST fusion proteins while one was specific for the GSTUL44 fusion. Thus it is relatively easy to obtain phage expriessing peptides which recognize the GST moiety of the fusion protein. However, we are also able to isolate phage specific for the UL44 portion of the protein, showing that we are targeting multiple domains on a single polypeptide.

To increase the number of phage isolated which bind to the UL44 portion of the fusion protein, we cleaved the fusion with thrombin and used the free UL44 as a target for our selection process. To assess the distribution of binders across all of the libraries, we tested 16 individual phage from each library. Most of the phage exhibited specific binding to UL44, however, phage from the $X_{10}C$ library gave much stronger signals in the phage ELISAs (FIG. 6).

To determine how specific the phage were for UL44 we assessed the binding of 23 of the isolates against a variety of other targets. Two populations of phage were found: the first recognized thrombin cleaved UL44 and GSTUL44 while the second group recognized only thrombin cleaved UL44. All 23 of these phage were subjected to automated DNA sequencing analysis and the results are shown below.

Isolated from panning against GSTUL44 and thrombin cleaved UL44 on IMMULON4R microtitration test plates as well as thrombin cleaved GSTUL44 on COVALINK[4] microbiological and immunological analysis plates

```
X10C      E H V C S W G W G R C    (SEQ ID NO:19)

other not from X10C:

17        P T S D L W R N L G G    (SEQ ID NO:20)

18        W G E T M W D N R K V    (SEQ ID NO:21)

11        A G L T P W S L L V D    (SEQ ID NO:22)

many clones

8H        D T G T W W H S Y V L    (SEQ ID NO:23)

2A        R A P L A D R L L E G    (SEQ ID NO:24)

2E        K L W S A D M S S I V    (SEQ ID NO:25)

2H        F I V G N D Y R L G K    (SEQ ID NO:26)

8B        E G Y P S W V Y M G M    (SEQ ID NO:27)

1E        A R D F E D V Q Q C C    (SEQ ID NO:28)
```

Two important points are illustrated in the sequence analysis. First, regardless of how we immobilized the target we continually isolated phage from the $X_{10}C$ library expressing the exact same peptide. These phage have identical DNA sequences and due to the complexity of the library and the sequences which are theoretically possible, it is quite likely that we continually isolated the exact same phage. Phage expressing this peptide bind to both GSTUL44 and thrombin cleaved UL44. Second, phage in from the second group represent a diverse population which only recognize the thrombin cleaved GSTUL44. None of these peptide sequences appear related to any known proteins in Genbank or the SWISS-PROT databases.

To demonstrate that the phage isolated in this screen were specific for a biologically relevant site and that they are targeting distinct sites on the protein, we carried out competition experiments between phage which recognize the GST portion of the protein and glutathione (GSH). To map the. binding site for the UL44 specific phage displaying the constrained peptide from the $X_{10}C$ library, we competed this phage for binding with linear double stranded DNA. To show the specificity of binding for the substrates and the phage, both phage were competed with both substrates. Microtiter plates were coated with GSTUL44 protein and blocked as described above. Phage specific for either the GST portion or the UL44 portion of the fusion were then added to separate wells and at the same time various concentrations of either GSH or DNA were added. The results are shown in FIG. 7. It is important to keep in mind that these phage were isolated from the same affinity selection run. This clearly shows that phage specific for GST bind at the active site of the enzyme because the binding of phage is competed in a dose dependent fashion with GSH. The concentrations of GSH used here had no effect on the binding of the UL44 specific phage to the same GSTUL44 protein. Conversely, the phage specific for UL44 are binding in the DNA binding pocket of UL44 and are competed away by the addition of DNA in a dose dependent manner. The same concentrations of DNA have little effect on the binding of the GST specific phage to the same GSTUL44 fusion protein.

Enzyme Linked Spectrophotometric Assay (ELSA) for CMV UL44 Using Peptides Derived From Phage Display IMMULON-4 (cat.#011-010-3855) 96-well microtitration test plates were purchased from Dynatech. Bovine serum, albumin (BSA) (A2153), Streptavidin alkaline phosphatase (SA-AP) (S2890), TWEEN-20 detergent (P1379), and p-nitrophenyl phosphate tablets (pNPP) (N-1891, N-2770) were purchased from Sigma. Phosphate buffered saline (PBS) (21600-010) was obtained from Gibco-BRL. Ultrapure glycerol (#16374) was purchased from USB. Biotinylated surrogate ligands were prepared as a 1 mM stock solution in the appropriate solvent ($H_2O$ or 10% acetonitrile). SA-AP was prepared as a 1 mg/ml stock solution in PBS containing 10% glycerol and stored in aliquots at −80° C. Peptides corresponding to peptides displayed on the surface of binding phage (H-Ser-Gly-Ser-Gly-Glu-His-Val-Cys-Ser-Trp-Gly-Trp-Gly-Arg-Cys-OH (SEQ ID NO:29) and Biotin-H-Ser-Gly-Ser-Gly-Glu-His-Val-Cys-Ser-Trp-Gly-Trp-Gly-Arg-Cys-OH) (SEQ ID NO:30) (the underlined residues were from the $X_{10}C$ peptide listed above; the Ser-Gly-Ser-Gly unit is a linker) were synthesized by AnaSpec, Inc.

Target protein was immobilized in microtiter wells by incubating 0.5–2.0 μg per well in 100 μl of 0.1 M $NaHCO_3$ overnight at 4° C. (Studies have indicated that maximal protein binding can be attained with 0.5 μg of target protein per well.) The target protein was removed and the wells were blocked with 200 μl of 1% BSA prepared in 0.1 M $NaHCO_3$ for 1 hour at room temperature. During the 1 hour blocking period, the SA-AP:surrogate ligand conjugate was prepared by mixing 2 μg SA-AP and 50 pmol biotinylated surrogate ligand for each well of target protein. (This corresponds to a 1:1 ratio of biotinylated peptide to biotin binding sites.) The mixture was incubated at room temperature for 15–20 minutes and then diluted with Tris-buffered saline-TWEEN-20 detergent (TBST) 10 mM Tris-HCl, pH 8.0, 150 mM NaCl, 0.05% TWEEN-20 detergent such that there was 100 μl of conjugate per well. For lower concentrations of surrogate ligand, an unrelated biotinylated peptide was titrated in to keep the total amount of biotinylated peptide at 50 pmol/well and total SA-AP at 2 μg/well. After blocking, the wells were washed once with 200 μl TBST. The surrogate ligand:SA-AP conjugate was then added (100 μl/well) and incubated at room temperature for 2 hours. The wells were then washed 5 times with 300 μl TBST using a BioRad 1575 Immunowash plate washer. The assay was developed by adding 100 μl of pNPP and incubating at room temperature for 5–10 minutes. The absorbance was read at 405 nm.

FIG. 8 shows that a peptide derived from phage display binds specifically to UL44. The only significant binding is to GST-UL44 and not to streptavidin, GST or a GST-SrcSH3 fusion protein, indicating that the structure recognized by this peptide is UL44 and not the GST tag. This binding is time and dosage dependent (FIGS. 9 and 10). The binding is dependent on the concentration of the surrogate ligand and the concentration of target protein on the plate. Saturation of the target protein binding to the plate occurs at about 0.5 μg of protein per well. The binding of this peptide to UL44 can be competed specifically with an identical-peptide that is not biotinylated (FIG. 11).

Conclusion:

We have isolated phage displaying peptides from biased peptide libraries which bind specifically to a GSTUL44 fusion protein. These phage bind to one of two domains: the GSH binding site on the GST portion of the fusion or the DNA binding site on the UL44 fusion. The phage are specific for each site and they can be competed for binding with their respective ligands. A peptide of the same sequence as the phage which binds to the DNA binding domain of UL44 also binds to UL44 specifically. This binding can be demonstrated by a competition assay between the peptide and the parent phage or by using a biotinylated peptide which is then detected using a streptavidin-alkaline phosphatase conjugate (SA-AP).

This conjugate could be used to screen through large numbers of low molecular weight compounds to find those that bind at the DNA binding site of UL44. This could be done several ways. The first approach is using the assay shown here. First the target protein, in this case UL44 or a UL44 fusion protein would be immobilized on a solid surface (i.e. a microtiter plate). The peptide would be complexed with SA-AP and, this complex added to a well containing the immobilized target at the same time that a small molecular weight compound is added. After allowing time for binding, the wells would be washed with buffer and the substrate for the conjugate (PNPP) could be added and allow for any conjugate in the well to convert the clear substrate to the colored product. The amount of color is proportional to the amount of SA-SP in the well. If a small molecular weight compound bound to the target at the same place as the surrogate ligand:SA-AP complex, then a reduced amount of color would be detected because the compound and the peptide:SA-SP complex can not occupy the same space. This would be the identification of a potential drug lead. This method could be used in an automated format to screen large numbers (from 1,000 to 1,000,000) of compounds for those which have the property of binding to a target in the same place as the surrogate ligand and preventing the labeled surrogate ligand from binding to the target. This may be done in such a way that the compounds are added first and allowed to bind before the addition of surrogate ligand or conversely the surrogate ligand may be bound to the target first and the compounds added after and the displacement of surrogate ligand monitored. The peptides here could be used in a precomplexed format (as shown above) or they may be used as monomeric ligands and then detected in a second step.

This example illustrates the use of phage display to isolate surrogate ligands targeted to a biologically relevant site on a viral protein and the utility of using this ligand in a high throughput screen of small molecules for the discovery of potential therapeutic drug leads. Similar experiments can be done with any viral protein which is a target for antiviral therapy. This would include proteins from CMV as well as other herpes viruses, but also proteins from any other virus regardless of classification or mode of propagation. All that is required is a source of the viral protein. In this case the protein was produced by cloning and expressing the target in bacteria. The cloned protein could be expressed in any system including but not limited to bacteria, yeast, baculovirus, vaccinia virus, CHO cells (chinese hamster ovary cells), HeLa, fibroblasts, adenovirus or any other expression system in which the target protein is produced in such a way that it presents an active conformation to the potential surrogate ligands. The protein could also be made in vitro by transcription and translation using any of a variety of RNA polymerases in conjunction with lysates from reticulocytes, wheat germ or any other source of enzymatic machinery for the translation of RNA to protein. If the target protein were small enough or if a synthetic scheme could be devised to produce it de novo, the target could also be a completely synthetic molecule.

Biological Activity Testing (Prophetic)

As discussed above, peptides generally do not cross the plasma membrane of cells. Although technology is available to deliver peptides into cells with high efficiency using liposomes, electroporation, micro-injection, etc., we plan to use an assay that does not depend on the intracellular delivery of peptides as our initial method to evaluate the physiological effect of the peptides that interact with the processivity factor. This in vitro assay was originally developed in the HSV-1 system (Hernandez and Lehman, 1990), and we will adapt and validate the assay for the HCMV replication system. The in vitro HSV-1 system utilizes three virus-coded proteins: the DNA polymerase (HSV UL30), the processivity factor (HSV UL42), and the single-stranded DNA-binding protein (HSV UL29). The template used for the in vitro replication system is single-stranded M13mp18 DNA to which an oligonucleotide primer (5'-GTTTTCCCAGTCACGAC-3') (SEQ ID NO:31) is annealed. The oligonucleotide is generally used for DNA sequencing and is commercially available (New England BioLabs). Thus, the replication assay is an origin-independent primer extension reaction. The HSV-1 polymerase and single-stranded DNA-binding protein extend the primer annealed to M13 DNA, producing chains of variable length and only a small quantity of completely double-stranded DNA where the primer has been extended the full length of the M13 circular DNA. In contrast, with addition of the processivity factor, most of the product is full length, double-stranded M13 DNA. The production of variable length versus full length DNA products is monitored by the electrophoretic separation of reaction products in agarose gels (Hernandez and Lehman, 1990).

Ertl and Powell (1992) showed that the HCMV polymerase and processivity factor, purified as recombinant proteins from baculovirus-infected Sf9 cells, cooperate in a primer extension reaction, and they further demonstrated that the processivity factor stimulated the activity of the polymerase in the assay. Similarly, Weiland et al., (1994) have shown that recombinant HCMV UL44 processivity factor produced in *E. coli* can enhance the activity of HCMV DNA polymerase in a primer extension assay. We will implement the origin-independent primer extension assay in the HCMV system as follows. The coding sequence for the HCMV polymerase (UL54) and single-stranded DNA-binding protein (UL57) will be amplified from HCMV genomic DNA as described above for the processivity factor (UL44). The UL54 and UL57 coding regions will be validated by automated DNA sequence analysis, and cloned into pBlueBacHis2 (Invitrogen). The plasmids will then be used to construct baculovirus recombinants for expression of the replication proteins in Sf9 insect cells. Expressed proteins carry two tags at their 5' ends, one the Xpress leader peptide (Asp Leu Tyr Asp Asp Asp Asp Lys) (SEQ ID NO:178) is easily detected with a monoclonal antibody in ELISA assays and the other includes a six histidine binding site that has a high affinity for divalent cations. Nickel-chelating resins will allow us to purify the recombinant proteins in one step. The HCMV equivalent of the HSV-1 replication assay will then be optimized using purified proteins.

When we have successfully implemented the in vitro origin-independent primer extension assay, we will titrate peptides that we have shown to interact with the processivity factor into the reaction to test for their ability to perturb the interaction. It is possible that most if not all peptide-processivity factor interactions will be of considerably lower affinity that the polymerase-processivity factor or DNA-processivity factor interaction, but we can use a vast excess of the peptide to drive the peptide interaction to search for effects. We can also vary the order of addition of reactants to give the peptide an opportunity to interact with the processivity factor before the addition of other factors. We anticipate that some of the peptides will interfere with the essential interactions of the processivity factor; and, as a result, will inhibit processivity in the primer extension reaction. The specificity of inhibitory effects will be assayed by testing the ability of active peptides to inhibit the activity of mammalian DNA polymerase alpha (partially purified from HeLa cells by sequential chromatography on Q-SEPHAROSE chromatography matrix and double-stranded DNA cellulose, Owsianka et al., 1993) or the *E. coli* Klenow polymerase (commercially available) on the M13-primer complex. There is precedent for this type of assay in the HSV-1 system. Owsianka et al. (1993) assayed a series of 15-mer peptides corresponding to segments of the HSV-1 processivity factor (the opposite 'sense' to our peptides that will bind to the processivity factor), and identified one peptide that inhibited a primer extension reaction and exhibited some specificity for the viral as compared to the cellular DNA polymerase. The peptides that inhibit the HCMV replication reaction would then be used in high throughput peptide displacement screens for identification of small molecules from combinatorial libraries with the potential to interfere with processivity in phase II of this proposal.

We are confident that the in vitro origin-independent primer extension assay can be established to monitor processivity of the HCMV polymerase given the analogous nature of the HSV-1 and HCMV polymerase/processivity factor complexes and the reports of Ertl and Powell (1992) and Weiland et al. (1994) who used very similar systems. If, however, the recombinant proteins do not appear to be active, we would initially suspect that the 5' epitope tag is interfering with function. To address the potential problem, we would remove the epitope tags with enterokinase cleavage, and if that does not yield functional products, we would purify untagged proteins from insect cell extracts using standard chromatographic procedures, as was done for the HSV-1 proteins (Hernandez and Lehman, 1990) and subsequently for the HCMV proteins (Ertl et al., 1991; Ertl and Powell, 1992). In the unlikely event that we are unable to produce active HCMV proteins, we will consider two alternative approaches. It has been shown in the HSV-1 system that extracts of insect cells can sponsor origin-independent replication of circular plasmid templates when the insect cells have been infected with a mixture of baculoviruses expressing polymerase, processivity factor, single-stranded DNA-binding protein and helicase/primase complex (Skaliter and Lehman, 1994). To implement this assay, we would clone the HCMV helicase/primase subunits (UL105, UL 70, UL 101–102) into baculovirus vectors, infect with the mixture of baculoviruses expressing the HCMV proteins equivalent to the HSV-1 proteins listed above, produce extracts and test their activity. Peptides could then be tested for their ability to inhibit origin-independent replication in the extracts. Alternatively, cells could be infected with a set of plasmids expressing the complete set of eleven factors needed to reconstitute HCMV oriLyt-dependent replication (Pari and Anders, 1993; Pari et al., 1993). Peptides would be introduced into cells by electroporation, which has been used to introduce functional small polypeptides into cells with high efficiency (Kashanchi et al., 1992) and tested for their ability to inhibit the reaction.

Screening Small Molecule, Combinatorial Chemical Libraries for Compounds that Bind Specific Functional Domains of HCMV UL44. (Prophetic)

Combinatorial chemical libraries will be screened to identify compounds that block macromolecular interactions of UL44. We will screen the benzodiazepine library described above and other chemical diversity libraries.

The compound libraries will be screened by placing individual compounds in microtiter plates wells that have-.been coated with GST-UL44 fusions and adding the molecular probe. While one can use biotinylated peptides as probes within screening assays, we have found that this can be made much more "user friendly" for compound screening by using an expression vector pMY to which peptides or protein modules can be fused to bacterial alkaline phosphatase (BAP) (described above). The BAP fusion protein retains the activity of both the enzyme and the peptide or domain. We will fuse a representative member of each class of UL44 peptide ligands to the BAP protein (by inserting fragments of DNA assembled from oligonucleotides) and then use the fusion protein to assemble a high-throughput screening assay. If the compound competitively inhibits the binding of the BAP-ligand fusion to the immobilized UL44 protein the well will remain clear during color development; on the other hand, if the compound fails to bind to the domain then the BAP-ligand fusion protein will bind to the immobilized target leading to the development of an intense yellow color.

Because the Ligand/BAP fusion protein also encodes the FLAG epitope, we include as a control well for each compound examined a test for any apparent non-specific activities by examining the effects of the compound upon binding the Ligand/BAP fusion to immobilized anti-FLAGC mAb M1.

Once specific compounds with binding activity have been identified they will be characterized in extensive biochemical and viral growth studies. Among our goals is the identification of lead compounds that act at each of the UL44 functional domains. If we achieve this, then we shall test combinations for synergistic activity.

Subsequently the program will progress to the development of second-generation combinatorial chemical minilibraries based upon the structure of the identified compounds. We seek to identify compounds that are active in the nanomolar range.

References for Example 1

Adey, N. B., and Kay, B. K. (1996) Gene 169, 133–134.
Adey, N. B., Mataragnon, A. H., Rider, J. E., Carter, J. M., and Kay, B. K. (1995) Gene 156, 27–31.
Albrecht, J.-C., Nicholas, J., Biller, D., Cameron, K. R., Beisinger, B., Newman, C. and Wittman (1992) J. Virol. 66, 5047–5058.
Anders, D. G. and Gibson, W. (1988) J. Virol. 62, 1364–1372.
Anders, D. G., Irmiere, A. and Gibson, W. (1986) J. Virol. 58, 253–262.
Anders, D. G., Kacica, M. A., Pari, G. S. and Punturieri, S. M. (1992) J. Virol. 66, 3373–3384.
Baer, R., Bankier, A. T., Biggin, M. D., Deininger, P. L., Farrell, P. J., Gibson, T. J. and Hatfull, G. (1984) Nature 310, 207–211.
Balfour, H. H. (1992) Res. Virol. 143, 219–221.
Barry, P. A., Pratt-Lowe, E., Peterlin, B. M., and Iuciw, P. A. (1990) J. Virol. 64, 2932–2940.
Biegalke, B. J. and Geballe, A. P. (1991) Virology 183, 381–385.
Blond-Elguindi, S., Cwirla, S., Dower, W., Lipshutz, R., Sprang, S., Sambrook, J., and Gething, M.-J. (1993) Cell 75, 717–728.
Bottger, V., Bottger, A., Lane, E. B., and Spruce, B. A. (1995) J. Mol. Biol. 247, 932–946.
Bottger, V., and Lane, E. B. (1994) J. Mol. Biol. 235, 61–67.
Britt, W. J. and Alford, C. A. (1996) In Fields, B., et al (eds.) Virology, Third Edition, Raven Press, NY, pp. 2493–2524.
Bunin, B. A., and Ellman, J. A. (1992) J. Am. Chem. 114, 10997–10998.
Bunin, B. A., Plunkett, M. J., and Ellman, J. A. (1994) Proc. Natl. Acad. Sci. USA 91, 4708–4712.
Challberg, M. D. (1986) Proc. Natl. Acad. Sci. USA 83, 9094–9098.
Chatterjee, S. N., Fiala, M., Weiner, J., Steward, J. A., Stacey, B. and Warner, N. JAMA 240, 2446–2449.
Chee, M. S., Bankier, A. T., Beck, S., Bohni, R., Brown, et al (1990) Curr. Top. Micro. Immunol. 154, 125–169.
Cherrington, J. M. and Mocarski, E. S. (1989) J. Virol. 63, 1435–1440.
Chrisp, P. and Clissold, S. P. (1991) Drugs 41, 104–129.
Colberg-Poli, A. M., Santomenna, L. D., Harlow, P. P., Benfield, P. A. and Tenny, D. J. (1992) J. Virol. 66, 95–105.
Crute, J. J. and Lehman, I. R. (1989) J. Biol. Chem. 264, 19266–19270.
Davison, A. J. and Scott, J. E. (1986) J. Gen. Virol. 67, 1759–1816.
Depto, A. and Stenberg, R. M. (1989) J. Virol. 63, 1232–1238.
Digard, P., Chow, C. S., Pirrit, L., and Coen, D. M. (1993) J. Virol. 67, 1159–1168.
Digard, P., Bebrin, W., Weisshart, K. and Coen, D. M. (1993) J. Virol. 67, 398–406.
Digard, P., Williams, K. P., Hensley, P., Brooks, I. S., Dahl, C. E. and Coen, D. M. (1995) Proc. Natl. Acad. Sci. USA 92, 1456–1460.
Doolittle, R. F. (1995) Annu Rev Biochem 64: 287–314.
Doyle, P. M. (1995) J Chem Technol Biotechnol 64: 317–324.
Drew, W. L. Miner, R. C. Busch, D. F., et al. (1991) J. Inf. Dis. 163, 716–719.
Dummer, J. S. (1990) Rev. Infect. Dis. 12(S), 767–775.
Elias, P., O'Donnell, M. E., Mocarski, E. S. and Lehman, I. R. (1986) Proc. Natl. Acad. Sci. USA 83, 6322–6326.
Enright, H., Haake, R., Weisdorf, D., et al. (1993) Transplantation 55, 1339–1346.
Ertl, P. F. and Powell, K. L. (1992) J. Virol. 66, 4126–4133.
Ertl, P. F., Thomas, M. F. and Powell, K. L. (1991) J. Gen. Virol. 72, 1729–1734.
Fixman, E. D., Hayward, G. S. and Hatward, S. D. (1992) J. Virol. 66, 5030–5039.
Fowler, K. B., Stagno, S., Pass, R. F., Britt, W. J., Boll, T. J. and Alford, C. A. (1992) N. Engl. J. Med. 326, 663–667.
Frank, K. B., Chiou, J.-F. and Cheng, Y.-C. (1984) J. Biol. Chem. 259, 1566–1569.
Gallo, M. L., Jackwood, D. H., Murphy, M., Marsden, H. S. and Parris, D. S. (1988) J. Virol. 62, 2874–2883.
Goodrich, J. M., Mori, M., Gleaves, C. A., et al. (1991) N. Engl. J. Med. 325, 1601–1607.
Gottlieb, J., Marcy, A. I., Coen, D. M. and Challberg, M. D. (1990) J. Virol. 64, 5976–5987.
Gordon, E. M., Barrett, R. W., Dower, W. J., Fodor, S. P. A., and Gallop, M. A. (1994a) J Med Chem 37, 1233–1251.
Gordon, E. M., Barrett, R. W., Dower, W. J., Fodor, S. P. A., and Gallop, M. A. (1994b) J Med Chem 37, 1385–1401.
Hammer, J., Valsasnini, P., Tolba, K., Bolin, D., Higelin, J., Takacs, B.&. Sinigaglia, F.(1993) Cell 74: 197–203
Hammer, J., Takacs, B. Sinigaglia, F.(1992) J Exp Med 176: 1007–13.

Hamzeh, F. M., Lietman, P. S., Gibson, W. and Hayward, G. S. (1990) *J. Virol.* 64, 6184–6195.

He, Y. S., Xu, L. and Huang, E.-S. (1992) *J. Virol.* 66, 1098–1108.

Hernandez, T. R. and Lehman, I. R. (1990) *J. Biol. Chem.* 265, 11227–11232.

Hicks, T., Fowler, K., Richardson, M., Dahle, A., Adams, L. and Pass, R. (1993) *J. Pediatr.* 123, 779–782.

Hofflin, J. M., Potassman, I., Baldwin, J. C., et al. (1987) *Ann. Intern, Med. s*, 209–216.

Horwitz, C. A., Henle, W. and Henle, G. (1979) *Postgrad. Med.* 66, 153–158.

Huang, E.-S. (1975) *J. Virol.* 16, 298–310.

Huang, E.-S. and Kowalik, T. F. (1993) In Becker, Y., Darai, G. and Huang, E,-S. (eds.) *Molecular Aspects of Human Cytomegalovirus Diseases*, Springer-Verlag, NY, pp. 3–45.

Iskendrian, A. C., Huang, L., Reilly, A., Stenberg, R. M. and Anders, D. G. (1996) *J. Virol.* 70, 383–392.

Johnson, P. A., Best, M. G., Friedmann, T. and Parris, D. S. (1991) *J. Virol.* 65, 700–710.

Kay, B. K., Adey, N. B., He, Y.-S., Manfredi, J. P., Mataragnon, A. H., and Fowlkes, D. M. (1993) *Gene* 128, 59–65.

Kashanchi, F., Duvall, J. F. and Brady, J. N. (1992) *Nucl. Acids Res.* 20, 4673–4674.

Kemble, G. W., McCormick, A. L., Pereira, L. and Mocarski, E. S. (1987) *J. Virol.* 61, 3143–3151.

Klemola, E., von Essen, R., Henle, G. and Henle, W. (1970) *J. Infect. Dis.* 121, 608–614.

Koff, A. and Tegtmeyer, P. (1988) *J. Virol.* 62, 4096–4103.

Koivunen, E., Wang B. & Ruoslahti E. (1994) J Cell Biol 124: 373–80.

Koval, V., Clark, C., Vaishnav, M., Spector, S. A. and Spector, D. H. (1991) *J. Virol.* 65, 6969–6978.

LaFemina, R. L. and Hayward, G. S. (1983) *J. Gen. Virol.* 64, 373–389.

Martignetti, J. A. and Barrell, B. G. (1991) *J. Gen. Virol.* 72, 1113–1121.

Masse, M. J. O., Karlin, S., Schachtel, G. A. and Mocarski, E. S. (1992) *Proc. Natl. Acad. Sci. USA* 89, 5246–5250.

McGeoch, D. J., Dalrymple, M. A., Davison, A. J., Dolan, et al (1988) *J. Gen. Virol.* 69, 1531–1574.

Mocarski, E. S. (1996) In Fields, B., Howley, P. and Knipe, D. (eds.) *Virology*, Third Edition, Raven Press, NY, pp. 2447–2492.

Monahan, S. J., Barlam, T. F., Crumpacker, C. S. and Parris D. (1993) *J. Virol.* 67, 5922–5931.

Oldenburg, K., Loganathan, D., Goldste in, I., Schultz, P., and Gallop, M. (1992) *Proc. Natl. Acad. Sci. USA* 89, 5393–5397.

Owsianka, A. M., Hart, G., Murphy, M., Gottlieb, J., Boehme, R., Challberg, M. and Marsden, H. S. (1993) *J. Virol.* 67, 258–264.

Pari, G. S. and Anders, D. G. (1993) *J. Virol.* 67, 6979–6988.

Pari, G. S., Kacica, M. A. and Anders, D. G. (1993) *J. Virol.* 67, 2575–2582.

Peterson, P. K., Gekker, G., Chao, C. C., et al. (1992) *J. Clin. Invest.* 89, 574–580.

Pizzorno, M. C., O'Hare, P., Sha, L., LaFemina, R. L. and Hayward, G. S. (1988) *J. Virol.* 62, 1167–1179.

Plotkin, S. A., Starr, S. E., Friedman, H. M., et al. (1989) *J. Inf. Dis.* 159, 860–865.

Plotkin, S. A., Starr, S. E., Friedman, H. M., Gonczol, E. and Brayman, K. (1990) *Rev. Inf. Dis.* 12(S), 827–838.

Pollard, A. B. (1988) *Pediatr. Infect. Dis. J.* 7, 97–102.

Powell, K. L. and Purifoy, J. M. (1977) *J. Virol.* 24, 618–626.

Preston, V. G., Coates, J. A. V. and Rixon, F. J. (1983) *J. Virol.* 45, 1056–1064.

Rand, K. H., Pollard, R. B. and Merrigan, T. C. (1978) *N. Engl. J. Med.* 298, 951–953.

Rando, R. F., Srinivasan, A., Feingold, J, Gonczol, E., Plotkin, S. (1990) *Virology* 176, 87–97.

Reddig, P. J., Grinstead, L. A., Monahan, S. J., Johnson, P. A. and Parris, D. S. (1994) *Virology* 200, 447–456.

Reid, R., Mar, E.-C., Huang, E.-S. and Topal, M. D. (1988) *J. Biol. Chem.* 263, 3898–3904.

Reusser, P., Gambertoglio, J. G., Lilleby, K. and Meyers, J. D. (1992) *J. Inf. Dis.* 166, 473–479.

Reyman, T. A. (1966) *Am. Heart J.* 72, 116–123.

Rickles, R. J., Botfield, M. C., Weng, Z., Taylor, J. A., Green, O. M., Brugge, J. S., et al (1994) *EMBO J.* 13, 5598–5604.

Ripalti, A., Dal Monte; P., Boccuni; M.C., Campanini; F., Lazzarotto; T., Campisi; B., et al (1994) J Virol Methods 46:139–50.

Ripalti, A., Boccuni, M. C., Campanini, F. and Landini, M. P. (1995) *J. Virol.* 69, 2047–2057.

Roizman, B. and Sears, A. E. (1996) In Fields, B et al (eds.) *Virology*, Third Edition, Raven Press, NY, pp. 1043–1107.

Schmidt, G. M., Horak, D. A., Niland, J. C., Duncan, S. R., Forman, S. J. and Zaia, J. A. (1991) *N. Engl. J. Med.* 324, 1005–1011.

Schrier, R. D., Rice, G. P. A. and Oldstone, M. B. A. (1986) *J. Infect. Dis.* 153, 1084–1091.

Singh, N., Dummer, J. S., Ho, M., et al. (1988) *J. Infect. Dis.* 158, 124–131.

Skaliter, R. and Lehman, I. R. (1994) *Proc. Natl. Acad. Sci. USA* 91, 10665–10669.

Skouteris, G. G. and. Georgakopoulos, E. (1996) *Biochem. Biophys. Res. Commun.* 218: 229–233.

Smyth, R. L., Scott, J. P., Borysiewicz, L. K., et al. (1991) *J. Inf. Dis.* 164, 1045–1050.

Snoeck, R., Neyts, J. and De Clerq, E. (1993) In Michaelson, S. and Plotkin, S. A. (eds.) *Multidisciplinary approach to understanding cytomegalovirus disease*. Excerpta Medica, Amsterdam, pp. 269–278.

Spaete, R. R. (1991) *Transplant Proc.* 23, 90–96.

Sparks, A., Rider, J., Hoffman, N., Fowlkes, D., Quilliam, L., and Kay, B. (1996a) *Proc. Natl. Acad. Sci. USA* 93, 1540–1544.

Sparks, A. B., Quilliam, L. A., Thorn, J. M., Der, C. J., and Kay, B. K. (1994) *J. Biol. Chem.* 269, 23853–23856.

Stanimirovic, D. B., Ball, R and Durkin, J. P. (1995) *Neurosci Lett* 197: 219–222.

Stasiak, P. C. and Mocarski, E. S. (1992) *J. Virol.* 66, 1050–1058.

Stenberg, R. M., Fortney, J., Barlow, S. W., Magrane, B. P., Nelson, J. A. and Ghazal, P. (1990) *J. Virol.* 64, 1556–1565.

Stern, H. (1984) In Plotkin, S. A., et al (eds.) *CMV: pathogenesis and prevention of human infection*. Alan Liss, NY, pp. 263–269.

Straub, S. G. and Sharp, G. W. (1996) *J. Biol. Chem.* 271: 1660–1668.

Stow, N. (1993) *Nucl. Acids Res.* 21, 87–92.

Sullivan, V., Biron, K. K., Talarico, C., Stanat, S. C., Davis, M., et al (1993) *Antimicrob. Agents Chemother.* 37, 19–25.

Tenny, D. J., Micheletti, P. A., Stevens, J. T., Hamatake, R. K., Mathews, J. T., Sanchez, A. R. et al (1993) *J. Virol.* 67, 543–547.

Webster, A. (1991) *J. AIDS Hum. Retro.* 4, S47–S52.

Webster, A., Lee, C. A., Cook, D. G., et al. (1989) *Lancet* 2, 63–66.

Webster, A., Phillips, A. N., Lee, C. A., Janossy, G., Kernoff, P. B. and Griffiths, P. D. (1992) Clin. Exp. Immunol. 88, 6–9.
Weiland, K. L., Oien, N. L., Homa, F., and Wathen, M. W. (1994) Virus Res. 34, 191–206.
Welch, A. R., McNally, L. M. and Gibson, W. (1991a) J. Virol. 65, 4091–4100.
Welch, A. R., Woods, A. S., McNally, L. M., Cotter, R. J. and Gibson, W. (1991b) Proc. Natl. Acad. Sci. USA 88, 10792–10796.
Wingard, J. R., Piantadosi, S., Burns, W. H., Zahurak, M. L., Santos, G. W. and Saral, R. (1990) Rev. Infect. Dis. 12(S), 793–804.
Winston, D. J., Ho, W. G., Bartoni, K., et al. (1993) Ann. Intern. Med. 118, 179–184.
Wright, D. A., Staprans, S. I. and Spector, D. H. (1988) J. Virol. 62, 331–340.
Wu, L, C. and Shahied, S. I. (1995) Arch Biochem Biophys 324 123–129.
Yau, J. C., Dimopoulos, M. A., Huan, S. D., et al. (1991) Eur. J. Haematol. 47, 371–376.
Ye, L. B. and Huang, E.-S. (1993) J. Virol. 67, 6339–6347.
Baldanti, F., Silini, E., Sarasini, A., Talarico, C. L., Stanat, S. C., Biron, K. K., Furione, M., Bono, F., Palu, G., and Gerna, G. (1995). J. Virol. 69:796–800.
Hanson, M. N., Preheim, L. C., Chou, S., Talarico, C. L., Biron, K. K., and Erice, A. (1995). Antimicrob. Agents Chemother. 39:1204–1205.
Sarasini, A., Baldanti, F., Furione, M., Percivalle, E., Brerra, R., Barbi, M., and Gerna, G. (1995). J. Med. Virol. 47:237–244.

Example 2

Isolation of Phage Expressing Peptides Which Bind to Protein Kinase CβII

Protein Kinases are important regulators of intracellular processes and play a central role in signal transduction. One of the most important controlling points is the regulation of protein kinase C. Its various isozymes are involved in many processes which regulate cell growth and hence it is an attractive target for an antitumor agent. To explore this possibility we have-isolated surrogate ligands specific for human protein kinase C beta II.

Baculovirus produced Protein Kinase C $\beta_{II}$ was obtained from L. Ballus (Sphinx Pharmaceutical Corp.) and was immobilized as described in Example 1 and affinity selection of phage was carried out as in example 1 with several slight modifications. Elution was found to be more efficient if the initial pH 2.0 glycine treatment was carried out with buffer prewarmed to 50° C. and was immediately followed by an elution at pH 12 with prewarmed 100 mM ethanolamine for 10 minutes. The eluted phage was pooled, neutralized, and amplified in 1 ml of 2×YT containing E. coli DHFaF' in a 2 ml Megatiter plate in which each 2 ml well is arranged in a 96 well array.

Results:

We tested 95 individual phage (8 from each library except 7 from the CWL) and found potential binding phage in the D, F and $X_{10}C$ libraries. Additional phage from these libraries were tested and we found 23 potential binders. We further confirmed the specificity of binding by testing the phage against 7 other proteins. A strong signal and good specificity was found on 13 clones and DNA was isolated from these and was sequenced using an automated sequencing protocols. The DNA sequences were compared and translated and an alignment and consensus of the peptides encoded by the phage are shown below.

| Frequency | Sequence | | | | | | | | | | |
|---|---|---|---|---|---|---|---|---|---|---|---|
| 8 | G | K | G | W | K | C | F | G | A | L | C | (SEQ ID NO:32) |
| 2 | S | T | T | F | Q | C | V | G | L | L | C | (SEQ ID NO:33) |
| 1 | A | N | G | W | E | C | I | G | Q | F | C | (SEQ ID NO:34) |
| 1 | K | P | V | W | K | C | T | G | L | F | C | (SEQ ID NO:35) |
| 1 | S | A | Q | W | Q | C | V | G | E | F | C | (SEQ ID NO:36) |
| 1 | Consensus | | | W | Phi | C | Pho | G | x | F/L | C | |
| 2 | L | P | M | A | R | W | T | C | V | N | C | (SEQ ID NO:37) |
| 1 | A | V | D | R | G | W | T | C | V | N | C | (SEQ ID NO:38) |
| 1 | Q | I | T | P | Q | W | T | C | V | N | C | (SEQ ID NO:39) |
| 1 | Consensus | | | | | W | T | C | V/I | N | C | |
| 1 | G | V | C | Q | S | S | D | H | R | E | C | (SEQ ID NO:40) |
| 1 | G | W | Q | E | R | F | Q | Q | E | D | R | (SEQ ID NO:41) |
| 1 | E | V | P | T | T | K | V | L | W | P | S | (SEQ ID NO:42) |

Phi = hydrophilic
Pho = hydrophobic

The peptides fall into 3 classes. The first and largest class are peptides from the $X_{10}C$ library and are characterized by a loop of 4 amino acids constrained by two cysteine residues. There are conserved residues both inside the loop and flanking the N terminal cysteine. The second group of peptides also came from the $X_{10}C$ library and is characterized by 2 residue loop the conserved sequence is a hexapeptide in which the only variance between residues is a valine vs. isoleucine substitution on one of the peptides. The third group consists of three peptides with little primary sequence conservation.

To place the different clones in a relative order based on the affinity they have for the target, we carried out a set of phage ELISA with decreasing concentrations of phage. The results are shown in FIG. 12. The phage exhibit a fairly wide range of binding affinities, needing anywhere from 0.5 µl to 10 µl of phage supernatant to exhibit half maximal binding.

This example uses a eukaryotic cellular protein kinase as a target for which we have isolated artificial ligands. The peptide sequences shown above could easily be used to set up a screen for small molecules which bind at the same site. The artificial ligand could be used in any of the ways discussed in example 1. We could also use any other cellular enzyme as a target. These selections may also be done in the presence of one or more cofactors or regulators of the enzymes function. In the case of PKC, we could, have carried out the selection in the presence of diacyglycerol or phorbol esters to activate the enzyme. This would result in the enzyme taking on a different conformation and may alter the ligands that are obtained. This strategy may be altered to target a specific site by eluting the phage with the known ligand. To do this, we would carry out all of the binding and amplification steps as above, however, the elution step would be replaced by an extended incubation in the presence of large amounts of the natural ligand (i.e. Phorbol). Alternatively, the pool of phage from the final round of selection could be "sorted" by adding the natural ligand first followed by the phage. The binding of the natural ligand would prevent the phage binding to a specific site but not at others. We would then take the supernatant which contains the unbound phage and test individuals for binding. In this way you can enrich for phage to a specific known site. Sequence analysis of these phage would then yield a cluster of peptides which would describe the ligand binding site.

This approach could also be used if a compound was available which one wished to find alternatives to. In this case, the phage could be eluted with the compound at each round of selection or the target could be blocked by the compound before phage from the final round of selection were allowed to bind. Both of these approaches would give rise to artificial ligands which bound to the site blocked by the compound. These ligands could then be used in a high throughput screen to find additional compounds which bind to the same or overlapping sites.

Example 3

Isolation of Peptides Which Bind to Human MDM2

Subcloning of Human MDM2 cDNA Into GST Expression Vector.

The MDM2 (mouse double minute protein) is involved in the control of cell growth by interacting with the protein product of the tumor suppressor gene p53. In normal cells p53 acts as a sensor of DNA damage and uncontrolled cellular proliferaction and prevents cell growth by activating a number of gene products which cause either cell cycle arrest or programmed cell death (apoptosis). MDM2 interacts with the N terminus of p53 and prevents it from activating these genes. Thus overexpriession of MDM2 leads to uncontrolled cell growth. One potential place for pharmacological intervention in this system is the disruption of the MDM2—p53 interaction. We set out to isolate surrogate ligands of the p53—MDM2 interaction using phage display with the goal of using these surrogate ligands to format a screen designed to find small molecule inhibitors of this interaction.

In order to produce a fusion protein for affinity selection we subcloned the MDM2cDNA from-pQE11-hMDS by digestion with BamHI and EcoRV and ligating the cDNA into pGEX5X-1 (Pharmacia) cut with BamHI and SmaI to produce pGSThMDM2. The deletion construct expressing GST fused to the first 139 amino acids of MDM2 was made by digesting pGSThMDM2 with BsrGI and XhoI, blunting the ends with Klenow and religating. All clones were verified by restriction enzyme mapping and DNA sequence analysis. The fusion proteins were produced according to standard protocols from the manufacturer and were used as is or cleaved with thrombin.

Affinity Selection for Phage displaying MDM2 binding peptides. Selection for phage used the same techniques used in examples 1 and 2 except that enrichment was monitored by performing phage ELISAs on the pools of phage isolated after rounds 2 and 3 using dilutions of phage equivalent to 1 to 100 µl of the phage supernatant in a 200 µl binding reaction.

Enrichment for binders monitored by pool ELISA. After 3 rounds of selection, the only libraries which showed an enrichment for binding phage were the H and W libraries. 95 clones were tested, 48 from the H library and 47 from the W library. Strong binding was observed on 5 from the H library and 28 from the W library. Testing the specificity of these 33 phage against a variety of proteins showed that 17 of them bound to give strong signals and were very specific. The DNA sequences for the displayed phage were determined and are shown below:

```
                                  PFQDYWEELLN   (SEQ ID NO: 43)
                                  PFHSWWQDLTD   (SEQ ID NO: 44)
                                  NFWDEWQTFMD   (SEQ ID NO: 45)
                   11 clones      SFTDYWRDLEQ   (SEQ ID NO: 46)

Consensus      xFxDyWqdLxx   (SEQ ID NO: 47)

MEEPQSDPSVEPPLSQETFSDLWKLLPENNVL   human p53 (SEQ ID NO: 48)
              MTAMEESQSDISLELPLSQETFSGLWKLLPPEDIL mouse p53 (SEQ ID NO: 49)
        surface contacts:          *   **  **

Other peptides which do not fit the consensus:
                        GAPWNWEKKEL    (SEQ ID NO: 50)
                        ADPRLPVEREL    (SEQ ID NO: 51)
                        MDGSGGERNSMW   (SEQ ID NO: 52)
                        PMRTEWAVGSES   (SEQ ID NO: 53)
```

These peptides sequences can be placed in two groups. The first group align between themselves to form the consensus sequence FxDyWqdL where the upper case residues are completely conserved. This sequence aligns perfectly with a sequence with the human or mouse p53 protein that has been shown to interact with the N terminal portion of hMDM2 by biochemical studies and crystallography (Leng et al 1995 and Kussie et al 1996). The other peptides have limited homology to each other and do not align with peptide sequences from p53 or any other protein in genbank.

Conclusions:

These experiments show the use of biased combinatorial peptide libraries to identify ligands which mimic a biological interaction, in this case a protein-protein interaction between MDM2 and p53. The peptides obtained in these experiments clearly mirror the native sequence of p53 and are identical to both the mouse and human p53 at the residues which are in contact with MDM2.

Leng, P., D. R. Brown, C. V. Shivakumar, S. Deb and S. P. Deb. (1995). N-Terminal 130 amino acids of MDM2 are sufficient to inhibit p53-mediated transcriptional activation. Oncogene 10:1275–1282.

isolated in the first screen. All of the 11 clones from the P library were identical and encoded a peptide shown below. A third selection was also carried out identical to the first and phage from the X10C and P libraries were tested, this time giving rise to several new sequences as well as several found in earlier selections:

| frequence | Screen | Library | Sequence (SR linker-random peptide-SR linker) |
|---|---|---|---|
| 22 + 9 + 2 | 1,2,3, | $X_{10}C$ | S R V C A I W P D L D G C S R (SEQ ID NO:54) |
| 6 | 1 | $X_{10}C$ | S R W C S L R P Q D E G C S R (SEQ ID NO:55) |
| 2 | 1 | $X_{10}C$ | S R W C E L W S Q D I G C S R (SEQ ID NO:56) |
| 11 + 6 | 2,3 | P | S R W C E L W P E G S G C S R (SEQ ID NO:57) |
| 1 | 3 | $X_{10}C$ | S R L C E V W P Q T A G C S R (SEQ ID NO:58) |
| 1 | 3 | P | S R W C D I W P D T G S C S R (SEQ ID NO:59) |
| 1 | 3 | P | S R L C D I M P Q T V G C S R (SEQ ID NO:60) |
| 1 | 3 | P | S R W C E V W P D K R W C S R (SEQ ID NO:61) |
| CONSENSUS | | | S R W $C_{acidPho}$ P $_{Phi\ x\ x}$ G C S R (SEQ ID NO:62) |

| $X_{10}$ C | TCG AGG GTG TGT GCT ATT TGG CCG GAT CTG GAT GGT TGC TCT AGA (SEQ ID NO:63) |
| | S R V C A I W P D L D G C S R (SEQ ID NO:64) |
| P | TCG AGG TGG TGT GAG TTG TGG CCG GAG GGT TCT GGT TGT TCT AGA (SEQ ID NO:65) |
| | S R W C G L W P G G S G C S R (SEQ ID NO:66) |

Kussie, P. H., S. Gorina, V. Marechal, B. Elenbaas, J. Moreau, A. J. Levine, Pavletich, N. P. (1996). Structure of the mdm2 oncoprotein bound to the p53 tumor suppressor transactivation domain. Science 274:948–953.

Example 4

Isolation of Peptides Which Bind to *E. coli* Proline tRNA Synthetase (ProRS)

Transfer RNA synthetases catalyze the ATP dependent charging of a tRNA molecule with a specific amino acid. These charged tRNAs are then utilized in translation for the production of new proteins. These enzymes are required for growth in all organisms and are quite different from bacteria, to humans. They thus represent an attractive target for antimicrobial compounds. We set out to isolate surrogate ligands to the *E. coli* proline synthetase and test to see if these surrogate ligands were targeted to the active site of the enzyme.

Affinity Selection for phage displaying *E. coli* ProRS binding peptides. Selection for phage used the same techniques used in example 3.

Enrichment for binders monitored by pool ELISA. After 3 rounds of selection, the only library which showed significant enrichment for binding phage was the $X_{10}C$ library. We screened 95 individual clones for binding to the target and carried 34 individual clones through for screening against a variety of proteins. Sequence was obtained from 30 of these and is shown below.

We carried out a second affinity selection to determine our efficiency at isolating phage which bound to the target, the only difference from the first selection in that the time allowed for binding was overnight at 4° C. The phage were then amplified during the day and the next round of binding was carried out at night. We observed enrichment in the $X_{10}C$ library again and also a slight enrichment in the P library. We tested individual isolates from the P and $X_{10}C$ and analyzed 20 by sequence analysis. All 9 sequences from the $X_{10}C$ library were the same as the most abundant clone Each of the isolated phage display peptides constrained by two cysteines with an intervening loop of 8 residues with several conserved residues both inside and outside the loop. The one clone isolated from the P library also contained a peptide with identical constraints. The codon structure of the DNA encoding the displayed peptide shows that this phage is not a contaminant from the $X_{10}C$ library. The fixed C residue in the $X_{10}C$ library uses the codon TGC, however, in the phage isolated from the P library this C residue is encoded by a TGT codon, clearly demonstrating that this clone did indeed arise from the P library.

A peptide corresponding to the most often isolated phage was synthesized and used in an ELSA as described in example 1. FIG. 13 shows that the peptide is specific for *E. coli* ProRS and that the TP does not bind other peptides. This interaction can be disrupted in a dose dependent fashion by a non-biotinylated peptide of the same sequence (FIG. 14). In addition, the binding of this peptide to ProRS is dependent on time and peptide concentration (FIG. 15).

One question that could be answered with peptides designed from these phage is whether or not they are directed to random regions on the target protein or if they target active sites and regions of other biological interactions. The peptides used in the above ELSAs were added to a charging assay to assess its affects on enzymatic activity of the target. Although the time of preincubation with the peptide needed was long (about 1.5 hours for 50% inhibition using 530 $\mu$M peptide), the peptide effectively inhibited the activity of the enzyme with an Ki of greater than 500 $\mu$M. This inhibition is competitive in respect to proline, thus these peptides are directed to the active site of the enzyme. We did not isolate any phage expressing peptides which bound to other regions of the target.

This example illustrates several important points. First, we are able to isolate phage displaying peptides which will bind to a bacterial protein, in this case one from *E. coli*. In addition, the use of biased libraries clearly confers an advantage vs. using completely random libraries. All of the phage that bound specifically to this protein displayed constrained peptides and these peptides were enriched in the $X_{10}C$ library. The only library other than $X_{10}C$ from which we isolated binding phage was the P library, and the central P residue is conserved in 3 of the 4 peptides we identified. Due to the structure of the rest of the libraries which we screened, none of them would be expected to be enriched for these peptides binding to ProRS. For example, although the W residue before the first C is conserved, our W library is not expected to be enriched for the correct peptides because of the position of the W: it is in surrounded on both sides by 5 random residues. There are not enough residues to encode the two C residues with an intervening 8 residue loop. Thus the only libraries that we expect to have a higher than random number of binders would be the $X_{10}C$ and P libraries, both of which gave us binding phage. The other libraries lend support to this idea by not giving rise to any binding phage.

The second point this example illustrates is the efficiency our selection process has in isolating phage that bind to a target with a high enough affinity to be captured. We carried out the selection twice and each time isolated the same phage. Thus after screening a target with this procedure we have high confidence that if binding phage are present we will isolate them.

Cluster analysis of the selected peptides suggests that there is selective binding of peptides to the target protein. If peptides were capable of binding to any surface of the protein, each of the peptides would be different and there would not be any clustering of peptide sequences. Clearly all of the peptides isolated here are binding to the same site. In addition, they are binding to the active site of the enzyme, which is likely the only available biologically active site on the protein. Therefore the peptides isolated by this process are targeting biologically relavent sites on the target protein.

A fourth and intriguing point is illustrated by virtue of isolating only disulfide containing peptides. This particular protein was from E. coli. Inside of prokaryotic cells, the environment is such that disulfide bonds are reduced. For the peptide libraries this means that the displayed peptides are likely to be linear inside of the cell and then circularize after being exposed on the outside of the cell. This means that the peptide would not take on the same conformation inside the cell as it is displayed on mature phage that are used in panning. If a peptide expressed inside of E. coli bound to an E. coli protein and inhibited its function and this protein were essential, then that peptide would be selected against using the process of making and propagating the phage display library (because these phage are grown on an E. coli host). In contrast to all of the linear libraries used in this example, the $X_{10}C$ library must display a cyclized peptide which exhibits a different conformation inside of the cell and therefore would not bind to the protein in question, in this case the E. coli proline tRNA synthetase.

Thus, if one were trying to isolate peptides which bind to E. coli proteins, the peptides themselves will most likely have to be constrained or they will be selected against during library construction and amplification. Furthermore, using libraries with two, four or six fixed cysteines as suggested by Ladner (U.S. Pat. No. 5,223,409) would only be successful if the spacing between the cysteine residues were fortuitously chosen. In this case the spacing required was 8 residues, but this was not known before hand. To make and screen many different libraries with all the combinations would be cumbersome. In these cases it would be advantageous to fix one cysteine and enrich for a second at each position as described in the beginning of this document. In this way the number of peptides expressing a cysteine at each position would be increased, but each clone would have only a pair of cysteines and all other residues would be random.

Example 5

H. Influenzae Tyrosine tRNA Synthetase

As discussed above for the proline tRNA synthetase, the tyrosyl tRNA synthetase is an attractive target for new antibiotics. We set out to isolate surrogate ligands for this synthetase and to determine where these peptides were targeted on the enzyme.

Affinity Selection for phage displaying E. coli TyrRS binding peptides. Selection for phage used the same techniques used in example 3.

Results:

After 3 rounds of selection, phage ELISAs showed enrichment for binding phage in the D, F, W, N, P, CWL, PHD7 (random 7-mer, New England Biolabs) and PHD12 (random 12-mer New England Biolabs) libraries. Individual clones from each of these libraries was tested for specific binding and the peptide displayed were deduced from the DNA sequence. The results are shown below:

| # of Clones | Library | Sequence | |
|---|---|---|---|
| 1 | CWL | L Y S W P D E Q Y E R P (TyrRS1) | (SEQ ID NO:67) |
| 1 | W | F G F Y G W P D D Q Y | (SEQ ID NO:68) |
| 1 | PHD12 | M Y T W P G S P Y L Q M | (SEQ ID NO:69) |
| 2 | PHD12 | M Y S W P G E H Y T V H | (SEQ ID NO:70) |
| 2 | CWL | M Y A W P D S S E L E K | (SEQ ID NO:71) |
| 1 | PHD7 | M Y S W P G V | (SEQ ID NO:72) |
| 2 | PHD7 | Y Y G W P S E | (SEQ ID NO:73) |
| 1 | W | D R V Y G W P P F E E | (SEQ ID NO:74) |
| 1 | W | A Y H W P W V E S E W | (SEQ ID NO:75) |
| 1 | W | G Y S W P W P D D N A S R | (SEQ ID NO:76) |
| 1 | W | I Y S W P W P S N E N | (SEQ ID NO:77) |
| 1 | PHD7 | Q Y T W P W P | (SEQ ID NO:78) |
| 1 | P | Y S W P W P D F N E T | (SEQ ID NO:79) |
| 1 | W | A Y S W P W H D T V D (TyrRS2) | (SEQ ID NO:80) |
| 5 | W | W D G F A W P M H Q T | (SEQ ID NO:81) |
| 3 | F | W P W G G F E W P K L | (SEQ ID NO:82) |
| 1 | D | R Y W W P D W G S R E | (SEQ ID NO:83) |
| 1 | W | L W W P E W G V Y T G | (SEQ ID NO:84) |
| 3 | D | Y F W W P D W G S S A | (SEQ ID NO:85) |
| 1 | W | D R G W W W P S W G V S R | (SEQ ID NO:86) |
| 7 | D | G Y W W P D W G S G O | (SEQ ID NO:87) |

-continued

| # of Clones | Library | Sequence | |
|---|---|---|---|
| 1 | P | A E Y W W P D W G F F (TyrRS3) | (SEQ ID NO:88) |
| 1 | W | R L Q Y W W P D W G P (TyrRS) | (SEQ ID NO:89) |
| 4 | N | M Y W W P N W G S O E (TyrRS4) | (SEQ ID NO:90) |
| 1 | P | W L D G L P L Y H E V (TyrRS5) | (SEQ ID NO:91) |
| 1 | CWL | D T V R K D L L L E R E (TyrRS6) | (SEQ ID NO:92) |

The peptide sequences are clustered in 4 distinct groups, the first two groups having multiple related members and the last two containing one sequence each. There are several similar, positions in groups one and two: they all contain a central YXWP (SEQ ID NO:93) motif. It is tantalizing to speculate that the Y is mimicking free tyrosine and that the WP is mimicking ATP (with the P serving as the 5 membered sugar and the W as the base. A subset of group 1 has a W in the position immediately downstream of the conserved WP, however this is not universal. Group 2 on the other hand contains an extended conserved motif of YWWPDWG (SEQ ID NO:94) with a propensity for S in the next position.

Peptides corresponding to TyrRS1 through TryRS6 (shown above) were synthesized and tested in several assays. Peptide TyrRS1 was biotinylated and was used for a standard ELISA as described above. This peptide binds to TyrRS specifically (FIG. 16), other peptides do not bind to the target TyrRS (FIG. 17), and the binding is dependent on time and concentration (FIGS. 18–19).

We wished to see if the peptides from groups one and two compete for binding or if they are binding to non-overlapping sites. All of the peptides were used to compete for binding of parent phage as well as with phage displaying the other peptides (TyrRS1–6). It is clear that all of the peptides compete with their respective parental phage for binding (Table below). In addition, peptides from group 2 compete for binding for phage from groups 1 and 2, however peptides from group 1 are not effective competitors with phage from group 2. This is consistent with a model for peptide binding in which peptides from group 1 bind in a groove and peptides from group 2 bind higher in the groove and prevent peptides from group 1 from entering and binding.

| | Peptide | | | | | |
|---|---|---|---|---|---|---|
| phage | 1 | 2 | 3 | 4 | 5 | 6 |
| 1 | + | + | + | + | − | − |
| 2 | + | + | + | + | − | − |
| 3 | − | −/+ | + | + | − | − |
| 4 | + | − | + | + | − | − |
| 5 | − | + | + | − | −/+ | −/+ |
| 6 | + | + | + | + | − | −/+ |

The clustering of sequences strongly suggests that the peptides are interacting at specific sites on the target. Is this a functionally relavent site? This question was addressed in two ways. First the peptides were added to a standard charging assay to see if they inhibited enzyme activity. Peptides from group 1 and 2 effectively inhibited enzymatic activity and accomplished this in a competitive manner with ATP and amino acid. Thus the peptides from the clusters both are targeted to the enzyme active site and are themselves effective inhibitors.

Clearly these peptides are directed to a potential area of target drug interaction. If this peptide can be displaced by a small molecular weight compound, the compound is likely to be a drug lead candidate. Effective inhibitors of this target are available for our use and they mimic an intermediate in the reaction of charging Tyr tRNA. These inhibitors are tyrosyladenylate compounds. One such inhibitor was tested for its ability to disrupt the phage:target interaction with all of the phage isolated. We determined that the inhibitor is an effective competitor for phage binding on a majority of group 1 phage.

The ability of the compound to inhibit the binding of the TyrRS1B peptide to TyrRS was determined. A standard ELSA was carried out except that various concentrations of the compound were added to surrogate ligand before adding the mixture to the immobilized target in a well of a microtiter dish. The results are shown in FIG. 20. It is clear that the compound inhibits the binding of the surrogate ligand to the target in a dose dependent manner. A related compound, a prolyladennylate that inhibits another synthetase (ProRS) had no effect on the binding of the surrogate ligand.

This example clearly shows several important points. First, a majority of the peptides displayed on the surface of phage are targeted to active regions of the protein. In addition, these peptides are themselves effective inhibitors of protein function. These experiments prove the utility of using peptide based surrogate ligands to detect the binding of a small molecular weight compound to a biologically active site. This assay could be used to test a large number of compounds for potential inhibitors of enzyme function, even if we had no prior knowledge of the proteins function. All that is required is that we are able to detect competition for binding between the surrogate ligand and a small molecule.

Example 6

Targeting of Transmembrane Receptors (Prophetic)

Cellular receptors which span the membrane often need to be in a membrane to take on the correct conformation for a biologically active protein. This presents a problem for conventional techniques designed to find artificial ligands targeted to the native form of the protein. One possible solution to this problem is the use of live cells to express the receptor of choice and then use the whole cell as the way to present the target to the library of artificial ligands. One system in which to do this is the oocyte from *Xenopus laevis*. We would first clone the receptor of interest into a vector from which RNA could be produced in vitro using bacterial or phage RNA polymerases. This RNA would then be injected into oocytes and the oocytes then incubated to allow the production of protein. The oocytes (probably 1–10 per binding reaction), now with the receptor of interest on the cell surface would be mixed with the library of artificial ligands and binding allowed to occur. The oocytes would be washed to remove the non-specific binding ligands and then the ligands would be elutedusing a change in pH, salt concentration or another treatment which would break the interaction. The ligands would then be amplified and subjected to further rounds of selection.

The positive selection described above may give rise to ligands specific to the receptor of interest, however, it may be necessary to use a negative selection to remove the ligands binding to proteins on the surface of the oocyte. This would be accomplished by binding the pool of artificial ligands to an oocyte which has not been injected with any RNA and thus is presenting only native oocyte proteins on its surface. Any ligands which bind to the oocyte would be removed and the ligands remaining in the supernatant would be used for subsequent rounds of positive selection. This negative selection may be carried out before or after each round of positive selection or it may only be required once during the selection process. In any case the concept is to remove artificial ligands which are binding to oocyte proteins and leave the pool of ligands enriched for those which bind to the receptor of interest.

The enrichment for ligands binding to the receptor can be onitored utilizing a modified ELISA procedure. In this case oocytes injected and expressing the receptor would be place in the well of a microtiter dish and individual artificial ligands added. In the case of phage expressing peptides a phage clone grown from an isolated plaque would be used. The oocyte would be washed and the ligand would be detected by convential methods, usually and antibody conjugated to an enzyme such as horse radish peroxidase or alkaline phosphatase. As a negative control, non-injected oocytes would be subjected to the same clone in a parallel well and the signals compared. Clones giving a higher signal in the well containing the inject oocyte would be considered positive (they bind to the receptor in a specific manner) and those with equal signals in both wells bind to a protein normally on the oocyte surface. The clones which bind would be sequenced and compared for common elements.

Other expression systems are likely to work as well. These include bacteria, yeast, baculovirus, vaccinia virus, CHO cells (chinese hamster ovary cells), HeLa, fibroblasts, adenovirus or any other expression system in which the target protein is produced in such a way that it presents an active conformation to the potential surrogate ligands. The protein could also be made in vitro by transcription and translation using any of a variety of RNA polymerases in conjunction with lysates from reticulocytes, wheat germ or any other source of enzymatic machinery for the translation of RNA to protein. It may be advantageous to produce and isolate the protein in an environment that promotes proper protein folding. One example of this would be to include canine pancreatic microsomes in the in vitro transcription/translation reaction. If the target protein were small enough or if a synthetic scheme could be devised to produce it de novo, the target could also be a completely synthetic molecule.

Example 7

Isolation and Use of Nucleic Acids as Surrogate Ligands (Prophetic)

The use of peptide based artificial ligands is a powerful approach in the paradigm of drug screening discussed here. However, there may be some targets for which it will be difficult to isolate peptide ligands. In this case it may be preferable to use a DNA or RNA based aptamer as the ligand, especially as one can work with very large (complexities of $>10^{14}$) DNA or RNA libraries. Ligands could be isolated by several different screening methodologies (U.S. Pat. Nos. 5,270,163; 5,475,096; 5,567,588; 5,595,877; and 5,637,459). For example, the starting libraries for a DNA library would have defined sequences on each end of 10 to 30 bases flanking a random core of 10 to 100 bases. Primers complementary to the defined sequences on each end would be used to amplify the library and one would have a tag (such as biotin). After amplification the double stranded DNA would be bound to a matrix (streptavidin agarose) and denatured to release ssDNA. To isolate the ligand, the target protein would be incubated with a starting library of single stranded DNA (ssDNA) and the aptamers allowed to bind. Protein:aptamer complexes would then be collected by filtration through nitrocellulose or nylon membranes which will bind protein with a very high capacity but have a low affinity for ssDNA. The unbound aptamers would be washed away through the filter with an excess of buffer leaving only the aptamers which bound to the original target protein. These aptamers would be eluted by one of several methods (pH shock, phenol extraction, SDS treatment or heat), precipitated with ethanol and then amplified by PCR to synthesize a new pool for use in the next round of selection.

This process would be repeated from once to 20 times. The number of times this would be carried out is determined by monitoring the enrichment for binders after each round or after every other round of selection. This could be accomplished in several ways. The most often used approach is to radioactively label a small percentage of the library and monitor the fraction of the library retained on the filter after each round. An alternative method is to use a primer in the amplification reaction which would allow the aptamer to be detected. Two examples of this are rhodamine and digoxigenin. Rhodamine is detected directly by fluorescence and DIG is detected by an antibody which is either directly or indirectly coupled to an enzymatic or fluorescence readout. Using a labeled primer would allow the detection of aptamer binding to target in a standard ELISA format in which the target protein is immobilized in the well of a plate, the aptamer is added and allowed to bind and is then detected using one of the methods mentioned above.

Once a sufficient level of enrichment has been attained, the final pool would be amplified and cloned into a plasmid which allows for the rapid sequencing of the inserts. This could be done by using restriction sites in the primers which are compatible with those in the vector, however it would be preferable to take advantage of the additional "A" residue added by many thermostable polymerases to clone the products into a "T" tagged vector. This is desirable because of the possibility of the aptamer containing the restriction site used for cloning, which would result in the loss of all or a portion of the aptamerupon cloning.

Individual surrogate ligand aptamers would be prepared by amplification from plasmid DNA using tagged primers. The resulting ligands would be tested for binding to the target protein as well as against several other unrelated proteins as controls for specificity. DNA from clones that bind specifically to the target protein and give strong signals will be prepared for automated DNA sequencing. The sequences will then be aligned and searched for regions of homology. The regions of linear sequence homology are likely to be representations of secondary and tertiary structures which are required for the specific interaction of the aptamer with the target.

To utilitize these ligands in the screening of small molecule libraries for drug leads, the ligand could be labeled with rhodamine or DIG as described above. Alternatively they could be labeled as described by Pitner (U.S. Pat. No.

5,650,275 and U.S. Pat. No. 5,641,629). Screens for drug leads can be carried out with the nucleic acid surrogate ligands in the manner illustrated in the above examples.

Example 8

Peptides Which Bind to *Agrobacterium faecaelis* β-Glucosidase, Carboxypeptidase, Alcohol Dehydrogenase, and *E. coli* Pro RS The inventors believe that a majority of the peptide surrogate ligands isolated using phage display will be directed to biologically active sites. These could be the sites of protein protein interactions, protein ligand interactions, the active sites of enzymes and the regulatory sites of enzymes. To demonstrate this phenomena on a range of proteins, we have chosen a diverse set of enzymes whose biological activity can be monitored. If the surrogate ligand binds to the target enzyme at the active site, it is likely that it will act as an effective inhibitor of enzyme activity. In addition, for many of the targets below, a number of active site directed inhibitors are available. Using these we will be able to map the site of interaction between the target and the protein. The enzymes targeted are *Agrobacterium faecalis* beta-glucosidase (this example), carboxypeptidase B from pig pancreas (Boehringer Mannheim cat #103 233) (Ex. 9), Yeast alcohol dehydrogenase (Sigma cat. #A3263) (Ex. 9), and *E. coli* ProRS (Exs. 4 and 9), glycogen phosphorylase a, and yeast hexokinase.

Affinity selections were carried out as in example 3 except that the protein was presented in several ways. At first the protein was immobilized on IMMULON 4 microtitration test plates (Dynex) as in previous examples, however, repeated attempts failed to isolate phage which bound specifically to the target. It was found that the target exhibited greatly reduced activity when bound to IMMULON 4 plates, making it likely that it was denatured when bound to plastic. To circumvent this problem, two approaches were used, both of which utilized biotinylated protein. Protein (1 mg) was biotinylated with Sulfo NHS-LC-LC biotin (Pierce, cat. #21338) prepared fresh as a 10 mM stock solution in ddH$_2$O. All proteins were in phosphate buffered saline. Biotinylation reagent was added to the protein solution in a 17-fold molar excess to protein and the reaction was carried out at room temperature for 30 minutes followed by ice for 30 minutes. Biotinylated proteins were separated from the excess biotinylation reagent on a SEPHADEX G-50 chromatography matrix micro-spin column (Pharmacia Biotech, Cat#27-5335-01) according to the manufacturers directions. Protein assays were conducted using BioRad Protein Assay reagent (cat#500-0006). All proteins were stored in 1xPBS+10% glycerol at −80° C.

For the first method of affinity purification, phage libraries were mixed with 1 μg biotinylated target protein in solution and allowed to incubate at room temperature for 4 hours. Phage:protein complexes were then captured on streptavidin paramagnetic beads (Promega, cat#Z5482) by adding beads and incubating the tubes while rotating at room temperature for 30 minutes. The complexes were then drawn to the sides of the tubes using a magnet and the beads were washed with TBST containing 5 mM biotin. Beads were washed once in the first round of panning and 3 times for each additional round. Phage were eluted and amplified using the sequential procedure described in example 3. In the second method of affinity purification, phage libraries were mixed with 1 μg biotinylated target protein that was first captured on streptavidin paramagnetic beads. After the protein was bound, the beads were washed once with TBST containing 5 mM biotin to block the remaining binding sites on streptavidin. The libraries and beads were then mixed at room temperature on a rotator for 4 hours and washed, eluted and amplified as above. Phage ELISAs were carried out by first coating a microtiter plate (Immulon4, Dynex) with 1 μg streptavidin, followed by blocking with BSA. Biotinylated protein was then added to the wells and allowed to bind to the streptavidin for 1 hour. The plates were washed with TBST and used for phage ELISAs.

Results:

The following peptides were found to be displayed on phage that bound specifically to β-glucosidase:

| Displayed Peptide Sequence | Method | Library | Frequency |
|---|---|---|---|
| S S Q T D W R K I F Q S L S R (SEQ ID NO:95) | beads | K | 3 |
| S S S T D W L N V W R Q L S R (SEQ ID NO:96) | beads | N | 2 |
| S S A T D W G R V Y S I L S R (SEQ ID NO:97) | beads/sol | R | 5 |
| S S A S Y A P W P I Y F A S R (SEQ ID NO:98) | beads | W | 2 |
| S S G A F K P W P V Y S F S R (SEQ ID NO:99) | beads | W | 1 |
| S R Q V E V F K P W P V Y S R (SEQ ID NO:100) | beads/sol | K | 3 |
| S S S F K P W P I Y L G S S R (SEQ ID NO:101) | sol | P | 1 |
| S S E P F S V W P I Y K H S R (SEQ ID NO:102) | sol | W | 1 |
| S S S V P F A P W P V Y A S R (SEQ ID NO:103) | beads | P | 1 |
| S S T S L P F N R W P I Y S R (SEQ ID NO:104) | beads | N | 2 |

The peptides fall into two clusters based on homology. Different methods of immobilizing the protein produced similar results: peptides from both classes were isolated from solution or bead displayed target and identical peptides were isolated from the two methods. Peptides in the second cluster were isolated predominantly from the W and P fixed residue libraries, a finding which is in concordance with the PWP motif in the conserved sequence. Phage presenting peptides in the first group came from the N, K, and R libraries, again consistent with the consensus sequence in this cluster. The only conserved residues in this motif for which a fixed residue library was screened were D and W. In both cases, the consensus sequence extends for greater than 5 residues to the carboxy terminal side making it impossible for these libraries to encode peptidens which would bind to the target.

To see if the phage displaying these peptides were directed to the active site of the enzyme, a competition between phage and conduritol, an active site directed irreversible inhibitor of β-glucosidase activity, was carried out. The target was immobilized as above and was incubated with 3 mM conduritol for 3 hours. The plate was aspirated and a standard phage ELISA was carried out. The results are shown in FIG. 21. The binding of phage from group 2 was inhibited by conduritol, however the binding of phage from group 1 was unaffected. Conduritol is a small molecule (MW=162.1) and it is possible that phage from group 2 are recognizing a portion of the active site that does not overlap with the conduritol binding site. Therefore at least one of the groups display peptides which bind to the active site of the enzyme.

The following peptides displayed on the surface of phage were found to bind specifically to carboxypeptidase:

```
Displayed Peptide Sequence                    Library   Frequency

S R L L E V S P G W W Q M S R (SEQ ID NO:105)    P         9
S S F R E L K P G W W S Y S R (SEQ ID NO:106)    P         1
S S W G D Y F N W R D G L S R (SEQ ID NO:107)    N         2
```

The following peptides displayed on the surface of phage were found to bind specifically to alcohol dehydrogenase:

```
Displayed Peptide Sequence                    Library   Frequency

S R Q V E V F K P W P V Y S R (SEQ ID NO:108)    K         1
    S S S F K P W P I Y L G S S R (SEQ ID NO:109) P        1
  S V S V G M K P S P R P (SEQ ID NO:110)       PHD12      2
S S N Y W W Q S P V L S R H S R (SEQ ID NO:111)  CWL       1
    S S W Q G N V L L G N W I S R (SEQ ID NO:112) L        3
S S L L N E S R L Q W S T S R (SEQ ID NO:113)    R         1
```

For both of these targets there are peptides which have homology to each other and cluster as well as peptides which do not have any obvious homology to the cluster. Phage displaying these peptides are very specific to the target for which they were selected to bind. Cross reactivity ELISA assays show that they give signals at least 10 times as stronger on the specific target vs any other targets tested.

The following peptides displayed on the surface of phage were found to bind specifically to biotinylated ProRS:

```
Displayed Peptide Sequence                    Library   Frequency

S R D W G F W D W G V D R S R (SEQ ID NO:114)    D         5
S R D W G F W R L P E S M A S R (SEQ ID NO:115)  CWL       3
S R E W H F W R D Y N P T S R (SEQ ID NO:116)    R         4
S S E R G S G D R G E K G S R (SEQ ID NO:117)    D         1
```

These sequences are markedly different from those in example 4 above where the target was immobilized directly on IMMULON 4 microtitration test plates. It is likely that upon binding to plastic that the proteins conformation is altered and so may present a distorted binding site. Selection for phage which bind in solution may represent peptides which bind to a more native form of the protein and thus are a better indicator of the native conformation of the target.

Similar affinity selection procedures could be carried out using glycogen phosphorylase a and yeast hexokinase. For each of the targets in this example, enzyme activity could be monitored in the absence and presence of phage displaying peptides or using synthetic peptides to determine if they are effective inhibitors. In addition, competitions between the phage/synthetic peptides and inhibitors or substrates could be carried out to determine if the surrogate ligands identified are binding at the active site of the target. These surrogate ligands could be used to format a competitive binding assay used to search for small molecular weight inhibitors of each of these targets as described in the above examples.

From the data presented here it is clear that some proteins are very sensitive to inactivation upon binding to plastic. The use of streptavidin coated microtiter plate or beads in conjuction with biotinylated target protein provides one alternative method for the presentation of the target protein.

Other methods of target presentation such as using an antibody to an epitope tag or a ligand:fusion protein combination, as well as others may be advantageous in the selection of phage and in the screen for small molecule inhibitors.

Example 9 (Hypothetical)

Identification of Inhibitors of the B7:CD28 Complex

Background.

There is a large and growing body of biological literature which suggests that expression of B7 on the antigen presenting cell can have a critical role of the outcome of the subsequent immune response. Expression of B7 is a potent adjuvant for the priming of T cell in vitro, and more importantly, in vivo.

There is substantial evidence that this priming occurs, at least in part, through the involvement of CD28. CD28 is a relatively high affinity receptor for B7. Engagement of CD28 on the surface of a T cell results in increased activity in a cREL dependent pathway. Blocking B7/CD28 interaction with antibody to B7 inhibits signal transduction, and results in a failure to efficiently prime T cells. Clearly compounds which block this interaction would have potent immunologic properties.

Peptides as molecular probes. We propose to identify small B7-surrogate ligands for CD28 from enhanced phage displayed peptide libraries to characterize the B7 binding site on CD28 and to establish screens for low molecular weight compounds that block the B7/CD28 interaction. We have chosen to develop CD28 binding peptides for several reasons.

1. Clone and Express the Membrane Distal Fragment of CD28 in a Fusion Protein Expression System.

The extracellular domain of CD28 will be cloned from the CD28 cDNA by PCR. PCR amplified product (with linkers) will be cloned into the TA plasmid (Invitrogen, San Diego, Calif., pCRII vector, "Original TA cloning kit"). We will subsequently insert it the pGEX2T vector (Pharmacia) to generate fusion proteins. Sequences of the inserts will be confirmed by automated sequencing. Subsequently, bacteria harboring the recombinant plasmids will be induced to express the GST-CD28 extracellular domain fusion proteins. The proteins will be purified by simple affinity chromatography with glutathione-agarose (Pharmacia).

If we have difficulty producing the external domain as a GST fusion, we will clone it into an Ig fusion construct as has been successfully done with CTLA4-Ig and CD28-Ig [Peach, 1995 #9]. We will produce this fusion construct in mammalian cells and purify it from supernatants using protein A disks.

2. Screen a Bacteriophage M13 Random Peptide Libraries for Peptides that Bind CD28.

Phage-displayed random peptide libraries within a manner similar to that described in Example 1, will be screened for binding to immobilized GST-CD 28 fusion proteins using affinity selection techniques.

The binding of individual isolates to the GST-CD28 fusion proteins will be evaluated by a simple enzyme linked immunosorbent assay (ELISA) with a goat anti-phage antibody conjugated to horseradish peroxidase (Pharmacia).

3. Sequence Phase and Determine Consensus CD28 Binding Peptide. Check for Homology With Known CD28 Binding Ligands, B7.1 and B7.2.

Consensus sequences of CD28 binding peptides will be determined in a manner similar to that described for UL44 in Example 1. By comparisons of sequences of the phage from the apparent "preferred" library with those from the other libraries we should be able to obtain a definition for an optimal CD28 binding peptide ligand. These consensus sequences are anticipated to be useful in computer searches such as those using the PROSITE system and the SWISS Protein database to identify novel CD28 ligands. We anticipate that some of the CD28 binding peptides may have similarity to the CD28 binding domains within B7.1 and B7.2. Based on published observations [Peach, 1995 #9], we might expect to see some structural similarity to the GFCC'C" beta-sheet face of the IgV fold and the ABED beta-sheet face of the IgC domain in B7.1 and/or B7.2.

The binding activity of motifs identified by phage-display will be confirmed with synthetic peptides. We will synthesize peptides with an attached biotin residue and then follow relative binding by ELISA [Sparks, 1994 #108;] and dot blots. Actual $K_d$ measurements will be determined for non-biotinylated peptides by fluorescence polarization. In addition, dissociation constants will be quantitated on a BIAcore instrument (Pharmacia). It is likely that we will find mimetic sequences in addition to those with similarity to the authentic ligands. We will further characterize both types of sequences below. In addition we have the possibility of identifying sequences which are similar to other unknown ligands of CD28, which may bind other sites on the CD28 protein. Characterization of these will be especially interesting since they may allow us to define previously unknown signaling pathways using CD28.

4. Test Peptide for Agonist/antagonist Activity in CD28 Dependent T Cell-based Assays.

The ability of dendritic cells (or EBV transformed B cells) to stimulate mixed lymphocyte responses will be the basis of our main biological assay. We will measure both $^3$H-Tdr incorporation on day 5, and will follow induction of the IL-2R (CD25) on day 2 by FACS using directly conjugated antibody. Il-2R up regulation is an early event in T cell activation. It may provide a more rapid and sensitive readout than proliferation.

To perform these experiments we will incubate normal peripheral blood monocytes (PBMCs) with stimulator cells in the presence of a varying numbers of stimulator cells. We will prepare dendritic cell stimulators from an MHC mismatched individual by growing dendritic cells from PBMC in IL-4 and GMCSF [Romani, 1994 #119; Xu, 1995 #122]. Such cultures are markedly enriched in DC and are potent MLC stimulators. Cultures will be tested for the number of Class II$^+$, B7$^+$ cells by flow cytometry. Peptide will be added at increasing concentrations to the cultures, and the response measured. Negative controls will consist of irrelevant peptides of similar size and amino acid composition. The combination of PMA plus anti-CD28 treatment will serve as a positive control and indicate the maximal T cell response. All data points will be collected in triplicate, and data will be analyzed using standard statistical methods.

We expect that antagonist peptides will result in a shift in the dose response curve towards higher stimulator cell concentrations for an equivalent T cell response. Peptides with agonist activity would be expected to shift the dose response to lower numbers of stimulator cells. We anticipate that these peptides may function either as agonist, activating CD28, or antagonists, blocking CD28 dependent responses. Any peptides that fail to show blocking activity will be tested for agonist activity using suboptimal doses of anti-CD3 to stimulate T cells. Those peptides which can act as agonists will showed enhanced responses. Anti CD28 antibody will be a control for these responses.

These data will be confirmed and refined using dose response curves of peptides. Peptides will be added to culture at a single concentration stimulators (added to give 50% maximum stimulation) at varying peptide doses. Antagonist peptides should show a diminishing response as the dose increases while agonists will show stimulation above baseline as dose increases. Partial agonists are also possible. This would inhibit at low dose, but stimulate at high doses. MHC binding peptides with this characteristic have been reported (32).

Clearly the largest stumbling block to this program would be a failure to obtain CD28 extracellular domain binding proteins. Based on our previous experience, we believe that this is highly unlikely since that portion of CD28 clearly binds other proteins (B7), even when monomeric. However, if in the unlikely event this is the case, we will make a fusion construct between the extracellular domain of B7.1 and bacterial alkaline phosphatase (BAP). If the affinity of this domain for GST-CD28 is too high (greater than 1 micromolar), we will selectively mutate the B7 sequences to lower the affinity to a range acceptable for use in compound library screens.

5. Establish a High Through-put Screen of Combinatorial Chemical Ligands for the GST-CD28 Fusion Proteins.

Combinatorial chemical libraries will be screened to identify B7/CD28 antagonists. These compounds will be used to disrupt B7/CD28 function in vivo. We will screen the benzodiazepine library described above and other chemical diversity libraries, in a manner similar to that described for UL44 in Hypothetical Example 1.

Once specific compounds with binding activity have been identified we will test their cross-reactivity with other functional homologues of CD28 as well as families of functional domains e.g. SH3, WW and PTB domains. We can rapidly determine specificity by testing whether the compound prevents the binding of biotinylated peptide ligands to extracellular domains of CTLA4 as well as other control fusion proteins. Compounds that competitively inhibit the binding of peptide ligands to CD28's extracellular domain will be used in biological experiments (see above).

If there is cross-reactivity between targets (which is quite possible) then a second-generation combinatorial chemical mini-library based upon the structure of the identified compounds will be generated. It is anticipated that some members of these purpose-built mini-libraries will bind to the CD28 domains with greater specificity and possibly greater affinity than to CTLA4. We seek to identify compounds that are active in the nanomolar range.

References for Example 9

Sparks, A. B., L. A. Quilliam, J. M. Thorn, C. J. Der, B. K. Kay. 1994. Identification and characterization of Src SH3 ligands from phage-displayed random peptide libraries. *Journal of Biological Chemistry*. 269: 23853–6.

Peach, R. J., J. Bajorath, J. Naemura, G. Leytzie, J. Greene, A. Aruffo, P. S. Linsley. 1995. Both extracellular immunoglobin-like domains of CD80 contain residues critical for binding T cell surface receptors CTLA-4 and CD28. *Journal of Biological Chemistry*. 270: 21181–7.

Romani, N., S. Gruner, D. Brang, E. Kampgen, A. Lenz, B. Trockenbacher, G. Konwalinka, P. O. Fritsch, R. M. Steinman, G. Schuler. 1994. Proliferating dendritic cell progenitors inhuman blood. *Journal of Experimental Medicine*. 180: 83–93.

Xu, H., M. Kramer, H. P. Spengler, J. H. Peters. 1995. Dendritic cells differentiated from human monocytes through a combination of IL-4, GM-CSF and IFN-gamma exhibit phenotype and function of blood dendritic cells. *Advances in Experimental Medicine & Biology*. 378: 75–8.

Example 10 (Hypothetical)

Identification of Antagonists of Apotoptic Proteins

Background

Programmed cell death, also known as apoptosis, is both a normal and abnormal cellular process. There are several examples of normal cell death that occur during embryo development, such as formation of digits in limbs, destruction of larval muscles during metamorphosis of the moth, sculpting of the mouth, removal of misconnected neurons, and removal of thymocytes that recognize self antigens. Defects in the control of cell death have also been described as the basis of certain forms of autoimmunity, escape of cancer cells from growth control, and immortalization of virally infected cells, to name a few. Thus, the molecular basis of apoptosis is considered by many scientists to be critical in understanding normal and abnormal growth control. If the molecules involved in cell death can be defined, they will serve as valuable targets with which to develop therapeutic drugs that may be used to block or induce apoptosis. These drugs may have uses in treating certain forms of autoimmune disease, fighting bacterial and viral infection, promoting survival of damaged neurons, and battling cancer.

Many of the molecules involved in the initiation of apoptosis are known. They include such proteins as tumor necrosis factor (TNF) receptor, nerve growth factor (NGF) receptor, Fas receptor (also known as APO-1 and CD95), a variety of immune cell receptors, an Rb interacting protein, a nematode neuronal guidance protein, and two fly proteins involved in embryonic axis formation. The TNF-, NGF-, and Fas-Receptors (R) are members of the TNF-R protein family, which consists of 12 members. The extracellular domains of the family all share from three to six cysteine-rich domains. While the extracellular domains are relatively conserved, the cytoplasmic regions are not, with the exception of the TNF-, NGF-R, and Fas-R molecules which share a ~80 amino acid domain. Functional analyses (see below) have shown that this domain plays an essential role in the cell death signalling of these receptors and hence the domain has been named the death domain (DD).

A consensus sequence has been established for the DD, even though the percent amino acid identity among the different DD sequences is ~30%. An up-to-date comparison of the primary structures of 13 different DD's has been posted on the web (http://ulrec3.unil.ch/domains/dd/index.html) by Dr. Kay Kauffman. A comparison of the specific DD sequences of the TNF, NGF, and Fas receptors can be found in the alignment below. As can be seen, the degree of identity (open boxes) is low and dispersed over the entire length of the DD. Only a few residues (i.e., $gly^{17}$, $ile^{23}$, $asp^{24}$, $leu^{42}$, $trp^{45}$, $leu^{58}$ $leu^{62}$, $glu^{72}$) are conserved (bold faced below) in all three proteins.

NGF-R LNGSAGDTWRHLAGELGYQPEHIDSFTHE - - - ACPVRALLA (cont'd below)

Fas-R AGVMTLSQVKGFVRKNGVNEAKI-DEIKNDNVQDTAEQKVQLLR (cont'd below)

TNF-R TDDPATLYWKEFVRRLGLSD-HEIDRLELQNGRCLREAQYSMLA (cont'd below)

NGF-R SWATQD - - - SATLDALLAALRRIQRA-DLVESLCSESTATSPV (SEQ ID NO:118)

Fas-R NWHQLHGKKEAYDTLIKDLKKANLCT-LAEKIQTIILKDITS (SEQ ID NO:119)

TNF-R TWRRRTRREATLELLGRVLRDM-DLLGCLEDIEEALCAPPLP (SEQ ID NO:120)

In the case of the TNF and Fas receptors, their DD's have been shown to be critical in activating cell death. When cDNA clones encoding either receptor are introduced into various cell lines, these cells will undergo apoptosis in the presence of TNF or the Fas ligand (Nagata and Golstein, 1995). However, if the transfected receptors have mutations in their DD's, apoptosis fails to occur in the presence of the extracellular signal (Tartaglia et al., 1993). Truncations of as little as 10 amino acids from the N-terminus or three from the C-terminus of the domain are inactivating. Furthermore, when most residues (black boxes) in the TNF-R DD (above alignment) were replaced with alanines, the receptor no longer caused apoptosis in host cells. Interestingly, a naturally occurring mutation in the Fas-R has been observed: in the lpr mouse, which experiences lymphocyte proliferation and an autoimmune syndrome resembling human systemic lupus erythematosus, there is a single amino acid mutation (equivalent to a change at V238; of the human Fas-R protein sequence) in the DD of the Fas receptor (Watanabe-Fukunaga et al., 1992). [The equivalent phenotype occurs in the gld mouse, where the Fas ligand is defective (Takahashi et al., 1994).] Thus, it is clear that proper function of the TNF- and Fas-R requires intact DD's.

Both the MORT1/FADD and TRADD proteins share an additional motif, termed the death effector domain (DED).

This 80 amino acid long domain is 18–38% identical between examples. The DED plays an essential role in cell death because if the domains are removed from FADD, cell death is blocked (Chinnaiyan et al. 1996). Conversely, if only the first DED (aa 1–117) is expressed in cells, apoptosis is triggered (Chinnaiyan et al. 1996).

1. Construct Glutathione S-Transferase (GST) Fusions with Cell Death Domains from Several Different Protein.

For use as targets, we will prepare GST-cell death domain fusion proteins.

To verify that the peptides bind the DD's in a biologically relevant manner, we will test their sensitivity to inactivating mutations of the DD's. One negative control that we will generate will be equivalent of the mouse lpr mutation (Watanabe-Fukunaga et al., 1992) in the human Fas, TNF, and NGF receptor DD's. Other inactivating mutations can be introduced in the DD's according to those described in the literature (Tartaglia et al., 1993). GST fusions to mutant DD's will be useful as negative controls in experiments examining the specificity of peptide-DD interactions (i.e., the peptide ligands should bind poorly, or not at all, to the inactive DD's). The mutations will be engineered by replacing a pair of oligonucleotides during the assembly of the DD's for cloning (above).

2. Identify Peptide Sequences from a Phage-displayed Random Peptide Library that Bind to the GST-cell Death Domain Fusion Proteins.

We will screen phage-displayed random peptide libraries with GST-DD fusion proteins by affinity selection, in a manner analogous to that set forth for UL44 in Hypothetical Example 1.

The libraries will be screened according to standard techniques (Kay et al., 1993; Adey and Kay, 1996. In brief, several micrograms of GST-DD fusion protein will be immobilized in ELISA style microtiter plates. After nonspecific protein binding are blocked with excess protein (i.e., BSA, Pierce Chemical SUPERBLOCK chemical preparation), approximately $10^{11}$ phage are added to each well. After several hours incubation at 4° C., the liquid is discarded from the wells with 200 mM glycine (pH2) which denatures the protein-phage complex. Bacteria are infected with the released phage after the pH is neutralized and cultured overnight. The infected cells release phage, 1000 per minute per bacterium, so that the titer of the final culture is $10^{12}$ plaque forming units per ml. This constitutes one round of screening. The process is repeated three times in series, and the resulting phage are grown as isolates. We anticipate that the peptide ligand preferences for the individual DD's will vary, as DDs are <31% identical in amino acid sequence. Definition of an optimal DD peptide ligand will be useful in computer searches (http://expasy.hcuge.ch/sprot/scnpsit2.html) of possible cellular ligands. In addition, if we are successful in identifying a motif, we will generate an additional biased peptide libraries, as we did for SH3 (Sparks et al., 1996a) and WW (unpublished) peptide ligands, which should accelerate defining the peptide ligand specificity of other DD's in the future.

Conclusions regarding motifs will be confirmed with synthetic peptides. We will synthesize peptides with biotin attached and then follow their relative binding by an enzyme linked assay (Sparks et al., 1994) and dot blots. Actual $K_d$ measurements will be determined for non-biotinylated peptides by fluorescence polarization; the DD segment will be released from GST-DD fusion protein by thrombin cleavage and then fluorescenated at its N-terminus. Alternatively, if the peptide ligands lack tryptophan, the fluorescence properties of the DD's own tryptophans will be monitored instead during peptide-DD complex formation. In addition, dissociation constants will be quantitated on a BIAcore system, see Karlsson, Anal. Biochem., 228:274–280 (1995) and Raghavan, Structure, 3:331–3 (1995). Based on experience with other target molecules, peptides isolated from phage-displayed libraries are anticipated to have 10 $\mu$M to 10 nM dissociation constants. If desired to determine the importance of individual residues of the peptide ligands, and thereby faulitate the design of more efficient libraries for the target in question, we may prepare a set of alanine-scanned variants and measure their affinities.

The synthetic peptides will be used in competition experiments as well. Soluble peptides will be added to radioactive ($^{35}$S-methione labelled) cell lysates incubated with various GST-DD fusion proteins. A similar experiment was performed with SrcSH3 peptide ligands to demonstrate that they bound in the same way as natural ligands (Sparks et al., 1994). If the peptides bind to the DD, little or no cellular protein should bind to the GST-DD fusion protein when it is recovered by chromatography over glutathione-agarose, resolved by SDS-PAGE, and autoradiographed. Non-binding peptides will serve as negative controls. If the peptides fail to block the interactions, due to their low affinities relative to natural ligands, we will retest them in a multivalent format. Biotinylated peptide ligands will be complexed with streptavidin to raise the affinity of the peptides to the DD's through avidity. In experiments with peptide ligands to SH3 domains, isolated from phage-displayed random peptide libraries, it was shown that raising the valency of the peptides to four is an effective means of increasing their apparent affinities.

3. Screen a Human λcDNA Expression Library by COLT to Identify Novel Cell Death Domain-containing Proteins.

One concern in evaluating a drug lead is its cross-reactivity. That is, a drug may yield undesirable side effects due to its interaction to an unwanted target. Given that DD's share some identity, the most likely cross-reactive targets of a DD specific compound will be other DD containing proteins. At the moment, only nine DD containing proteins are known. Other DD containing proteins may be identified by the COLT technique (Sparks et al., 1996b). COLT has been used to isolate over 20 SH3 domain containing proteins, or which half are novel. In unpublished work, we have used COLT to identify members of the calmodulin family as well as proteins containing WW domains. The WW domain is newly described protein motif of 38 amino acids, typified by two conserved tryptophan residues (Sudol et al., 1995), which binds proline-rich (Chen and Sudol, 1995). COLT is the preferred way of identifying other DD domain containing proteins in the human or other genomes.

Peptides corresponding to DD ligands will be synthesized with biotin, complexed to streptavidin-linked alkaline phosphatase, and used to screen λ human cDNA libraries. Such as T cell (Jurkit) and HeLa cDNA libraries. Lambda plaques expressing DD-containing proteins should form blue plaques on nitrocellulose filters when exposed to the peptide complex and NBT and BCIP. The cDNA inserts of such plaques will be rescued (Short et al., 1988) and their nucleotide sequences determined by dideoxy sequencing.

We propose to clone DD containing proteins systematically from the human genome according to the paradigm described below. We will identify a peptide ligand for a given DD that has been expressed as a GST-DD fusion protein. A biotinylated form of the peptide will be used in COLT to isolate cDNA clones encoding DD containing proteins. We will then subclone and express as GST fusion proteins novel DD's for the purpose of identifying their optimal peptide ligands. These ligands will then be used in turn to clone other novel DD containing proteins. In this iterative manner, a large number of DD can identified from the human genome. Such a collection will be important for the purpose of identifying other potential components of the cell death pathways as well as for drug discovery (see below).

Later, we will focus on the generation of drug leads that interfere with the function of the TNF, NGF, and Fas receptor DD domains. A high throughput screen (HTS) will be used to screen combinatorial libraries of benzodiazepines, peptoids, and other small chemicals. Such a screen will be based on fusing the peptide ligands identified as described above to the enzyme alkaline phosphatase (AP) and then looking for compounds that inhibit binding of the peptide ligand-AP fusion to GST-DD protein immobilized in microtiter plate wells. Another screen will be to fuse the DD directly to the AP and then staining beads that have the combinatorial compounds attached. To generate a drug specific to one particular DD containing protein it will be essential to test the cross-reactivity of a drug lead against unrelated DD's. If tests for cross-reactivity can implemented early in drug discovery, it is likely that the final product will have less toxicity due to interaction with unintended DD containing cellular proteins. Any potential drugs will be tested in model cell death systems. The discovery of drug leads that act by interfering with the interaction of proteins involved in apoptotic pathways may prove valuable in the treatment of numerous human diseases.

References for Example 10

Adey, N. B., and Kay, B. K. (1996). Identification of calmodulin-binding peptide consensus sequences from a phage-displayed random peptide library. *Gene* 169, 133–134.

Adey, N. B., Mataragnon, A. H., Rider, J. E., Carter, J. M., and Kay, B. K. (1995). Characterization of phage that bind plastic from phage-displayed random peptide libraries. *Gene* 156, 27–31.

Chinnalyan, A. M., O'Rourke, K., Tewari, M., and Dixit, V. M. (1995). FADD, a novel death domain-containing protein, interacts with the death domain of Fas and initiates apoptosis. *Cell* 81, 508–512.

Kay, B. K., Adey, N. B., He, Y.-S., Manfredi, J. P., Mataragnon, A. H., and Fowlkes, D. M. (1993). An M13 library displaying 38-amino-acid peptides as a source of novel sequences with affinity to selected targets. *Gene* 128, 59–65.

Sparks, A., Rider, J., Hoffman, N., Fowlkes, D., Quilliam, L., and Kay, B. (1996a). Distinct ligand preferences of SH3 domains from Src, Yes, Abl, cortactin, p53BP2, PLCγ, Crk, and Grb2. *Proc. Natl. Acad. Sci. USA* 93, 1540–1544.

Sparks, A. B., Hoffman, N. G., McConnell, S. J., Fowlkes, D. M., and Kay, B. K. (1996b). Cloning of ligand targets: Systematic isolation of SH3 domain-containing proteins. *Nat. Biotech.* 14, 741–744.

Sparks, A. B., Quilliam, L. A., Thorn, J. M., Der, C. J., and Kay, B. K. (1994). Identification and characterization of Src SH3 ligands from phage-displayed random peptide libraries. *J. Biol. Chem.* 269, 23853–23856.

Tartaglia, L. A., Ayres, T.-Mi., Wong, G. H. W., and Goeddel, D. V. (1993). A novel domain within the 55 kD TNF receptor signals cell death. *Cell* 74, 845–853.

Watanabe-Fukunaga, R., Brannan, C. I., Copeland, N. G., Jenkins, N. A., and Nagata, S. (1992). Lymphoproliferation disorder in mice explained by defects in Fas antigen that mediates apoptosis. *Nature* 356, 314–317.

Example 11

Isolation of Surrogate Ligands for Estrogen and Other Nuclear Receptor

Nuclear receptors are a family of ligand activated transcription factors which include the receptors for steroid and thyroid hormones, retinoids and vitamin D. The receptors are organized into distinct domains for ligand binding, dimerization, transactivation, and DNA binding. Ligand binding induces conformational changes in the receptors that allow for dimerization and the binding of co-activating proteins. These co-activators, in turn, facilitate the binding of the receptors to DNA and subsequent transcriptional activation.

The steroid receptor family of nuclear receptors is comprised of receptors for gluccorticoids, mineralocorticoids, androgens, progestins, and estrogens. Unique to the steroid and thyroid receptor families is a group of receptors known as orphan receptors. The genes for these receptors were cloned on the basis of their structural similarity to previously identified members of the steroid and thyroid receptor family. Certain orphan receptors are found only in specific tissues, while others are expressed ubiquitously. The common denominator of the orphan receptors is that they have no known ligand. Identifying ligands for these receptors would be of considerable value as there is evidence that members of the group of orphan receptors are important transcriptional regulators during critical stages of development. Identification of ligands for these orphan receptors would provide useful information for understanding regulation of gene expression as well as provide tools for discovering pharmacological agents. As a first step towards developing a method for the identification of orphan receptor ligands, current work is centered on a known member of the steroid family of nuclear receptors, the estrogen receptor α (ER). This receptor not only provides a model for the discovery of orphan receptor ligands, but it is also a current target for drug discovery.

Estrogens exert an influence on many important physiological functions including cell growth and differentiation, particularly in the tissues of the female and male reproductive tract. Estrogens have also been linked co the preservation of bone mass and protection of the cardiovascular system. Despite the positive effects of estrogen, the overexpression of the estrogen receptor (ER) in certain estrogen responsive tissues has been linked to diseases such as breast and ovarian cancer (Gallo and Kaufman, 1997). For this reason, the ER is a target for drug discovery. All of the ER therapeutic agents in use today are molecules that compete with estradiol for binding to the estrogen receptor. These compounds, called antiestrogens, are classified as either antagonists or partial agonists of estrogen receptor function. While effective, these compounds have adverse side effects such as loss of bone density and an increased risk of uterine cancer. Additionally, the cancers eventually become resistant to these agents (Katzenellenbogen, et.al, 1997). Because of these shortcomings in the current treatment for ER related disease, new treatment methods are being sought.

Our approach is to identify, via phage display, peptide surrogate ligands or mimics of proteins that interact with the ER. This approach is unique in that not only is the estradiol binding pocket the target for small molecules, but also any site on the ER that is involved with receptor signaling.

As mentioned above, the ER is organized into distinct domains (FIG. 22). Several of these regions contain sites predicted to be useful for drug intervention of ER function. For instance, the estrogen receptor and other nuclear receptors interact with one or more steroid receptor co-activators (SRC's) via a conserved alpha-helical domain located within the AF2 region of the receptor. This interaction is ligand dependent and is believed to bridge the interaction between the receptor and transcriptional activation. Many co-activators have been identified and their interactions with several nuclear receptors have been investigated. Mutagenesis experiments have identified the sequence of the binding domain on the co-activator as an LXXLL (SEQ ID NO:121) motif where X is any amino acid. This sequence has been shown to be both necessary and sufficient for receptor binding (Heery et.al, 1997; Torchia et.al, 1997). The XX portion of this motif and the surrounding residues are believed to impart specificity to the interaction. Disruption of this interaction would be predicted to disrupt receptor signaling by blocking transcriptional activation. Peptides that mimic this interaction will provide a tool for discovering pharmacological agents that act at the co-activator binding site on the ER. Additional sites on the ER that could serve as targets for drug intervention include the AF1 region, the dimerization domain and the DNA binding domain. Once peptides are obtained for one or more of these sites, they can be used in a competitive displacement assay to screen libraries of compounds.

Methods and Results

The ER (Panvera Corp.) was immobilized on IMMULON 4 microtitration test plates (Dynatech) for the phage affinity selection, after it was determined that the immobilized ER was capable of binding estradiol. Phage display was conducted on the ER, as described in example 1 above, in both the presence and the absence of the natural ligand for the ER, 17-β estradiol (100 μM).

The sequences obtained in the absence of estradiol are shown in Table 11-1. These sequences possibly represent proteins that interact with the unliganded ER such as HSP90 (90 Kda heat shock protein). Two sequences compete with estradiol (FIG. 23). These sequences may bind to the estradiol binding pocket or they may bind to sites that are masked by a change in receptor conformation following binding of estradiol. The antiestrogen 4-hydroxytamoxifen does not inhibit the binding of any of these phage (FIG. 23).

Sequences obtained in.the presence of estradiol are shown in Tables 11-2 and 11-3. The sequences are overall leucine rich and the majority of them contain the LXXLL motif, which is found in the nuclear receptor co-activators described above.

In Tables 11-1 to 11-3, certain strongly conserved residues are boldfaced or underlined.

The effect of no estradiol, the weak agonist estriol, and the antiestrogens tamoxifen, nafoxidine and clomiphene on the binding of these phage to the ER was investigated. Immobilized ER was incubated with 100 μM estradiol, estriol, nafoxidine, tamoxifen or clomifene in TBST, or in TBST alone for 20 minutes prior to adding the phage supernatant from a fresh overnight culture. Following a 1 hour incubation, the wells were washed five times with TBST and the bound phage were visualized using an anti-M13 antibody coupled to HRP, as described in the examples above. For the LXXLL motif containing peptides, there was a range of effects from no effect of antiestrogen to a significant affect on the binding of phage (FIG. 24A). For the peptides that do not fit this consensus, there was also this same range of effects (FIG. 24B).

Peptides that contain the LXXLL motif and compete with antiestrogens are likely to be binding to co-activator binding sites that are only exposed upon binding of an estrogen like molecule or agonist. Peptides that do not compete with the antiestrogens may represent a site that is exposed upon antiestrogen and estrogen binding. Peptides that do not contain the LXXLL motif may represent proteins that interact by a distinct mechanism. These peptides may be used in biological studies to determine if they block the interaction of the ER with co-activators, or if they inhibit ER function. They may also be used in a drug screen to identify small molecules that block ER function at a site distinct from the estradiol binding pocket.

Application of the Technology to Other Nuclear Receptors and Orphan Receptors

The technology developed by working with the ER may be applied to the investigation of additional nuclear receptors as well as orphan receptors. Nuclear receptors including the estrogen receptor β, and the receptors for androgens, progesterone, glucocorticoid, retinoic acid, etc. would be approached in a similar manner by conducting phage display in the absence and presence of ligand. The receptors will also be biotinylated and phage will be affinity purified following immobilization of the receptor on streptavidin coated plates. It is likely that these approaches will identify unique sequences as well as additional LXXLL motifs with different specificities that are perhaps determined by the sequences surrounding the conserved leucine residues.

As mentioned above, the ligands for orphan receptors are unknown. This poses an obstacle to receptor activation prior to phage display. Possible sources of ligand for orphan receptors are fetal bovine serum or other enriched medium such as conditioned media from cells grown in culture. Once a peptide is identified that interacts with an orphan receptor in a serum or medium dependent manner, the peptide may be used to identify the natural ligand by fractionating serum, conditioned medium or other appropriate tissue homogenate. The peptides may also be used to screen compound libraries for pharmacologically active agents.

Peptides that bind to the ligand binding domain of orphan receptors may also be isolated. These peptides may be used in a competitive displacement assay to identify the natural ligand from a source described above. They may also be used to screen libraries of compounds to identify pharmacologically active species.

References for Example 11

Gallo, M. A., and Kaufman, D., 1997, Antagonistic and Agonistic Effects of Tamoxifen: Significance in Human Cancer, *Seminars in Oncology* 24 (Suppl.1), SI-71-SI-80.

Katzenellenbogen, B. S., Montano, M. M., Ekena, K. and McInerney, E. M., 1997, Anitestrogens: Mechanisms of Action and Resistance in Breast Cancer, *Breast Cancer Research and Treatment* 44, 23–28.

Heery, D. M., Kalkhoven, E., Hoare, S., and Parker, M. G., 1997, A Signature Motif in Transcriptional Co-Activators Mediates Binding to Nuclear Receptors, *Nature* 387, 733–736.

Torchia, J., Rose, D. W., Inostroza, J., Kamei, Y., Westin, S., Glass, C. K., and Rosenfeld, M. G., 1997, The Transcriptional C-Activator p/CIP Binds CPB and Mediates Nuclear Receptor Function, *Nature* 387, 677–684.

TABLE 11-1

Cluster Analysis for Estrogen Receptor

| Sequence | Phage # |
|---|---|
| S R T W E S P L G T W E W S R (SEQ ID NO:122) | 13 |
| S S K Y S Y S R S S E G H S R (SEQ ID NO:123) | 29 |
| S S W V R L S D F P W G V S R (SEQ ID NO:124) | 1 |
| S S W D R L S D F P W G V S R (SEQ ID NO:125) | 2 |
| S S W I R L R D L P W G E S R (SEQ ID NO:126) | 3 |
| S S W V L L R D L P W G S R (SEQ ID NO:127) | 31 |
| S S C K W Y E K C S G L W S R (SEQ ID NO:128) | 7 |
| S S G I C F F W D G C F E S R (SEQ ID NO:129) | 35 |
| S R N L C F F W D D E Y C D R (SEQ ID NO:130) | 41 |
| H H H R H P A H P H T Y G G (SEQ ID NO:131) | 47 |

TABLE 11-2

Cluster Analysis for ER + Estradiol

| Sequence | Phage # |
|---|---|
| S R A G L L S D L L E G K S R (SEQ ID NO:132) | 1/2 |
| S S R S L L R D L L M V D S R (SEQ ID NO:133) | 6 |
| S S N K L L Y N L L K M E S R (SEQ ID NO:134) | 22 |
| S S K S L L L N L L S T P S R (SEQ ID NO:135) | 23 |
| H S F P P E S L L V R L L Q G G (SEQ ID NO:136) | 42 |
| S R L E M L L R S E T D F S R (SEQ ID NO:137) | 3 |
| S R L E E L L K W G S V T S R (SEQ ID NO:138) | 11 |
| S R L E Q L L K E E F S Y S R (SEQ ID NO:139) | 21 |
| S R L E Q L L R S E P D F S R (SEQ ID NO:140) | 27 |
| S R L E D L L R A P F T T S R (SEQ ID NO:141) | 28 |
| S R L E S L L R F G Q L D S R (SEQ ID NO:142) | 29 |
| S S R L L S L L V G D F N S R (SEQ ID NO:143) | 19/20 |
| S R L E E L L L G T N R D S R (SEQ ID NO:144) | 30 |
| S R L K E L L L L P T D L S R (SEQ ID NO:137) | 15 |
| S R L E C L L E G R L N C S R (SEQ ID NO:146) | 34 |
| S S K L Y C L L D E S Y C S R (SEQ ID NO:147) | 35 |
| S R L S C L L M G F E D C S R (SEQ ID NO:148) | 36 |
| S S K L I R L L T S D E E L S R (SEQ ID NO:149) | 37 |
| S S R L M E L L Q E G Q G W S R (SEQ ID NO:150) | 40 |
| S S N H Q S S R L I E L L S R (SEQ ID NO:151) | 4 |
| S R L <u>W</u> Q L L A S T D T S R (SEQ ID NO:152) | 16 |
| S S N S M L <u>W</u> K L L A A P S R (SEQ ID NO:153) | 13/14 |
| S S K T L <u>W</u> R L L E G E R S R (SEQ ID NO:154) | 17 |
| S R A G P V L <u>W</u> G L L S E S R (SEQ ID NO:155) | 32 |

TABLE 11-3

Additional Sequences frm ER + Estradiol

| Sequence | Phage # |
|---|---|
| S S L T S R D F G S W Y A S R * (SEQ ID NO:156) | 5 |
| S S W V R L S D F P W G V S R * (also isolated (-) estradiol) (SEQ ID NO:157) | 24/25 |
| S S E Y C F Y W D S A H C S R * (SEQ ID NO:158) | 33 |
| S R S L L E C H L M G N C S R (SEQ ID NO:159) | 7 |
| S S E L L R W H L T R D T S R (SEQ ID NO:160) | 8 |
| S R L E Y W L K W E P G P S R (SEQ ID NO:161) | 12 |
| S R S D S I L W R M L S E S R (SEQ ID NO:162) | 31 |
| S S K G V L W R M L A E P V S R (SEQ ID NO:163) | 38/39 |
| H S H G P L T L N L L R S S G G (SEQ ID NO:164) | 41 |
| S S A G G G A P A G S T P S R (SEQ ID NO:165) | 26 |
| S S Y Q W E T H S D K W R S R (weak binder) (SEQ ID NO:166) | 10 |
| S S V T K K A L T I A K D S R (weak binder) (SEQ ID NO:167) | 18 |

*binding not inhibited by antiestrogens

Additional Remarks

While the primary utility of the surrogate peptides disclosed above is in screening for non-peptide antagonists of the biological activity of the receptor to which they bind, the peptide may also themselves be useful as agonists or antagonists of the receptor, or as the binding component of a diagnostic agent which binds the receptor.

Surrogate peptides of particular interest, either in screening, or as therapeutic or diagnostic agents in their own right, incle (but are not limited to) those comprising the sequences shown below:

| Ex | Target | Peptide | |
|----|--------|---------|---|
| 1 | HCMV UL44 | E-H-V-C-S-W-G-W-G-R-C | (SEQ ID NO: 168) |
| | | D R L   T       K | (SEQ ID NO: 169) |
| | | N K I   A       H | (SEQ ID NO: 170) |
| | | Q   M   G | (SEQ ID NO: 171) |
| 2 | Protein Kinase CβII | W-Phi-C-Pho-G-X-(F/L)-C and W-T-C-(V/I)-N- C | |
| 3 | human MDM2 | S-F-T-D-Y-W-R-D-L-E-Q and conservative mutants thereof. | (SEQ ID NO: 172) |
| 5 | tyrosine tRNA | Y-Phi-W-P-W and Y-Phi-W-P-Phi and (Y/F)-(S/T/G/A/H)-W-P(W/G/D/S/P) and (Y/F/W/L)-W-W-P-(D/E/S/N)-W-G | |
| 8 | glucosidase | {F-K}-P-W-P-(I/V)-Y { }=optional | |
| | carboxypeptidase | P-G-W-W | (SEQ ID NO: 173) |
| | ProRS | S-R-D-W-G-F-W | (SEQ ID NO: 174) |
| | | E | (SEQ ID NO: 175) |
| 11 | Estrogen Receptor | W-Pho-R-L-Phi-D-PhO-P-W-G and C-F-F-W-D and | (SEQ ID NO: 176) |
| | | L-X-X-L-L | (SEQ ID NO: 177) |

General References

Doorbar, J. and G. Winter. 1994. Isolation of a peptide antagonist to the thrombin receptor using phage display. J. Mol. Biol. 244:361–369.

Smith, G. P., D. A. Schultz and J. E. Ladbury. 1993. A ribonuclease S-peptide antagonist discovered with a bacteriophage display library. Gene 128:37–42.

Sato, A., N. Ida, M. Fukuyama, K. Miwi, J. Kazami, and H. Nakamura. 1996. Identification from a phage display library of peptides that bind to toxic shock syndrome toxin-1 and that inhibit its binding to major histocompatibility complex (MHC) class II molecules. Biochemistry 35:10441–10447.

Hong, S. S. and P. Boulanger. 1995. Protein ligands of the human adenovirus type 2 outer capsid identified by biopanning of a phage-displayed peptide library on separate domains of wild-type and mutant penton capsomers. EMBO Journal 14:4714–4727.

Balass, E. Katchalski-Katzir and S. Fuchs. 1997. The alpha-bungarotoxin binding site on the nicotinic acetylcholine receptor: Analysis using a phage-epitope library. PNAS 94:6054–6058.

Scott, J., D. Loganathan, R. B. Easley, X. Gong and I. Goldstein. 1992. A family of concanavalin A-binding peptides from a hexapeptide epitope library. PNAS 89:5398–5402.

Oldenburg, K. R., D. Loganathan, I. J. Goldstein, P. G. Schultz, and M. Gallop. 1992. Peptide ligands for a sugar-binding protein isolated from a random peptide library. PNAS 89:5393–5397.

Wrighton, N. C., F. X. Farrel, R. Chang, A. K. Kashyap, F. P. Barbone, L. S. Mulcahy, D. L. Johnson, R. W. Barrett, L. K. Jolliffe, W. J. Dower. 1996. Small peptides as potent mimetics of the protein hormone erythropoietin. Science 273:458–463.

Murayama, O., H. Nishida and K. Sekiguchi. 1996. Novel peptide ligands for integrin alph6beta1 selected from a phage display library. J. Biochem. 120:445–451.

Koivunen, E., B. Wang, and E. Ruoslahti. 1994. Isolation of a highly specific ligand for the alpha5beta1 integrin from a phage display library. J. Cell Biol. 124:373–380.

Pasqualini, R., E. Koivunen and E. Ruoslahti. 1995. A peptide isolated from phage display libraries is a structural and functional mimic of an RGD-binding sited on integrins. J. Cell Biology 130:1189–1196.

Bottger, V., A. Bottger, S. F. Howard, S. M. Picksley, P. Chene, C. Garcia-Echeverria, H-K. Hochkeppel and D. P. Lane. 1996. Identification of novel mdm2 binding peptides by phage display. Oncogene 13:2141–2147.

Villar, H. O. and L. M. Kauvar, 1994. Amino acid preferences at protein binding sites. FEBS Letters 349:125–130.

We hereby claim:

1. A method of identifying a ligand which can mediate the biological activity of a target protein via inhibition of the binding of a target protein to a binding partner ligand which comprises
   (a) screening a first combinatorial library comprising a plurality of first member ligands for binding to the target protein, thereby identifying one or more target-binding ligands,
   (b) screening a second library comprising a plurality of second member ligands for the ability to inhibit the binding of one or more of said target-binding ligands to said target protein, thereby obtaining one or more inhibitory ligands, and
   (c) determining which of the inhibitory ligands can mediate a biological activity of the target protein,
       said inhibitory ligand thereby being identified as an activity-mediating ligand,
       in which the target protein is a nuclear receptor of the steroid receptor family,
       in which the first library is composed of peptides, the peptides do not comprise antibody-like domains, at least one peptide is characterized by an amino acid sequence comprising the Leu-Xaa-Xaa-Leu-Leu (Seq. ID. NO.121) sequence motif, wherein Xaa represents any genetically encoded amino acid, and the peptides are displayed on phage, and
       in which the second library is a non-biopolymeric combinatorial library.

2. The method of claim 1 in which the first combinatorial library has a greater diversity than the second library.

3. The method of claim 1 in which the target-binding ligands obtained in step (a) are tested in a suitable biological system for the ability to interact with the target protein so as to mediate its biological activity and only the effective ligands are used in screening step (b).

4. The method of claim 1 in which the inhibitory ligands obtained in step (b) are tested to determine whether their inhibitory action is attributable to their binding the target protein or to their binding the target-binding ligand.

5. The method of claim 1 in which the second library is a benzodiazepine library.

6. The method of claim 1 in which the target protein is an estrogen receptor.

7. The method of claim 1 in which said first library diversity of at least $10^3$ different sequences.

8. The method of claim 1 in which said second has a diversity of at least 100 different structures.

9. The method of claim 1 in which said first library has a diversity of at least $10^6$ different sequences.

10. The method of claim 1 in which said first library has a diversity of $10^3$ to $10^9$ different sequences.

* * * * *